US012774316B2

(12) United States Patent
Riley et al.

(10) Patent No.: US 12,774,316 B2
(45) Date of Patent: Oct. 27, 2026

(54) ANTI-CD3 scFv AND CYTOKINE PRODUCING ARTIFICIAL ANTIGEN PRESENTING CELLS

(71) Applicant: THE TRUSTEES OF THE UNIVERSITY OF PENNSYLVANIA, Philadelphia, PA (US)

(72) Inventors: James L. Riley, Downingtown, PA (US); Gavin Ellis, Philadelphia, PA (US); Jun Xu, Cherry Hill, NJ (US); Jan Melenhorst, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 947 days.

(21) Appl. No.: 17/778,734

(22) PCT Filed: Nov. 25, 2020

(86) PCT No.: PCT/US2020/062220
§ 371 (c)(1),
(2) Date: May 20, 2022

(87) PCT Pub. No.: WO2021/108543
PCT Pub. Date: Jun. 3, 2021

(65) Prior Publication Data
US 2023/0000916 A1 Jan. 5, 2023

Related U.S. Application Data

(60) Provisional application No. 62/941,062, filed on Nov. 27, 2019.

(51) Int. Cl.
*C07K 14/705* (2006.01)
*A61K 40/11* (2025.01)
(Continued)

(52) U.S. Cl.
CPC .......... *C07K 14/7051* (2013.01); *A61K 40/11* (2025.01); *A61K 40/24* (2025.01);
(Continued)

(58) Field of Classification Search
CPC ........... C07K 14/7051; C07K 16/2809; C07K 2317/565; C07K 2317/622;
(Continued)

(56) References Cited

U.S. PATENT DOCUMENTS 7,169,894 B2 * 1/2007 Martin ............... G01N 33/6803 435/7.1
2004/0043401 A1 3/2004 Sadelain
(Continued)

FOREIGN PATENT DOCUMENTS

AU 2018227583 B2 * 9/2018 ........... C07K 14/505
CN 109306340 2/2019
(Continued)

OTHER PUBLICATIONS

Oyer, J.L., et al (2015) Generation of highly cytotoxic natural killer cells for treatment of acute myelogenous leukemia using a feeder-free particle-based approach Biol Blood Marrow Transplant 21; 632-639 (Year: 2015).*
(Continued)

*Primary Examiner* — Scarlett Y Goon
*Assistant Examiner* — Audrey L Buttice
(74) *Attorney, Agent, or Firm* — Saul Ewing LLP; Kathryn Doyle; Alireza Behrooz

(57) ABSTRACT

The present invention includes compositions and methods for expanding T cells utilizing artificial antigen presenting cells (aAPCs) comprising a chimeric receptor molecule specific for CD3.

20 Claims, 43 Drawing Sheets

Specification includes a Sequence Listing.

(51) Int. Cl.

| | |
|---|---|
| ***A61K 40/24*** | (2025.01) |
| ***A61K 40/31*** | (2025.01) |
| ***A61K 40/42*** | (2025.01) |
| ***A61P 35/00*** | (2006.01) |
| ***C07K 16/28*** | (2006.01) |
| ***C12N 5/078*** | (2010.01) |
| ***C12N 5/0783*** | (2010.01) |

(52) U.S. Cl.
CPC ............ *A61K 40/31* (2025.01); *A61K 40/421* (2025.01); *A61P 35/00* (2018.01); *C07K 16/2809* (2013.01); *C12N 5/0634* (2013.01); *C12N 5/0636* (2013.01); *C07K 2317/565* (2013.01); *C07K 2317/622* (2013.01); *C07K 2319/03* (2013.01)

(58) Field of Classification Search
CPC .... C07K 2319/03; A61K 40/11; A61K 40/24; A61K 40/31; A61K 40/421; A61K 40/13; A61K 40/17; A61K 40/19; A61K 40/30; A61K 40/35; A61K 40/32; A61K 40/4224; A61K 2239/28; A61K 2121/00; A61K 2300/00; A61P 35/00; C12N 5/0634; C12N 5/0636; C12N 2501/515; C12N 2510/00; C12N 2740/16043
See application file for complete search history.

(56) References Cited

U.S. PATENT DOCUMENTS

| | | | | |
|---|---|---|---|---|
| 2006/0034810 A1 | 2/2006 | Riley | | |
| 2017/0258836 A1* | 9/2017 | Zhao | .................. | C07K 14/7151 |
| 2017/0319684 A1 | 11/2017 | Riley | | |
| 2019/0211075 A1 | 7/2019 | Davila | | |

FOREIGN PATENT DOCUMENTS

| | | |
|---|---|---|
| WO | 2008119567 | 10/2008 |
| WO | 2010037838 A2 | 4/2010 |
| WO | 2015164594 | 10/2015 |
| WO | 2018132508 | 7/2018 |
| WO | 2019020090 | 1/2019 |
| WO | 2019160956 | 8/2019 |

OTHER PUBLICATIONS

Leitner, J., et al (2010) T cell stimulator cells, an efficient and versatile cellular system to assess the role of costimulatory ligands in the activation of human T cells Journal of Immunological Methods 362; 131-141 (Year: 2010).*

Chen, B., et al (2017) The affinity of elongated membrane-tethered ligands determines potency of T cell receptor triggering Frontiers in Immunology 8(793); 1-21 (Year: 2017).*

Gould, N., et al (2014) Computational tools and algorithms for designing and customized synthetic genes Frontiers in Bioengineering and Biotechnology 2(41); 1-14 (Year: 2014).*

Lin, Y., et al (2013) The B7-1 cytoplasmic tail enhances intracellular transport and mammalian cell surface display of chimeric proteins in the absence of linear ER export motif Plos One 8(9), e75084; 1-26 (Year: 2013).*

Extended European Search Report issued Feb. 26, 2024 in European Patent Application No., 20891971.2, 16 pages.

Gao, J., et al., "Cell membrane-formed nanovesicles for disease-targeted delivery", Jin Gao et.al., Journal of Controlled Release, vol. 224 , pp. 208-216.

Butler, M.O., et al., "Human cell-based artificial antigen-presenting cells for cancer immunotherapy", Immunological Reviews, vol. 257, No. 1, pp. 191-209, 2013.

Deniger, D.C., "T-Cell Treatments for Solid and Hematological Tumors", UT GSBS Dissertations and Theses (Open Access), Paper 377, 310 pages, 2013.

Glaser , et al., "Novel antibody hinge regions for efficient production of CH2 domain-deleted antibodies.", J. Biol. Chem. (2005) 280:41494-41503.

Guo, Yin, et al. "Immunobiology of the IL-15/IL-15Rα complex as an antitumor and antiviral agent." Cytokine & growth factor reviews 38 (2017): 10-21.

Hasan, A. N., et al. "Soluble and membrane-bound interleukin (IL)-15 R α/IL-15 complexes mediate proliferation of high-avidity central memory CD8+ T cells for adoptive immunotherapy of cancer and infections." Clinical & Experimental Immunology 186.2 (2016): 249-265.

Hudecek, et al., "The non-signaling extracellular spacer domain of chimeric antigen receptors is decisive for in vivo antitumor activity", Cancer Immunol Res. 3(2), 2015,125-135.

International Search Report and Written Opinion issued in App. No. PCT/US20/62220, mailing date Apr. 9, 2021, 16 pages.

Partial Supplementary European Search Report issued Nov. 3, 2023 in European Patent Application No. 20891971.2. 17 pages.

Tamzalit, Fella, et al. "IL-15. IL-15Rα complex shedding following trans-presentation is essential for the survival of IL-15 responding NK and T cells." Proceedings of the National Academy of Sciences 111.23 (2014): 8565-8570.

Yan, Boxu, et al. "Engineering upper hinge improves stability and effector function of a human IgG1." Journal of Biological Chemistry 287.8 (2012): 5891-5897.

* cited by examiner

*From PCT/EP2009/062795*

Newly Engineered aAPC

| K562 | APC2.0 | APC3.0 | APC2.1 | APC3.1 | APC4.1* | APC5.1* |
|---|---|---|---|---|---|---|
| CD64 | + | + | + | + | + | + |
| 4-1BBL | + | + | + | + | + | + |
| CD86 | | + | | + | | + |
| CAR-3 | | | + | + | + | + |
| IL-7mcherry | | | | | + | + |
| IL-15-15R | | | | | + | + |

Fig. 12

| Criteria | Current Process (WAVE) | Proposed Process (GREX) |
|---|---|---|
| Yield (in cell number) | 1.82E10cells<br>182 pts: 1.00E8/pt | 2.00E10cells*<br>200 pts: 1.00E8/pt |
| Days of culture | 23 days | 7 days |

* Cell number obtained with GREX-100M for 7 days culture

Check previous staining results from fresh cells P3

4th Generation

- Nanoparticles from 3rd generation aAPCs
- Not alive
- Can be made in large batches simplify QC Industrial Size Available

| gating from 1.6um³ to 1000um³ | | |
|---|---|---|
| Date | Particle Conc. (Million/ml) | Particle mean size (um³) |
| 3/13/2020 small | 396 | 4.21 |
| 8/21/2020 small | 143 | 4.87 |
| 9/9/2020 large | 97 | 7.91 |
| 10/13/2020 large | 676 | 4.55 |

| Gating from 1.6um³ to 1000um³ | | |
|---|---|---|
| Date | Particle Conc. (Million/ml) | Particle mean size (um³) |
| 3/13/2020 small | 396 | 4.21 |
| 8/21/2020 small | 143 | 4.87 |
| 9/9/2020 large | 97 | 7.91 |
| 10/13/2020 large | 676 | 4.55 |

| CD8 | Division Index | Proliferation Index | Expansion Index | Replicatio n Index | Percent Divided |
|---|---|---|---|---|---|
| 10/13/2020 large scale 12.5ul | 0.99 | 1.98 | 3.19 | 5.38 | 50 |
| 10/13/2020 large scale 6.25ul | 1.37 | 2.2 | 4.49 | 6.6 | 62.3 |
| 10/13/2020 large scale 3.125ul | 1.37 | 2.23 | 4.82 | 7.21 | 61.5 |
| Beads | 1.58 | 2.32 | 5.27 | 7.27 | 68.1 |

How many APC5.1 cells we need to stimulate the same amount of T cells as 10ml bottle of beads

| 10ml bottle contains 4000 million beads to stimulate 1333.3 million T cells | how many million of APC cells we need equals to a bottle of beads | how many G-rex 6-well columns we need | how many bottles of Optmizer media we need |
|---|---|---|---|
| If we use 100ul membrane to stimulate 0.5M T cells | 26666 | 133.33 | 79.998 |
| If we use 50ul membrane to stimulate 0.5M T cells | 13333 | 66.665 | 39.999 |
| If we use 25ul membrane to stimulate 0.5M T cells | 6666.5 | 33.3325 | 19.9995 |
| If we use 12.5ul membrane to stimulate 0.5M T cells | 3333.25 | 16.66625 | 9.99975 |
| If we use 6.25ul membrane to stimulate 0.5M T cells | 1666.625 | 8.333125 | 4.999875 |
| If we use 3.125ul membrane to stimulate 0.5M T cells | 833.3125 | 4.1665625 | 2.4999375 |

Fig. 37

ANTI-CD3 scFv AND CYTOKINE PRODUCING ARTIFICIAL ANTIGEN PRESENTING CELLS

CROSS-REFERENCE TO RELATED APPLICATIONS

The present application is a 35 U.S.C. § 371 national phase application from, and claims priority to, International Application No. PCT/US2020/062220, filed Nov. 25, 2020, and published under PCT Article 21(2) in English, which claims priority under 35 U.S.C. § 119(e) to U.S. Provisional Application No. 62/941,062, filed Nov. 27, 2019 all of which applications are incorporated herein by reference in their entireties.

SEQUENCE LISTING

The ASCII text file named "046483-7268US1(02856)) Sequence Listing", created on May 19, 2022, comprising 34 Kbytes, is hereby incorporated by reference in its entirety.

BACKGROUND OF THE INVENTION

Immunotherapy involving the priming and expansion of T lymphocytes (T cells) holds the promise of effective treatment of cancer and infectious diseases. Current clinical uses of adoptive transfer therapy in patients with cancer and viral infections regularly involves the infusion of T cells that have been stimulated, cloned and expanded for many weeks in vitro on autologous dendritic cells (DC), virally infected B cells, and/or allogeneic feeder cells. However, adoptive T cell immunotherapy clinical trials routinely require billions of cells per patient. In order to produce these quantities of cells, T cells must be subjected to many fold expansion in vitro, requiring up to 40 population doublings. Furthermore, for optimal engraftment potential and possible therapeutic benefit at the time of re-infusion, it is important to ensure that the expanded T cells remain functional and are not senescent or exhausted.

Methods of expanding T cell clones and/or lines for adoptive immunotherapy have proven to have certain drawbacks. The standard culture of pure $CD8^+$ cells is limited by apoptosis, diminution of biological function and/or proliferation, and obtaining a sufficient number of cells to be useful has been particularly difficult. Indeed, it is possible that such T cells that are currently infused into patients, may have a limited replicative capacity, and therefore, could not stably engraft to provide long-term protection from disease. Furthermore, the various techniques available for expanding human T cells have relied primarily on the use of accessory cells (i.e. cells that support or promote T cell survival and proliferation such as PBMCs, DCs, B cells, monocytes, etc.) and/or exogenous growth factors, such as interleukin-2 (IL-2), IL-7, and IL-15. The requirement for accessory cells presents a significant problem for long-term culture systems because these cells are relatively short-lived. Therefore, in a long-term culture system, APCs must be continually obtained and replenished. The necessity for a renewable supply of accessory cells is problematic for treatment of immunodeficiencies in which accessory cells are affected. Likewise the need for exogenous mixtures of cytokines to support expansion and function of cultured T cells adds considerably to the costs, especially when stable sources of GMP-grade materials are required.

Thus, there exists a need to provide ways to stimulate T cells to combat various acute and chronic diseases and to promulgate sufficient numbers of therapeutic T cells for adoptive immunotherapy. The present invention addresses this need.

SUMMARY OF THE INVENTION

As described herein, the present invention relates to single-chain variable fragments (scFvs) specific for CD3 and artificial antigen-presenting cells (aAPCs) comprising anti-CD3 scFvs, as well as compositions comprising said aAPCs and aAPC-derived membrane vesicles, as well as methods of expanding T cells comprising said anti-CD3 scFvs, artificial APCs, aAPC-derived membrane vesicles, and compositions thereof.

As such, in one aspect, the invention includes an artificial antigen presenting cell (aAPC) comprising a chimeric receptor molecule comprising an antigen binding domain having specificity for human CD3 and a non-human primate CD3, and a transmembrane domain, wherein the antigen binding domain comprises:

- a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and
- a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

In some embodiments, the antigen binding domain comprises a heavy chain variable region comprising the amino acid sequence set forth in SEQ ID NO: 6.

In some embodiments, the antigen binding domain comprises a light chain variable region comprising the amino acid sequence set forth in SEQ ID NO: 7.

In some embodiments, the antigen binding domain comprises a heavy chain variable region comprising the amino acid sequence set forth in SEQ ID NO: 6, and a light chain variable region comprising the amino acid sequence set forth in SEQ ID NO: 7.

In some embodiments, the antigen binding domain is a single chain variable fragment (scFv).

In some embodiments, the scFv comprises the amino acid sequence set forth in SEQ ID NO: 8.

In some embodiments, the non-human primate is *Macaca fascicularis.*

In some embodiments, the non-human primate is *Macaca mulatta.*

The aAPC of any preceding claim, wherein the chimeric receptor molecule further comprises an intracellular domain.

In some embodiments, the intracellular domain comprises the intracellular domain of CD3 zeta.

In some embodiments, the intracellular domain comprises the amino acid sequence set forth in SEQ ID NO: 19.

In another aspect, the invention includes an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

- a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

In some embodiments, the intracellular domain comprises the intracellular domain of CD3 zeta.

In some embodiments, the intracellular domain comprises the amino acid sequence set forth in SEQ ID NO: 19.

In another aspect, the invention includes an artificial antigen presenting cell (aAPC) comprising a chimeric receptor molecule comprising an antigen binding domain having specificity for human CD3, and a transmembrane domain, wherein the antigen binding domain comprises:

a heavy chain variable region comprising three heavy chain complementarity determining regions (HCDRs), wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and a light chain variable region comprising three light chain complementarity determining regions (LCDRs), wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14.

In some embodiments, the antigen binding domain comprises a heavy chain variable region comprising the amino acid sequence set forth in SEQ ID NO: 15.

In some embodiments, the antigen binding domain comprises a light chain variable region comprising the amino acid sequence set forth in SEQ ID NO: 16.

In some embodiments, the antigen binding domain comprises a heavy chain variable region comprising the amino acid sequence set forth in SEQ ID NO: 15, and a light chain variable region comprising the amino acid sequence set forth in SEQ ID NO: 16.

In some embodiments, the antigen binding domain is a single chain variable fragment (scFv).

In some embodiments, the scFv comprises the amino acid sequence set forth in SEQ ID NO: 17.

In some embodiments, the chimeric receptor molecule further comprises a hinge domain.

In some embodiments, the hinge domain is a CD8 hinge domain.

In some embodiments, the hinge domain comprises the amino acid sequence set forth in SEQ ID NO: 21.

In some embodiments, the transmembrane domain is a CD8 transmembrane domain.

In some embodiments, the transmembrane domain comprises the amino acid sequence set forth in SEQ ID NO: 22.

In some embodiments, the chimeric receptor molecule comprises the amino acid sequence set forth in SEQ ID NO: 23 or 24.

In some embodiments, the chimeric receptor molecule is encoded by a nucleic acid comprising the nucleic acid sequence set forth in SEQ ID NO: 25 or 26.

In some embodiments, the chimeric receptor molecule consists of the amino acid sequence set forth in SEQ ID NO: 23 or 24.

In some embodiments, the chimeric receptor molecule is encoded by a nucleic acid consisting of the nucleic acid sequence set forth in SEQ ID NO: 25 or 26.

In some embodiments, the chimeric receptor molecule is constitutively expressed.

In some embodiments, the aAPC is an engineered K562 cell.

In some embodiments, the engineered K562 cell does not endogenously express one or more molecules selected from the group consisting of HLA class I, HLA class II, CD1d, CD16, CD64, CD83, CD86, 4-1BBL, OX40L, ICOSL, CD40L, PD-L1, PD-L2, B7-H3, and B7-H4.

In some embodiments, the aAPC further comprises an Fc receptor expressed at the cell surface.

In some embodiments, the Fc receptor is CD64.

In some embodiments, the aAPC further comprises a co-stimulatory molecule expressed at the cell surface.

In some embodiments, the co-stimulatory molecule is CD86.

In some embodiments, the aAPC further comprises an Fc receptor expressed at the cell surface, and a co-stimulatory molecule expressed at the cell surface.

In some embodiments, the Fc receptor is CD64, and the co-stimulatory molecule is CD86.

In some embodiments, the aAPC is loaded with an antibody, wherein the Fc fragment of the antibody is bound by the Fc receptor.

In some embodiments, the antibody has specificity for a molecule selected from the group consisting of CD3, CD28, PD-1, B7-H3, 4-1BB, OX40, ICOS, CD30, HLA-DR, MHCII, Toll Ligand Receptor and LFA-1.

In some embodiments, the aAPC further comprises a co-stimulatory ligand.

In some embodiments, the co-stimulatory ligand is selected from the group consisting of CD7, B7-1 (CD80), PD-L1, PD-L2, 4-1BBL, OX40L, ICOS-L, ICAM, CD30L, CD40, CD70, CD83, HLA-G, MICA, MICB, HVEM, lymphotoxin beta receptor, ILT3, ILT4, 3/TR6, and a ligand that specifically binds with B7-H3.

In some embodiments, the co-stimulatory ligand is 4-1BBL.

In some embodiments of the above aspects or any other aspect or embodiment of the invention, the aAPC expresses one or more cytokines selected from the group consisting of IL-2, IL-4, IL-5, IL-7, IL-10, IL-12, IL-13, IL-15, IL-17, IL-18, IL-21, IL-35, and TGF-β.

In some embodiments of the above aspects or any other aspect or embodiment of the invention, the aAPC expresses IL-7.

In some embodiments of the above aspects or any other aspect or embodiment of the invention, the aAPC expresses IL-15.

In some embodiments of the above aspects or any other aspect or embodiment of the invention, the aAPC expresses IL-7 and IL-15.

In some embodiments of the above aspects or any other aspect or embodiment of the invention, the aAPC expresses an IL-15R.

In some preferred embodiments, the IL-15R is IL-15Ra.

In some preferred embodiments, the cytokine is constitutively expressed.

In another aspect, the invention includes an artificial antigen presenting cell (aAPC) comprising:

a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell.

In another aspect, the invention includes an artificial antigen presenting cell (aAPC) comprising:

a chimeric receptor molecule comprising an antigen binding domain having specificity for human CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and a light chain variable region comprising three light chain complementarity determining regions (LCDRs), wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14;

CD64;

CD86; and 4-1BBL, and expresses IL-7 and IL-15, wherein the aAPC is an engineered K562 cell.

In some embodiments, the aAPC further comprises an IL-15R.

In some embodiments, the IL-15R is IL-15Ra.

In another aspect, the invention includes a composition comprising the aAPC of any preceding claim.

In some embodiments, the composition further comprises a pharmaceutically acceptable carrier.

In another aspect, the invention includes a method for stimulating and expanding a T cell, comprising contacting the T cell with the artificial presenting cell (aAPC) of any of the above aspects or any aspect or embodiment of the present disclosure.

In some embodiments, the T cell is an autologous T cell.

In some embodiments, the T cell is a human T cell.

In another aspect, the invention includes a method for stimulating and expanding a regulatory T cell (Treg), comprising contacting the Treg with the artificial presenting cell (aAPC) of any of the above aspects or any other aspect or embodiment of the current invention.

In some embodiments, the regulatory T cell is a human T cell.

In some embodiments, the regulatory T cell is a non-human primate T cell.

In some preferred embodiments, the non-human primate is *Macaca fascicularis*.

In some preferred embodiments, the non-human primate is *Macaca mulatta*.

In another aspect, the invention includes a method for stimulating and expanding a T cell, comprising contacting the T cell with an artificial antigen presenting cell (aAPC), wherein the aAPC comprises:

a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell.

In another aspect, the invention includes a method for stimulating and expanding a T cell, comprising contacting the T cell with an artificial antigen presenting cell (aAPC), wherein the aAPC comprises:

a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86;

4-1BBL;

IL-15Ra, and expresses IL-7 and IL-15, wherein the aAPC is an engineered K562 cell.

In another aspect, the invention includes a composition comprising membrane vesicles derived from an artificial antigen-presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell, and wherein the membrane vesicles are generated by the disruption of the aAPC.

In some embodiments, the disruption of the aAPC is accomplished by a method selected from the group consisting of mechanical homogenization, ultrasonic homogenization, pressure homogenization, temperature cycling, and nitrogen cavitation.

In some embodiments, the disruption of the aAPC is accomplished by nitrogen cavitation.

In another aspect, the invention includes a composition comprising membrane vesicles derived from an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5; and CD64; and CD86; and 4-1BBL; and IL-15Ra; and expresses IL-7 and IL-15, wherein the aAPC is an engineered K562 cell, and wherein the membrane vesicles are generated by the disruption of the aAPC.

In some embodiments, the disruption of the aAPC is accomplished by a method selected from the group consisting of mechanical homogenization, ultrasonic homogenization, pressure homogenization, temperature cycling, and nitrogen cavitation.

In some embodiments, the disruption of the aAPC is accomplished by nitrogen cavitation.

In another aspect, the invention includes a method for stimulating and expanding a T cell, comprising contacting the T cell with the composition of the above aspects or any other aspect or embodiment of the current invention.

In another aspect, the invention includes a method for stimulating and expanding a T cell, comprising contacting the T cell with a composition comprising membrane vesicles derived from an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell, and wherein the membrane vesicles are generated by the disruption of the aAPC.

In some embodiments, the disruption of the aAPC is accomplished by a method selected from the group consisting of mechanical homogenization, ultrasonic homogenization, pressure homogenization, temperature cycling, and nitrogen cavitation.

In some embodiments, the disruption of the aAPC is accomplished by nitrogen cavitation.

In another aspect, the invention includes a method for stimulating and expanding a T cell, comprising contacting the T cell with a composition comprising membrane vesicles derived from an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5; and CD64; and CD86; and 4-1BBL; and IL-15Ra; and expresses IL-7 and IL-15, wherein the aAPC is an engineered K562 cell, and wherein the membrane vesicles are generated by the disruption of the aAPC.

In some embodiments, the disruption of the aAPC is accomplished by a method selected from the group consisting of mechanical homogenization, ultrasonic homogenization, pressure homogenization, temperature cycling, and nitrogen cavitation.

In some embodiments, the disruption of the aAPC is accomplished by nitrogen cavitation.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A is a flowchart detailing the steps in producing OKT3 CAR-expressing K562 cells. FIG. 1B is a set of flow cytometry plots illustrating transduced K562 cells expressing OKT3 CAR (K562.OKT3). FIG. 1C is a set of flow cytometry plots illustrating transduced K562 cells expressing CD64, CD86, and OKT3 CAR (K562.64.86.OKT3). Results are in comparison to an untransduced control (UTD).

FIG. 12 is a chart illustrating the features of various generations of K562-based artificial APCs.

FIG. 27A shows the cell number at various time points during the 14-day culture. FIG. 27B shows flow cytometry staining of expanded Treg on day 14. CD4 vs CD8 (left) and CD25 vs Foxp3 (right).

FIG. 31A is a diagram of example nitrogen cavitation vessels (“bombs”). FIG. 31B illustrates an example workflow of the generation of aAPC membrane vesicles from aAPC cells using nitrogen cavitation.

FIG. 37 is a table illustrating the cell and media requirements for the stimulation of a number of T cells able to be stimulated with a 10 ml bottle of anti-CD3/anti-CD28 beads.

DETAILED DESCRIPTION

Definitions

Figure 1A:
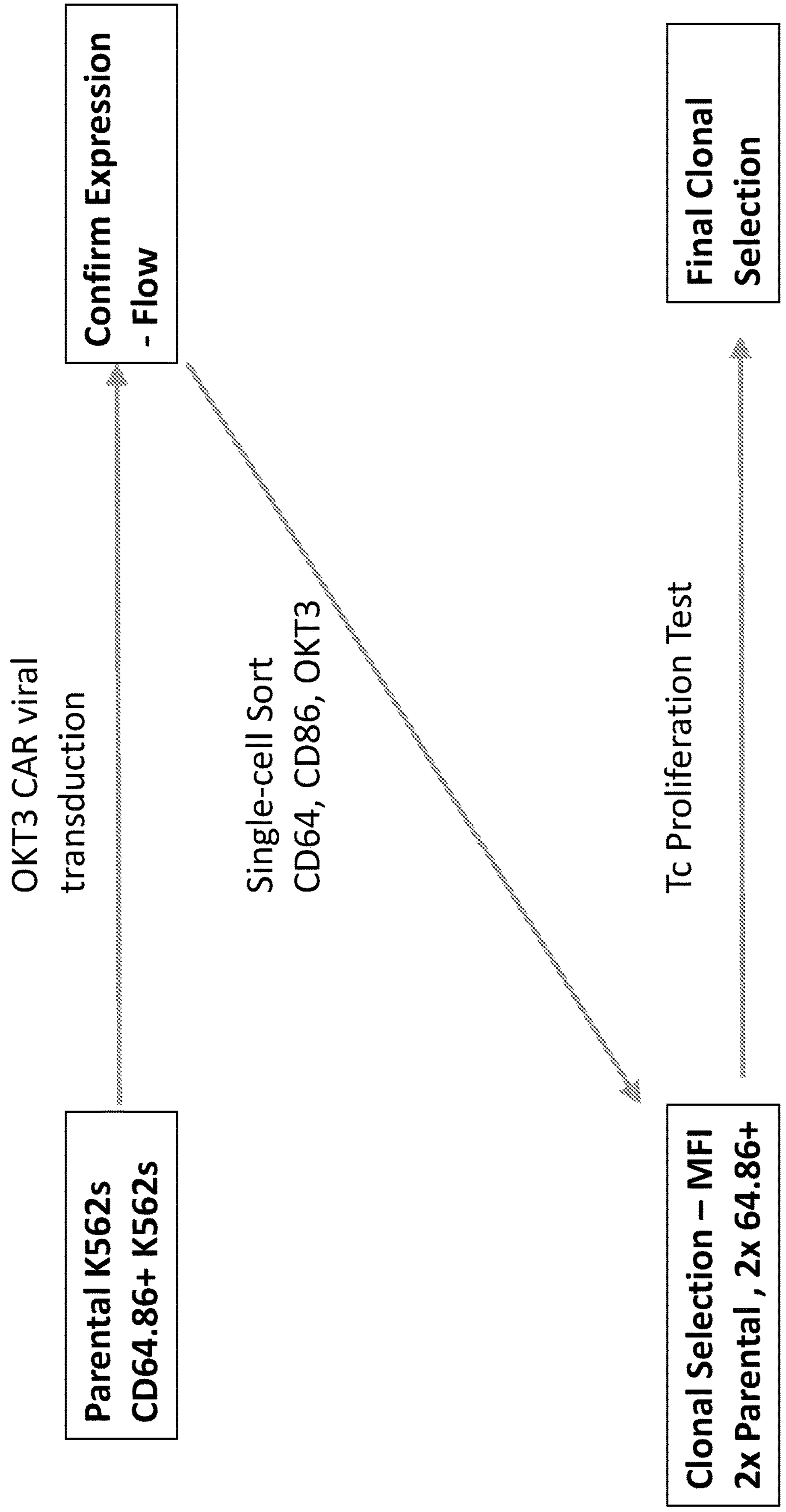
FIGS. 1A-1C illustrate the development of OKT3 CAR-expressing K562 artificial antigen presenting cells (aAPCs).

Unless otherwise defined, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab')2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Humanized" and "chimeric" forms of non-human (e.g., murine) antibodies are immunoglobulins, immunoglobulin chains or fragments thereof (such as Fv, Fab, Fab', $F(ab)_2$ or other antigen-binding subsequences of antibodies) which contain minimal sequence derived from non-human immunoglobulin. For the most part, humanized and chimeric antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized and chimeric antibodies can comprise residues which are found neither in the recipient antibody nor in the imported CDR or framework sequences. These modifications are made to further refine and optimize antibody performance. In general, the humanized and chimeric antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized and chimeric antibody optimally also will comprise at least a portion of an immunoglobulin constant region (Fc), typically that of a human immunoglobulin. The World Health Organization (WHO) International Nonproprietary Name (INN) Expert Group has defined requirements for non-human derived antibodies to be considered "humanized". According to guidelines, comparison of a candidate antibody to human sequences should be done through the International Immunogenetics Information System® (IMGT®) DomainGapAlign tool (www.imgt.org). This tool interrogates the IMGT® database of antibody germline variable region genes where the alignment score is made only against germline sequence variable region exons, thus omitting part of CDR3 and the J region from the analysis. For an antibody to be "humanized", in addition to being "closer to human than to other species", the top "hit" should be human and the identity to human sequences must be at least 85%, otherwise the antibody would be designated as "chimeric". For further details, see Jones et al., Nature, 321: 522-525, 1986; Reichmann et al., Nature, 332: 323-329, 1988; Presta, Curr. Op. Struct. Biol., 2: 593-596, 1992.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Co-stimulatory ligand", as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to CD86, 4-1BBL, BTLA and a Toll ligand receptor.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MEW Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Artificial Antigen Presenting Cells (aAPCs)

The present invention relates to the discovery that artificial antigen presenting cells (aAPCs) expressing a chimeric receptor (e.g. chimeric antigen receptor (CAR)) specific for CD3, can promote the activation and expansion of T cells.

In certain embodiments, the chimeric receptor is specific for human CD3 and/or non-human primate (e.g. *Macaca fascicularis* and/or *Macaca mulatta*) CD3. In certain embodiments, the aAPCs are based on the human erythromyeloid cell line K562. In certain embodiments, the aAPCs express stimulatory and/or co-stimulatory molecules, and/or secrete cytokines. The invention also provides methods and compositions for the expansion of T cell subsets, and especially regulatory T cells (Tregs) from both humans and non-human primates. Activation and expansion occurs more efficiently than commonly used methods, with the aAPCs endogenously expressing chimeric antigen receptors (CARs), and/or co-stimulatory molecules, and/or growth-supporting cytokines that would otherwise need to be provided from exogenous sources during preparation steps prior to use. The following provides description of the methods and various considerations necessary to practice the invention.

One aspect of the invention described herein relates to an aAPC engineered to comprise a chimeric receptor that binds specifically to CD3. The chimeric receptor comprises an antigen binding domain specific for CD3 and a transmembrane domain. The aAPC can optionally comprise an intracellular domain and/or hinge domain. In certain embodiments, the aAPC comprises at least one co-stimulatory molecule, and/or secretes at least one growth-promoting cytokine.

An antigen presenting cell (APC) is a cell which displays an antigen complexed with a major histocompatibility complex (WIC) on its surface. The T cell receptor (TCR) complex expressed by T cells will recognize the antigen/WIC complex, which results in the activation of the T cell. The role of an APC is to continuously process antigens and present them to T cells. Non-limiting examples of common, naturally occurring APCs include macrophages, B cells, and dendritic cells.

APCs are essential for the immune system to mount an effective adaptive immune response; the function of both cytotoxic and helper T cells requires the recognition of antigens presented by APCs. Antigen presentation determines the specificity of adaptive immunity and contributes to the immune response against intracellular and extracellular pathogens. APCs additionally play an important role in priming the immune system to recognize transformed cells, e.g., a malignant cell or tumor.

Antigen Binding Domain

The present invention encompasses artificial antigen presenting cells (aAPCs) comprising a chimeric receptor molecule comprising an antigen binding domain having specificity for CD3 (e.g. human CD3 and/or non-human primate CD3). The antigen binding domain is the extracellular region of the chimeric receptor that binds to a specific target antigen (e.g. CD3). In certain embodiments, the antigen biding domain is specific for human CD3 and non-human primate CD3 (e.g. CD3 from *Macaca fascicularis* and/or *Macaca mulatta*).

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof. In some embodiments, the antigen binding domain is selected from the group consisting of an antibody, an antigen binding fragment (Fab), and a single-chain variable fragment (scFv).

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker or spacer, which connects the N-terminus of the VH with the C-terminus of the VL, or the C-terminus of the VH with the N-terminus of the VL. In some embodiments, the antigen binding domain (e.g., CD3 binding domain) comprises an scFv having the configuration from N-terminus to C-terminus, VH-linker-VL. In some embodiments, the antigen binding domain (e.g., CD3 binding domain) comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as (GS)n, (GSGGS)n (SEQ ID NO: 27), (GGGS)n (SEQ ID NO: 28), and (GGGGS)n (SEQ ID NO: 29), where n represents an integer of at least 1. Exemplary linker sequences can comprise amino acid sequences including, without limitation, GGSG (SEQ ID NO: 30), GGSGG (SEQ ID NO: 31), GSGSG (SEQ ID NO: 32), GSGGG (SEQ ID NO: 33), GGGSG (SEQ ID NO: 34), GSSSG (SEQ ID NO: 35), GGGGS (SEQ ID NO: 36), GGGGSGGGGSGGGGS (SEQ ID NO: 37) and the like. Those of skill in the art would be able to select the appropriate linker sequence for use in the present invention. In one embodiment, an antigen binding domain (e.g., CD3 binding domain) of the present invention comprises a heavy chain variable region (VH) and a light chain variable region (VL), wherein the VH and VL is separated by the linker sequence having the amino acid sequence GGGGSGGGGSGGGGS (SEQ ID NO: 37), which may be encoded by the nucleic acid sequence ggtggcggtggctcgggcggtggtgggtcgggt ggcggcggatct (SEQ ID NO: 38).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some instances, the antigen binding domain may be derived from the same species in which the chimeric receptor will ultimately be used. For example, for use in humans, the antigen binding domain of the chimeric receptor may comprise a human antibody as described elsewhere herein, or a fragment thereof.

In certain embodiments, the antigen binding domain comprises a heavy chain variable region comprising three heavy chain complementarity determining regions (HCDRs) and a light chain variable region comprising three light chain complementarity determining regions (LCDRs).

In certain embodiments, the antigen binding domain comprises a HCDR comprising any one of the amino acid sequences set forth in SEQ ID NOs: 1-3 and/or a LCDR comprising any one of the amino acid sequences set forth in SEQ ID NOs: 4-6.

In certain embodiments, the antigen binding domain comprises a HCDR comprising any one of the amino acid sequences set forth in SEQ ID NOs: 11-13 and/or a LCDR comprising any one of the amino acid sequences set forth in SEQ ID NOs: 14-16.

In certain embodiments, the antigen binding domain comprises a heavy chain variable region comprising the amino acid sequence set forth in SEQ ID NO: 6 and/or a light chain variable region comprising the amino acid sequence set forth in SEQ ID NO: 7.

In certain embodiments, the antigen binding domain comprises a heavy chain variable region comprising the amino acid sequence set forth in SEQ ID NO: 15 and/or a light chain variable region comprising the amino acid sequence set forth in SEQ ID NO: 16.

In certain embodiments, the antigen binding domain is a single chain variable fragment (scFv). In certain embodiments, the scFv comprises the amino acid sequence set forth in SEQ ID NO: 8. In certain embodiments, the scFv comprises the amino acid sequence set forth in SEQ ID NO: 17.

The antigen binding domain may be operably linked to another domain of the chimeric receptor, such as the transmembrane domain or the intracellular domain, both described elsewhere herein. In one embodiment, a nucleic acid encoding the antigen binding domain is operably linked to a nucleic acid encoding a transmembrane domain.

The antigen binding domains described herein (e.g the scFv that binds CD3) can be combined with any of the transmembrane domains described herein, or any of the intracellular domains described herein.

Transmembrane Domain

The transmembrane domain of a subject chimeric receptor is a region that is capable of spanning the plasma membrane of the aAPC. The transmembrane domain is for insertion into a cell membrane, e.g. the aAPC cell membrane. In some embodiments, the transmembrane domain is interposed between the antigen binding domain and the intracellular domain of a chimeric receptor.

In certain embodiments, the transmembrane domain is naturally associated with one or more of the domains in the chimeric receptor. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane regions of particular use in this invention include, without limitation, transmembrane domains derived from (i.e. comprise at least the transmembrane region(s) of) the alpha, beta or zeta chain of the T-cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

In certain embodiments, the transmembrane domain is a CD8 transmembrane domain. In certain embodiments, the transmembrane domain comprises the amino acid sequence set forth in SEQ ID NO: 22.

The transmembrane domains described herein can be combined with any of the antigen binding domains described herein, any of the intracellular domains described herein, or any of the other domains described herein that may be included in a chimeric receptor.

In some embodiments, the transmembrane domain further comprises a hinge region. A subject chimeric receptor of the present invention may also include an hinge region. The hinge region of the chimeric receptor is a hydrophilic region which is located between the antigen binding domain and the transmembrane domain. In some embodiments, this domain facilitates proper protein folding for the chimeric receptor. The hinge region is an optional component for the chimeric receptor. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject chimeric receptor of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., Cancer Immunol. Res. (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

For example, hinge regions include glycine polymers (G)n, glycine-serine polymers (including, for example, (GS)n, (GSGGS)n (SEQ ID NO: 27) and (GGGS)n (SEQ ID NO: 38), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, Rev. Computational. Chem. (1992) 2: 73-142). Exemplary hinge regions can comprise amino acid sequences including, but not limited to, GGSG (SEQ ID NO: 30), GGSGG (SEQ ID NO: 31), GSGSG (SEQ ID NO: 32), GSGGG (SEQ ID NO: 33), GGGSG (SEQ ID NO: 34), GSSSG (SEQ ID NO: 35), and the like.

In some embodiments, the hinge region is an immunoglobulin heavy chain hinge region. Immunoglobulin hinge region amino acid sequences are known in the art; see, e.g., Tan et al., Proc. Natl. Acad. Sci. USA (1990) 87(1):162-166; and Huck et al., Nucleic Acids Res. (1986) 14(4): 1779-1789. As non-limiting examples, an immunoglobulin hinge region can include one of the following amino acid sequences: DKTHT (SEQ ID NO: 39); CPPC (SEQ ID NO: 40); CPEPKSCDTPPPCPR (SEQ ID NO: 41) (see, e.g., Glaser et al., J. Biol. Chem. (2005) 280:41494-41503); ELKTPLGDTTHT (SEQ ID NO: 42); KSCDKTHTCP (SEQ ID NO: 43); KCCVDCP (SEQ ID NO: 44); KYGPPCP (SEQ ID NO: 45); EPKSCDKTHTCPPCP (SEQ ID NO: 46) (human IgG1 hinge); ERKCCVECPPCP (SEQ ID NO: 47) (human IgG2 hinge); ELKTPLGDTTHTCPRCP (SEQ ID NO: 48) (human IgG3 hinge); SPNMVPHAHHAQ (SEQ ID NO: 49) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO: 50); see, e.g., Yan et al., J. Biol. Chem. (2012) 287: 5891-5897. In one embodiment, the hinge region can comprise an amino acid sequence derived from human CD8, or a variant thereof.

In certain embodiments, chimeric receptor comprises a CD8 hinge domain. In certain embodiments, the hinge domain comprises the amino acid sequence set forth in SEQ ID NO: 21.

Intracellular Domain

Certain aspects of the invention include an artificial antigen presenting cell (aAPC) comprising a chimeric receptor molecule comprising an antigen binding domain having specificity for CD3 (e.g. human and/or non-human primate CD3), a transmembrane domain, and an intracellular domain.

In certain embodiments, the intracellular domain comprises the intracellular domain of CD3 zeta. In certain embodiments, the intracellular domain comprises the amino acid sequence set forth in SEQ ID NO: 19.

TABLE 1

Amino Acid and Nucleotide Sequences

| Name | SEQ ID NO: | Type | Sequence |
|---|---|---|---|
| F12Q HCDR1 | 1 | Protein | GFTFNSYA |
| F12Q HCDR2 | 2 | Protein | IRSKYNNYAT |
| F12Q HCDR3 | 3 | Protein | VRHGNFGNSYVSWWAY |
| F12Q LCDR1 | 4 | Protein | TGAVTSGNY |
| F12Q LCDR2 | | Protein | GTK |
| F12Q LCDR3 | 5 | Protein | VLWYSNRWV |
| F12Q VH | 6 | Protein | EVQLVESGGGLVQPGGSLKLSCAASGFTFNSYAMNWVRQAPG KGLEWVARIRSKYNNYATYYADSVKGRFTISRDDSKNTAYLQ MNNLKTEDTAVYYCVRHGNFGNSYVSWWAYWGQGTLVTVS S |
| F112Q VL | 7 | Protein | QTVVTQEPSLTVSPGGTVTLTCGSSTGAVTSGNYPNWVQQKP GQAPRGLIGGTKFLAPGTPARFSGSLLGGKAALTLSGVQPEDE AEYYCVLWYSNRWVFGGGTKLTVL |

TABLE 1-continued

| Amino Acid and Nucleotide Sequences | | | |
|---|---|---|---|
| Name | SEQ ID NO: | Type | Sequence |
| F12Q scFv | 8 | Protein | EVQLVESGGGLVQPGGSLKLSCAASGFTFNSYAMNWVRQAPG KGLEWVARIRSKYNNYATYYADSVKGRFTISRDDSKNTAYLQ MNNLKTEDTAVYYCVRHGNFGNSYVSWWAYWGQGTLVTVS SGGGGSGGGGSGGGGSQTVVTQEPSLTVSPGGTVTLTCGSSTG AVTSGNYPNWVQQKPGQAPRGLIGGTKFLAPGTPARFSGSLLG GKAALTLSGVQPEDEAEYYCVLWYSNRWVFGGGTKLTVL |
| F12Q CAR | 9 | Protein | MALPVTALLLPLALLLHAARPGSEVQLVESGGGLVQPGGSLKL SCAASGFTFNSYAMNWVRQAPGKGLEWVARIRSKYNNYATY YADSVKGRFTISRDDSKNTAYLQMNNLKTEDTAVYYCVRHG NFGNSYVSWWAYWGQGTLVTVSSGGGGSGGGGSGGGGSQT VVTQEPSLTVSPGGTVTLTCGSSTGAVTSGNYPNWVQQKPGQ APRGLIGGTKFLAPGTPARFSGSLLGGKAALTLSGVQPEDEAE YYCVLWYSNRWVFGGGTKLTVLSGTTTPAPRPPTPAPTIASQP LSLRPEACRPAAGGAVHTRGLDFACDIYIWAPLAGTCGVLLLS LVITLYCRVKFSRSADAPAYQQGQNQLYNELNLGRREEYDVL DKRRGRDPEMGGKPRRKNPQEGLYNELQKDKMAEAYSEIGM KGERRRGKGHDGLYQGLSTATKDTYDALHMQALPPR |
| OKT3 HCDR1 | 10 | Protein | GYTFTRYT |
| OKT3 HCDR2 | 11 | Protein | INPSRGYT |
| OKT3 HCDR3 | 12 | Protein | ARYYDDHYCLDY |
| OKT3 LCDR1 | 13 | Protein | SSVSY |
| OKT3 LCDR2 | | Protein | DTS |
| OKT3 LCDR3 | 14 | Protein | QQWSSNPFT |
| OKT3 VH | 15 | Protein | QVQLQQSGAELARPGASVKMSCKASGYTFTRYTMHWVKQRP GQGLEWIGYINPSRGYTNYNQKFKDKATLTTDKSSSTAYMQL SSLTSEDSAVYYCARYYDDHYCLDYWGQGTTLTVSS |
| OKT3 VL | 16 | Protein | SIVLTQSPAIMSASPGEKVTMTCSASSSVSYMNWYQQKSGTSP KRWIYDTSKLASGVPAHFRGSGSGTSYSLTISGMEAEDAATYY CQQWSSNPFTFGSGTKLEIN |
| OKT3 scFv | 17 | Protein | QVQLQQSGAELARPGASVKMSCKASGYTFTRYTMHWVKQRP GQGLEWIGYINPSRGYTNYNQKFKDKATLTTDKSSSTAYMQL SSLTSEDSAVYYCARYYDDHYCLDYWGQGTTLTVSSSGGGGS GGGGSGGGGSIVLTQSPAIMSASPGEKVTMTCSASSSVSYMNW YQQKSGTSPKRWIYDTSKLASGVPAHFRGSGSGTSYSLTISGM EAEDAATYYCQQWSSNPFTFGSGTKLEINRAAA |
| OKT3 CAR | 18 | Protein | MALPVTALLLPLALLLHAARPQVQLQQSGAELARPGASVKMS CKASGYTFTRYTMHWVKQRPGQGLEWIGYINPSRGYTNYNQ KFKDKATLTTDKSSSTAYMQLSSLTSEDSAVYYCARYYDDHY CLDYWGQGTTLTVSSSGGGGSGGGGSGGGGSIVLTQSPAIMSA SPGEKVTMTCSASSSVSYMNWYQQKSGTSPKRWIYDTSKLAS GVPAHFRGSGSGTSYSLTISGMEAEDAATYYCQQWSSNPFTFG SGTKLEINRAAATTTPAPRPPTPAPTIASQPLSLRPEACRPAAGG AVHTRGLDFACDIYIWAPLAGTCGVLLLSLVITLYCKRGRK |
| F12Q CAR Intracellular Domain | 19 | Protein | RVKFSRSADAPAYQQGQNQLYNELNLGRREEYDVLDKRRGR DPEMGGKPRRKNPQEGLYNELQKDKMAEAYSEIGMKGERRR GKGHDGLYQGLSTATKDTYDALHMQALPPR |
| OKT3 CAR Intracellular Domain | 20 | Protein | TTTPAPRPPTPAPTIASQPLSLRPEACRPAAGGAVHTRGLDFAC DIYIWAPLAGTCGVLLLSLVITLYCKRGRK |
| CD8 Hinge Domain | 21 | Protein | TTTPAPRPPTPAPTIASQPLSLRPEACRPAAGGAVHTRGLDFAC D |
| CD8 TM Domain | 22 | Protein | IYIWAPLAGTCGVLLLSLVITLYC |
| F12Q chimeric receptor | 23 | Protein | MALPVTALLLPLALLLHAARPGSEVQLVESGGGLVQPGGSLKL SCAASGFTFNSYAMNWVRQAPGKGLEWVARIRSKYNNYATY YADSVKGRFTISRDDSKNTAYLQMNNLKTEDTAVYYCVRHG NFGNSYVSWWAYWGQGTLVTVSSGGGGSGGGGSGGGGSQT VVTQEPSLTVSPGGTVTLTCGSSTGAVTSGNYPNWVQQKPGQ |

TABLE 1-continued

Amino Acid and Nucleotide Sequences

| Name | SEQ ID NO: | Type | Sequence |
|---|---|---|---|
| | | | APRGLIGGTKFLAPGTPARFSGSLLGGKAALTLSGVQPEDEAE<br>YYCVLWYSNRWVFGGGTKLTVLSGTTTPAPRPPTPAPTIASQP<br>LSLRPEACRPAAGGAVHTRGLDFACDIYIWAPLAGTCGVLLLS<br>LVITLYCRVKFSRSADAPAYQQGQNQLYNELNLGRREEYDVL<br>DKRRGRDPEMGGKPRRKNPQEGLYNELQKDKMAEAYSEIGM<br>KGERRRGKGHDGLYQGLSTATKDTYDALHMQALPPR |
| OKT3 chimeric receptor | 24 | Protein | MALPVTALLLPLALLLHAARPQVQLQQSGAELARPGASVKMS<br>CKASGYTFTRYTMHWVKQRPGQGLEWIGYINPSRGYTNYNQ<br>KFKDKATLTTDKSSSTAYMQLSSLTSEDSAVYYCARYYDDHY<br>CLDYWGQGTTLTVSSSGGGGSGGGGSGGGGSIVLTQSPAIMSA<br>SPGEKVTMTCSASSSVSYMNWYQQKSGTSPKRWIYDTSKLAS<br>GVPAHFRGSGSGTSYSLTISGMEAEDAATYYCQQWSSNPFTFG<br>SGTKLEINRAAATTTPAPRPPTPAPTIASQPLSLRPEACRPAAGG<br>AVHTRGLDFACDIYIWAPLAGTCGVLLLSLVITLYCKRGRK |
| F12Q chimeric receptor | 25 | DNA | atggccttaccagtgaccgccttgctcctgccgctggccttgctgctccacgccgccaggcc<br>gggatccgaagtacaacttgtagagtctggagggggactcgtccagcccggtggctccctga<br>aactttcatgcgcagcaagcgggttcacgtttaactcttatgcaatgaattgggtccgacaa<br>gctccaggcaaaggacttgaatgggtcgccaggattcggagcaaatacaacaactacgcgac<br>atattatgctgatagtgtaaaaggacggttcacgatctcaagagacgattctaagaatacag<br>cgtatcttcaaatgaacaacttgaaaacagaagacaccgccgtttattattgcgtcagacat<br>ggcaactttggaaacagttacgtttcttggtgggcctactggggtcaagggacgcttgtcac<br>cgtcagctcaggaggcgggggatctggcggcggcggttcaggtggtggtggatctcagacag<br>tggtcacacaagagccatcacttaccgtatcccctgggggggactgtaacccttacctgcggg<br>tcctctacggggggctgttactagcggcaactatccaaactgggtgcaacaaaagcctggtca<br>agctccccgcgggctgatcggcggtactaagttccttgcgccgggcactcctgcaagatttt<br>caggttctcttcttgggggaaaagctgcattgactctcagtggtgtccagccggaggacgaa<br>gccgagtattactgtgtcctctggtattccaataggtgggtgttcgggggtggtactaaact<br>cactgtgctttccggaaccacgacgccagcgccgcgaccaccaacaccggcgcccaccatcg<br>cgtcgcagcccctgtccctgcgcccagaggcgtgccggccagcggcggggggcgcagtgcac<br>acgagggggctggacttcgcctgtgatatctacatctgggcgcccttggccgggacttgtgg<br>ggtccttctcctgtcactggttatcaccctttactgcagagtgaagttcagcaggagcgcag<br>acgcccccgcgtaccagcagggccagaaccagctctataacgagctcaatctaggacgaaga<br>gaggagtacgatgttttggacaagagacgtggccgggaccctgagatgggggggaaagccgag<br>aaggaagaaccctcaggaaggcctgtacaatgaactgcagaaagataagatggcggaggcct<br>acagtgagattgggatgaaaggcgagcgccggaggggcaaggggcacgatggcctttaccag<br>ggtctcagtacagccaccaaggacacctacgacgcccttcacatgcaggccctgccccctcg<br>ctaa |
| OKT3 chimeric receptor | 26 | DNA | Atggcactgcccgtgaccgccctcctcctgcccctcgcgctactcctgcacgccgccagacc<br>ccaggtgcagctgcagcagagtggcgctgagctggcccgccccggcgcctccgtgaagatgt<br>cctgcaaggctagtgggtataccttcaccaggtatactatgcactgggtgaagcagcgtccg<br>gggcaggggctcgagtggatcggctacatcaatccctcccgcggctacaccaattacaacca<br>gaagttcaaggataaggccacgctgaccacagacaagagtagctccacggcctacatgcagt<br>tatcaagtctgacctctgaggactccgctgtgtactattgtgcgaggtactacgacgaccac<br>tactgtctggactactggggccaaggcacaaccctgactgtaagttcctccggcggcggggg<br>gtccggcggcggcggctccggcgggggggggtagtatcgtgctgacacagagtcccgcaatca<br>tgtccgcaagccccggagagaaggtgaccatgacgtgtagtgcttccagctccgtgtcctat<br>atgaactggtaccagcagaaatccgggacttcccccaagagatggatctacgacaccagtaa<br>gctggccagtggcgtgcctgcacacttccgcggcagtggctccggcactagttacagtctca<br>ccatctccgggatggaagctgaggacgccgctacctactactgccagcagtggagctcgaac<br>ccattcaccttcggttcggggaccaagctcgagatcaacagggcggccgccaccacgacgcc<br>agcgccgcgaccaccaacaccggcgcccaccatcgcgtcgcagcccctgtccctgcgcccag<br>aggcgtgccggccagcggcgggggggcgcagtgcacacgagggggctggacttcgcctgtgat<br>atctacatctgggcgcccttggccgggacttgtggggtccttctcctgtcactggttatcac<br>cctttactgcaaacggggcagaaagtaataa |

In certain embodiments, the aAPC comprises a chimeric receptor molecule comprising the amino acid sequence set forth in SEQ ID NO: 23 or 24. In certain embodiments, the chimeric receptor molecule consists of the amino acid sequence set forth in SEQ ID NO: 23 or 24. In certain embodiments, the chimeric receptor molecule is encoded by a nucleic acid comprising or consisting of the nucleic acid sequence set forth in SEQ ID NO: 25 or 26. The chimeric receptor comprising the amino acid sequence set forth in SEQ ID NO:25 is also referred to herein as an F12Q chimeric receptor. The chimeric receptor comprising the amino acid sequence set forth in SEQ ID NO:26 is also referred to herein as an OKT3 chimeric receptor.

Tolerable variations of the chimeric receptor or its component parts (e.g. antigen binding domain (HCDRs, LCDRs, VH, VL, or scFv), transmembrane domain, hinge, or intracellular domain) will be known to those of skill in the art. For example, in some embodiments the CAR or any one of its components comprises an amino acid sequence that has at least at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to any of the amino acid sequences set forth in SEQ ID NOs:

1-26. For example, in some embodiments the chimeric receptor is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the nucleic acid sequence set forth in any one of SEQ ID NOs: 27-28.

In certain embodiments, the chimeric receptor molecule is constitutively expressed in the aAPC.

In certain embodiments, the aAPC does not endogenously express one or more molecules selected from the group consisting of HLA class I, HLA class II, CD1d, CD16, CD64, CD83, CD86, 4-1BBL, OX40L, ICOSL, CD40L, PD-L1, PD-L2, B7-H3, and B7-H4. In certain embodiments, the aAPC is an engineered K562 cell.

In certain embodiments, the aAPC further comprises an Fc receptor expressed on the cell surface. Various Fc receptors are known in the art, including, without limitation, CD64, CD32, CD16a, CD16b, CD23, and CD89. In certain embodiments, the Fc receptor is CD64.

In certain embodiments, the aAPC further comprises a co-stimulatory molecule expressed at the cell surface. Various co-stimulatory molecules are known in the art, including, without limitation, 4-1BB, OX40, PD-1, ICOS, lymphocyte function-associated antigen-1 (LFA-1), CD2, CD7, CD27, CD28, CD30, CD40, LIGHT, NKG2C, B7-H3, and a ligand that specifically binds with CD83. In certain embodiments, the co-stimulatory molecule is CD86.

In certain embodiments, the aAPC further comprises an Fc receptor expressed at the cell surface, and a co-stimulatory molecule expressed at the cell surface. In certain embodiments, the Fc receptor is CD64, and the co-stimulatory molecule is CD86.

In certain embodiments wherein the aAPC comprises an Fc receptor, the aAPC is loaded with an antibody, and the Fc fragment of the antibody is bound by the Fc receptor. In certain embodiments, the antibody has specificity for a molecule selected from the group consisting of CD3, CD28, PD-1, B7-H3, 4-1BB, OX40, ICOS, CD30, HLA-DR, MHCII, Toll Ligand Receptor and LFA-1.

In certain embodiments, the aAPC further comprises a co-stimulatory ligand. In certain embodiments, the co-stimulatory ligand is selected from the group consisting of CD7, B7-1 (CD80), PD-L1, PD-L2, 4-1BBL, OX40L, ICOS-L, ICAM, CD30L, CD40, CD70, CD83, HLA-G, MICA, MICB, HVEM, lymphotoxin beta receptor, ILT3, ILT4, 3/TR6, and a ligand that specifically binds with B7-H3. In certain embodiments, the co-stimulatory ligand is 4-1BBL. Other co-stimulatory ligands are encompassed in the invention, as would be understood by one skilled in the art armed with the teachings provided herein. Such ligands include, but are not limited to, a mutant, a variant, a fragment and a homolog of the natural ligands described previously.

These and other ligands are well-known in the art and have been well characterized as described in, e.g., Schwartz et al., 2001, Nature 410:604-608; Schwartz et al., 2002, Nature Immunol. 3:427-434; and Zhang et al., 2004, Immunity. 20:337-347. Using the extensive knowledge in the art concerning the ligand, the skilled artisan, armed with the teachings provided herein would appreciate that a mutant or variant of the ligand is encompassed in the invention and can be transduced into a cell using a lentivirus to produce the aAPC of the invention, and such mutants and variants are discussed more fully elsewhere herein. That is, the invention includes using a mutant or variant of a ligand of interest and methods of producing such mutants and variants are well-known in the art.

In certain embodiments, the aAPC expresses one or more cytokines selected from the group consisting of IL-2, IL-4, IL-5, IL-7, IL-10, IL-12, IL-13, IL-15, IL-17, IL-18, IL-21, IL-35, and TGF-β. In certain embodiments, the aAPC expresses IL-7. In certain embodiments, the aAPC expresses IL-15. In certain embodiments, aAPC expresses IL-7 and IL-15. In certain embodiments, the cytokine is constitutively expressed. As known in the art, in some cases, co-expression of IL-15Rα and IL-15 is important for the stable expression of IL15Ra/IL15. See, e.g., Hasan et al. *Clin. Exp. Immunol.* (2016) 186(2):249-265. Accordingly, in certain embodiments, the aAPC expresses IL-15 and/or IL-15Rα. In certain embodiments, the aAPC expresses IL-15 and IL-15Rα. In certain embodiments, the aAPC expresses a complex of IL-15 and IL-15Rα. See e.g. Guo et al. *Cytokine Growth Factor Rev* (2017) December; 38: 10-21 and Tamzalit et al. *PNAS* Jun. 10, 2014 111 (23) 8565-8570. In certain embodiments, the aAPC secretes a complex of IL-15/IL-15Rα. In certain embodiments, the aAPC expresses IL-21. In certain embodiments, the IL-21 has been modified to be membrane-bound.

In certain embodiments an aAPC of the present disclosure comprises an Fc receptor and a co-stimulatory ligand. In certain embodiments, the aAPC comprises the Fc receptor CD64 and the co-stimulatory ligand 4-1BBL.

In certain embodiments, an aAPC of the present disclosure comprises an Fc receptor, a co-stimulatory molecule, and a co-stimulatory ligand. In certain embodiments, the aAPC comprises the Fc receptor CD64, the co-stimulatory molecule CD86, and the co-stimulatory ligand 4-1BBL.

In certain embodiments, an aAPC of the present disclosure comprises an Fc receptor, a co-stimulatory ligand and an anti-CD3 chimeric receptor. In certain embodiments, the aAPC comprises the Fc receptor CD64, the co-stimulatory ligand 4-1BBL, and the OKT3 chimeric receptor. In certain embodiments, the aAPC comprises the Fc receptor CD64, the co-stimulatory ligand 4-1BBL, and the F12Q chimeric receptor.

In certain embodiments, an aAPC of the present disclosure comprises an Fc receptor, a co-stimulatory molecule, a co-stimulatory ligand and an anti-CD3 chimeric receptor. In certain embodiments, the aAPC comprises the Fc receptor CD64, the co-stimulatory molecule CD86, the co-stimulatory ligand 4-1BBL, and the OKT3 chimeric receptor. In certain embodiments, the aAPC comprises the Fc receptor CD64, the co-stimulatory molecule CD86, the co-stimulatory ligand 4-1BBL, and the F12Q chimeric receptor.

In certain embodiments, an aAPC of the present disclosure comprises an Fc receptor, a co-stimulatory ligand, an anti-CD3 chimeric receptor, and expresses IL-7, IL-15, and/or IL-15Rα. In certain embodiments, the aAPC comprises the Fc receptor CD64, the co-stimulatory ligand 4-1BBL, the OKT3 chimeric receptor, and expresses IL-7, IL-15, and/or IL-15Rα. In certain embodiments, the aAPC comprises the Fc receptor CD64, the co-stimulatory ligand 4-1BBL, the OKT3 chimeric receptor, and expresses IL-7 and IL-15. In certain embodiments, the aAPC comprises the Fc receptor CD64, the co-stimulatory ligand 4-1BBL, the OKT3 chimeric receptor, and expresses IL-7, IL-15, and IL-15Rα. In certain embodiments, the aAPC comprises the Fc receptor CD64, the co-stimulatory ligand 4-1BBL, the F12Q chimeric receptor, and expresses IL-7, IL-15, and/or IL-15Rα. In certain embodiments, the aAPC comprises the Fc receptor CD64, the co-stimulatory ligand 4-1BBL, the F12Q chimeric receptor, and expresses IL-7 and IL-15. In certain embodiments, the aAPC comprises the Fc receptor CD64, the co-stimulatory ligand 4-1BBL, the F12Q chimeric receptor, and expresses IL-7, IL-15, and IL-15Rα.

In certain embodiments, an aAPC of the present disclosure comprises an Fc receptor, a co-stimulatory ligand, a co-stimulatory molecule, an anti-CD3 chimeric receptor, and expresses IL-7, IL-15, and/or IL-15Rα. In certain embodiments, the aAPC comprises the Fc receptor CD64, the co-stimulatory ligand 4-1BBL, the co-stimulatory molecule CD86, the OKT3 chimeric receptor, and expresses IL-7, IL-15, and/or IL-15Rα. In certain embodiments, the aAPC comprises the Fc receptor CD64, the co-stimulatory ligand 4-1BBL, the co-stimulatory molecule CD86, the OKT3 chimeric receptor, and expresses IL-7 and IL-15. In certain embodiments, the aAPC comprises the Fc receptor CD64, the co-stimulatory ligand 4-1BBL, the co-stimulatory molecule CD86, the OKT3 chimeric receptor, and expresses IL-7, IL-15, and IL-15Rα. In certain embodiments, the aAPC comprises the Fc receptor CD64, the co-stimulatory ligand 4-1BBL, the co-stimulatory molecule CD86, the F12Q chimeric receptor, and expresses IL-7, IL-15, and/or IL-15Rα. In certain embodiments, the aAPC comprises the Fc receptor CD64, the co-stimulatory ligand 4-1BBL, the co-stimulatory molecule CD86, the F12Q chimeric receptor, and expresses IL-7 and IL-15. In certain embodiments, the aAPC comprises the Fc receptor CD64, the co-stimulatory ligand 4-1BBL, the co-stimulatory molecule CD86, the F12Q chimeric receptor, and expresses IL-7, IL-15, and IL-15Rα.

In certain embodiments, the aAPC comprises a K562 cell transduced to express at least one immune stimulatory and/or co-stimulatory ligand and/or secrete at least one immune stimulatory cytokine. While the data disclosed herein demonstrate that about six nucleic acids encoding about six different molecules transduced into a K562 cell were stably and highly expressed in long-term culture, there is nothing to suggest that this is a limit in the number or kinds of molecules that can be introduced into these cells. Instead, any molecule or ligand, whether stimulatory, co-stimulatory, cytokine, antigen, Fcγ receptor, and the like, can be introduced into these cells to produce an aAPC of the invention.

The skilled artisan would appreciate, based upon the disclosure provided herein, that numerous immunoregulatory molecules can be used to produce an almost limitless variety of aAPCs once armed with the teachings provided herein. That is, there is extensive knowledge in the art regarding the events and molecules involved in activation and induction of T cells, and treatises discussing T cell mediated immune responses, and the factors mediating them, are well-known in the art. More specifically, a primary signal, usually mediated via the T cell receptor/CD3 complex on a T cell, initiates the T cell activation process. Additionally, numerous co-stimulatory molecules present on the surface of a T cell are involved in regulating the transition from resting T cell to cell proliferation. Such co-stimulatory molecules, also referred to as "co-stimulators", which specifically bind with their respective ligands, include, but are not limited to, CD28 (which binds with B7-1 [CD80], B7-2 [CD86]), PD-1 (which binds with ligands PD-L1 and PD-L2), B7-H3, 4-1BB (binds the ligand 4-1BBL), OX40 (binds ligand OX40L), ICOS (binds ligand ICOS-L), and LFA (binds the ligand ICAM). Thus, the primary stimulatory signal mediates T cell stimulation, but the co-stimulatory signal is then required for T cell activation, as demonstrated by proliferation.

Thus, the aAPC of the invention encompasses a cell comprising a chimeric receptor that specifically binds with a TCR/CD3 complex such that a primary signal is transduced. Additionally, as would be appreciated by one skilled in the art, based upon the disclosure provided herein, the aAPC may further comprise at least one co-stimulatory ligand that specifically binds with at least one co-stimulatory molecule present on a T cell. Such co-stimulatory molecules include, but are not limited to, CD27, CD28, CD30, a ligand that specifically binds with CD83, 4-1BB, PD-1, OX40, ICOS, LFA-1, CD30L, NKG2C, B7-H3, MHC class I, BTLA, Toll ligand receptor and LIGHT.

In certain embodiments, the aAPC of the invention comprises at least one stimulatory ligand (e.g. a chimeric receptor) and at least one co-stimulatory ligand, such that the aAPC can stimulate and expand a T cell comprising a cognate binding partner stimulatory molecule that specifically binds with the stimulatory ligand on the aAPC such that interaction between the ligands on the aAPC and the corresponding molecules on the T cell mediate, among other things, T cell proliferation, and expansion as desired. One skilled in the art would appreciate that where the particular stimulatory and co-stimulatory molecules on a T cell of interest are known, an aAPC of the invention can be readily produced to expand that T cell. Conversely, where the stimulatory and co-stimulatory molecules on a T cell of interest are not known, a panel of aAPCs of the invention can be used to determine which molecules, and combinations thereof, can expand that T cell. Thus, the present invention provides tools for expansion of desirable T cells, as well as tools for elucidating the molecules on particular T cells that mediate T cell activation and proliferation.

In one aspect, the invention includes an artificial antigen presenting cell (aAPC) comprising a chimeric receptor molecule comprising an antigen binding domain having specificity for human CD3 and a non-human primate CD3, a transmembrane domain, and an intracellular domain. The antigen binding domain comprises a heavy chain variable region comprising three heavy chain complementarity determining regions (HCDRs) and a light chain variable region comprising three light chain complementarity determining regions (LCDRs). HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3. LCDR1 comprises the amino acid sequence set forth in SEQ ID NO: 4, LCDR2 comprises the amino acid sequence GTK, and LCDR3 comprises the amino acid sequence set forth in SEQ ID NO: 5. The aAPC also comprises CD64, CD86, 4-1BBL, IL-7, and IL-15, and the aAPC is an engineered K562 cell.

In another aspect, the invention includes an artificial antigen presenting cell (aAPC) comprising a chimeric receptor molecule comprising an antigen binding domain having specificity for human CD3, a transmembrane domain, and an intracellular domain. The antigen binding domain comprises a heavy chain variable region comprising three heavy chain complementarity determining regions (HCDRs) and a light chain variable region comprising three light chain complementarity determining regions (LCDRs). HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12. LCDR1 comprises the amino acid sequence set forth in SEQ ID NO: 13, LCDR2 comprises the amino acid sequence DTS, and LCDR3 comprises the amino acid sequence set forth in SEQ ID NO: 14. The aAPC also comprises CD64, CD86, 4-1BBL, IL-7, and IL-15, and the aAPC is an engineered K562 cell.

The skilled artisan would understand that the nucleic acids of the invention encompass an RNA or a DNA sequence encoding a protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook and Russell (2001, Molecular Cloning, A Laboratory Approach, Cold Spring Harbor Press, Cold Spring Harbor, N.Y.), and Ausubel et al. (2002, Current Protocols in Molecular Biology, John Wiley & Sons, NY). Procedures for the introduction of amino acid changes in a protein or polypeptide by altering the DNA sequence encoding the polypeptide are well known in the art and are also described in these, and other, treatises.

The present invention should also be construed to encompass "mutants," "derivatives," and "variants" of the peptides of the invention (or of the DNA encoding the same) which mutants, derivatives and variants are costimulatory ligands, cytokines, antigens (e.g., tumor cell, viral, and other antigens), which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of a costimulatory ligand, cytokine, antigen, and the like, of the present invention (e.g., expression by an aAPC where contacting the aAPC expressing the protein with a T cell, mediates proliferation of, or otherwise affects, the T cell).

Further, the invention encompasses an aAPC wherein the co-stimulatory ligand is a cognate binding partner that specifically binds with a co-stimulatory molecule, as well as where the ligand is an antibody that specifically binds with a costimulatory molecule, and any combination thereof; such that a single aAPC can comprise both nucleic acids encoding costimulatory ligands and/or antibodies specific for costimulatory molecules present on the T cell, and any combination thereof.

Additionally, the invention encompasses an aAPC transduced with a nucleic acid encoding at least one cytokine, at least one chemokine, or both. This is because the data disclosed elsewhere herein amply demonstrate that an aAPC transduced with a nucleic acid encoding an interleukin (e.g., IL-7, IL-15, and the like) stably expressed the interleukin. Moreover, using a LV vector comprising an internal ribosome entry site (IRES), the interleukin can be secreted from the aAPCs (e.g., a K562 transduced with a LV vector such as, but not limited to, pCLPS CD32-IRES-IL-7, -12, -15, -18, and -21). Other cytokines that can be expressed by aAPC include, but are not limited to, interferon-γ (IFNγ), tumor necrosis factor-α (TNFα), SLC, IL-2, IL-4, IL-23, IL-27 and the like. The invention further includes, but is not limited to, chemokine RANTES, MIP-1a, MIP-1b, SDF-1, eotaxin, and the like.

Thus, the invention encompasses a cytokine, including a full-length, fragment, homologue, variant or mutant of the cytokine. A cytokine includes a protein that is capable of affecting the biological function of another cell. A biological function affected by a cytokine can include, but is not limited to, cell growth, cell differentiation or cell death. Preferably, a cytokine of the present invention is capable of binding to a specific receptor on the surface of a cell, thereby affecting the biological function of a cell.

A preferred cytokine includes, among others, a hematopoietic growth factor, an interleukin, an interferon, an immunoglobulin superfamily molecule, a tumor necrosis factor family molecule and/or a chemokine. A more preferred cytokine of the invention includes a granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interferon alpha (IFNα), interferon beta (IFNβ), interferon gamma (IFNγ), and IGIF, among many others.

A chemokine, including a homologue, variant, mutant or fragment thereof, encompasses an alpha-chemokine or a beta-chemokine, including, but not limited to, a C5a, interleukin-8 (IL-8), monocyte chemotactic protein 1 alpha (MIP1α), monocyte chemotactic protein 1 beta (MIP1β), monocyte chemoattractant protein 1 (MCP-1), monocyte chemoattractant protein 3 (MCP-3), platelet activating factor (PAFR), N-formyl-methionyl-leucyl-[$^3$H]phenylalanine (FMLPR), leukotriene $B_4$ ($LTB_{4R}$), gastrin releasing peptide (GRP), RANTES, eotaxin, lymphotactin, IP10, 1-309, ENA78, GCP-2, NAP-2 and/or MGSA/gro. One skilled in the art would appreciate, once armed with the teachings provided herein, that the invention encompasses a chemokine and a cytokine, such as are well-known in the art, as well as any discovered in the future.

The skilled artisan would appreciate, once armed with the teachings provided herein, that the aAPC of the invention is not limited in any way to any particular antigen, cytokine, costimulatory ligand, antibody that specifically binds a costimulatory molecule, and the like. Rather, the invention encompasses an aAPC comprising numerous molecules, either all expressed under the control of a single promoter/regulatory sequence or under the control of more than one such sequence. Moreover, the invention encompasses administration of one or more aAPC of the invention where the various aAPCs encode different molecules. That is, the various molecules (e.g., costimulatory ligands, antigens, cytokines, and the like) can work in cis (i.e., in the same aAPC and/or encoded by the same contiguous nucleic acid or on separate nucleic acid molecules within the same aAPC) or in trans (i.e., the various molecules are expressed by different aAPCs).

In this way, as would be understood by one skilled in the art, based upon the disclosure provided herein, the dose and timing of administration of the aAPCs can be specifically tailored for each application. More specifically, where it is desirable to provide stimulation to a T cell using certain molecules expressed by an aAPC, or several aAPCs, followed by stimulation using another aAPC, or several aAPCs, expressing a different, even if overlapping, set of molecules, then a combination of cis and trans approaches can be utilized. In essence, the aAPCs of the invention, and the methods disclosed herein, provide an almost limitless number of variations and the invention is not limited in any way to any particular combination or approach. The skilled artisan, armed with the teachings provided herein and the knowledge available in the art, can readily determine the desired approach for each particular T cell.

The skilled artisan would understand, based upon the disclosure provided herein, that various combinations of molecules to be expressed in the aAPCs of the invention may be favored. While several of these combinations of molecules are indicated throughout the specification, including, but not limited to, the combinations exemplified in FIG. 12, the invention is in no way limited to these, or any other aAPC comprising any particular combination of molecules. Rather, one skilled in the art would appreciate, based on the teachings provided herein, that a wide variety of combinations of molecules can be transduced into a cell to produce the aAPC of the invention. The molecules encompass those known in the art, such as those discussed herein, as well as those molecules to be discovered in the future.

Methods

Provided in the invention are methods for stimulating and expanding a T cell (e.g. a regulatory T cell (Treg). The methods comprise contacting the T cell with any of the artificial presenting cells (aAPCs) disclosed herein.

As demonstrated elsewhere herein, contacting a T cell with an aAPC comprising a chimeric receptor specific for CD3, and optionally, a costimulatory ligand that specifically binds a cognate costimulatory molecule expressed on the T cell surface, stimulates the T cell and induces T cell proliferation such that large numbers of specific T cells can be readily produced. The aAPC expands the T cell "specifically" in that only the T cells expressing the particular costimulatory molecule are expanded by the aAPC. Thus, where the T cell to be expanded is present in a mixture of cells, some or most of which do not express the costimulatory molecule, only the T cell of interest will be induced to proliferate and expand in cell number. The T cell can be further purified using a wide variety of cell separation and purification techniques, such as those known in the art and/or described elsewhere herein.

As would be appreciated by the skilled artisan, based upon the disclosure provided herein, the T cell of interest need not be identified or isolated prior to expansion using the aAPC. This is because the aAPC is selective and will only expand the T cell(s) expressing the cognate costimulatory molecule.

Preferably, expansion of certain T cells is achieved by using several aAPCs or a single aAPC, expressing various molecules, including, but not limited to, an antigen, a cytokine, a costimulatory ligand, and an antibody ligand that specifically binds with the costimulatory molecule present on the T cell. As disclosed elsewhere herein, the aAPC can comprise a nucleic acid encoding CD32 and/or CD64 such that the CD32 and/or the CD64 expressed on the aAPC surface can be "loaded" with any antibody desired so long as they bind CD32 and/or CD64, which are Fcγ receptors. This makes the "off the shelf" aAPC easily tailored to stimulate any desired T cell.

The invention encompasses a method for specifically inducing proliferation of a T cell expressing a known co-stimulatory molecule. The method comprises contacting a population of T cells comprising at least one T cell expressing the known co-stimulatory molecule with an aAPC comprising a lentivirus encoding a ligand of the co-stimulatory molecule. As disclosed elsewhere herein, where an aAPC expresses at least one co-stimulatory ligand that specifically binds with a co-stimulatory molecule on a T cell, binding of the co-stimulatory molecule with its cognate co-stimulatory ligand induces proliferation of the T cell. Thus, the T cell of interest is induced to proliferate without having to first purify the cell from the population of cells. Also, this method provides a rapid assay for determining whether any cells in the population are expressing a particular costimulatory molecule of interest, since contacting the cells with the aAPC will induce proliferation and detection of the growing cells thereby identifying that a T cell expressing a costimulatory molecule of interest was present in the sample. In this way, any T cell of interest where at least one costimulatory molecule on the surface of the cell is known, can be expanded and isolated.

The invention includes a method for specifically expanding a T cell population subset. More particularly, the method comprises contacting a population of T cells comprising at least one T cell of a subset of interest with an aAPC capable of expanding that T cell, or at least an aAPC expressing at least one costimulatory ligand that specifically binds with a cognate costimulatory molecule on the surface of the T cell. As demonstrated previously elsewhere herein, binding of the co-stimulatory molecule with its binding partner co-stimulatory ligand induces proliferation of the T cell, thereby specifically expanding a T cell population subset. One skilled in the art would understand, based upon the disclosure provided herein, that T cell subsets include T helper ($T_{H1}$ and $T_{H2}$) CD4 expressing, cytotoxic T lymphocyte (CTL) (Tc1 or Tc2) T regulatory ($T_{REG}$), $T_{C/S}$, naïve, memory, central memory, effector memory, and γδT cells. Therefore, cell populations enriched for a particular T cell subset can be readily produced using the method of the invention.

In certain embodiments, the T cell to be expanded is an autologous T cell. In certain embodiments, the T cell is a human T cell. a regulatory T cell (Treg). In certain embodiments, the T cell is a non-human primate T cell. In certain embodiments, the non-human primate is *Macaca fascicularis*. the non-human primate is *Macaca mulatta*.

In one aspect, the invention provides a method for stimulating and expanding a human and/or non-human primate regulatory T cell (Treg). The method comprises contacting the Treg with an artificial antigen presenting cell (aAPC), wherein the aAPC comprises a chimeric receptor molecule comprising an antigen binding domain having specificity for human CD3 and a non-human primate CD3, a transmembrane domain, and an intracellular domain. The antigen binding domain comprises a heavy chain variable region comprising three heavy chain complementarity determining regions (HCDRs) and a light chain variable region comprising three light chain complementarity determining regions (LCDRs). HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3. LCDR1 comprises the amino acid sequence set forth in SEQ ID NO: 4, LCDR2 comprises the amino acid sequence GTK, and LCDR3 comprises the amino acid sequence set forth in SEQ ID NO: 5. The aAPC also comprises CD64, CD86, 4-1BBL, IL-7, and IL-15, and the aAPC is an engineered K562 cell.

In another aspect, the invention provides a method for stimulating and expanding a human and/or non-human T cell comprising contacting the cell with a composition comprising membrane vesicles generated from any of the artificial antigen-presenting cells (aAPCs) disclosed herein. In some embodiments, the aAPC membrane vesicles are generated by disrupting the aAPCs of the invention in such a way as to result in vesicles that retain functional cell-surface proteins expressed by the aAPCs, thereby retaining the vesicles ability to stimulate T cells and support expansion of T cell cultures. Such aAPC-derived vesicle compositions offer several advantages over co-culture with fully intact aAPC cells including, but not limited to, obviating the need for inactivation of the aAPCs through treatments such as cytotoxic chemicals, irradiation, or the like that may negatively affect the cultured T cells; optimizing the production of large-scale cultures due to the aAPC membrane vesicles not being metabolically active or requiring removal from the resulting population of expanded T cells; and enabling the more efficient transduction of the expanding T cells with viral vectors, including lentiviral vectors, due to significantly reduced interaction between the viral particles and the aAPC membrane vesicles.

In some embodiments, the aAPC membrane vesicles are generated by the disruption of the aAPC cells. A number of methods of cell disruption are well-known in the art including, but not limited to, mechanical homogenization such as with a handheld or motorized device, ultrasonic homogenization, pressure homogenization, temperature treatments comprising repeated cycles of freezing and thawing, osmotic lysis in hypotonic solutions, chemical lysis including the use of various detergents or solvents, nitrogen cavitation, among others. The skilled artisan would recognize which method of disruption would be most applicable to specific applications of generating membrane vesicles, including aAPC vesicles. In some embodiments, the method of disruption of aAPCs is nitrogen cavitation. This method involves placing a culture of aAPCs in a pressure vessel, often called a "bomb", and equilibrating the cells at high pressure under a nitrogen-rich atmosphere, thereby resulting in increased nitrogen and other gasses dissolved in the cytoplasm of the cells. The sudden exposure of the cells to atmospheric pressure results in nitrogen bubbles forming in the cytoplasm of the cells, which results in cell lysis. Pressure and release time can be varied to result in differing degrees of cell lysis and preservation of cellular, membrane, protein, and organelle structures. For example, relatively low pressures will disrupt the plasma membrane and endoplasmic reticulum only, while high pressures will result in the disruption of the nucleus and other organelles including lysosomes and mitochondria. In some embodiments, the pressure vessel, often called a "bomb", consists of a thick stainless steel or similar metal casing that is capable of withstanding high pressure, with an inlet for delivery of nitrogen gas from a tank and an outlet port with an adjustable discharge valve. The skilled artisan would recognize the precise conditions of nitrogen cavitation sufficient to produce the aAPC membrane vesicles of the invention and their use in the methods of the invention.

Pharmaceutical Compositions

The invention encompasses the preparation and use of pharmaceutical compositions comprising an aAPC of the invention as an active ingredient. In some embodiments, the composition comprises mixtures of membrane vesicles derived from the aAPCs of the invention. Such a pharmaceutical compositions may consist of the active ingredient alone (e.g. the cells of the invention and preparations thereof), as a combination of at least one active ingredient (e.g., an effective dose of an APC) in a form suitable for administration to a subject or use in activating and expanding T cells from a subject, or the pharmaceutical composition may comprise the active ingredient and one or more pharmaceutically acceptable carriers, one or more additional (active and/or inactive) ingredients, or some combination of these.

As used herein, the term "pharmaceutically acceptable carrier" means a chemical composition with which the active ingredient may be combined and which, following the combination, can be used to administer the active ingredient to a subject or activate and expand T cells from a subject. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates (e.g. monkeys, e.g. *Macaca fascicularis, Macaca mulatta*), cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the invention may be prepared, packaged, or sold in formulations suitable for oral, rectal, vaginal, parenteral, topical, pulmonary, intranasal, intra-lesional, buccal, ophthalmic, intravenous, intra-organ or another route of administration or use. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or for use in the activation and expansion of T cells from a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The aAPC or aAPC-derived membrane vesicles of the invention and/or T cells expanded using the aAPC or aAPC-derived membrane vesicles, can be administered to an animal, preferably a human. When the T cells expanded using an aAPC or aAPC-derived membrane vesicle of the invention are administered, the amount of cells administered can range from about 1 million cells to about 300 billion. Where the aAPCs or aAPC-derived membrane vesicles themselves are administered, either with or without T cells expanded thereby, they can be administered in an amount ranging from about 100,000 to about ten billion cells or vesicles wherein the cells and vesicles are infused into the animal, preferably, a human patient in need thereof. While the precise dosage administered will vary depending upon any number of factors, including but not limited to, the type of animal and type of disease state being treated, the age of the animal and the route of administration.

The aAPCs or aAPC-derived membrane vesicles may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

An aAPCs or aAPC-derived membrane vesicles (or cells expanded thereby) may be co-administered with the various other compounds (cytokines, chemotherapeutic and/or antiviral drugs, among many others). Alternatively, the compound(s) may be administered an hour, a day, a week, a month, or even more, in advance of the aAPCs or aAPC-derived membrane vesicles (or cells expanded thereby), or any permutation thereof. Further, the compound(s) may be administered an hour, a day, a week, or even more, after administration of aAPCs or aAPC-derived membrane vesicles (or cells expanded thereby), or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and the aAPCs or aAPC-derived membrane vesicles (or cells expanded thereby), and the like.

Further, it would be appreciated by one skilled in the art, based upon the disclosure provided herein, that where the aAPCs or aAPC-derived membrane vesicles are to be administered to a mammal, the cells are treated so that they are in a "state of no growth"; that is, the cells are incapable of dividing when administered to a mammal. As disclosed elsewhere herein, the cells can be irradiated to render them incapable of growth or division once administered into a mammal. Other methods, including haptenization (e.g., using dinitrophenyl and other compounds), are known in the art for rendering cells to be administered, especially to a human, incapable of growth, and these methods are not discussed further herein. Moreover, the safety of administration of aAPCs that have been rendered incapable of dividing in vivo has been established in Phase I clinical trials using aAPCs transfected with plasmid vectors encoding some of the molecules discussed herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Plasmids: pTRPE-CD86 was synthesized by Genscript, pTRPE-IL-15/IL-15 receptor alpha (IL-15/15Ra), pTRPE-IL-7 mcherry, pTRPE-F12Q (F12Q) and pTRPE-OKT3.8 (OKT3) were cloned in CCI.

Figure 14A:
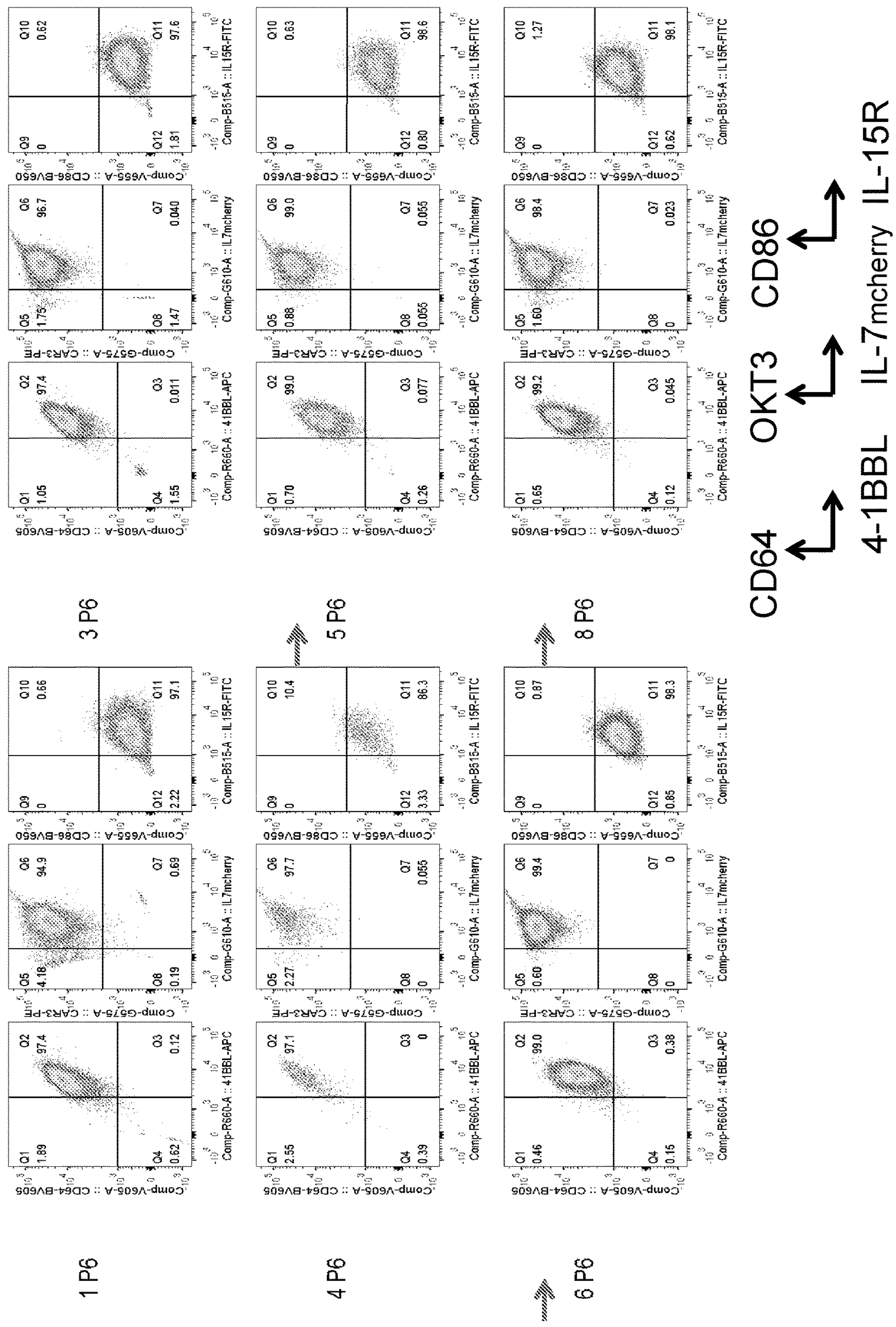
FIGS. 14A-14B illustrate the expression of transduced molecules in ten clones of APC4.1 cells (K562.64.41BBL.CAR3.IL7.IL15-15R) after six passages. Staining of parental K562 cells was used as a negative control. Arrows indicate high-expressing clones with minimal numbers of double-negative cells.
Figure 14B:
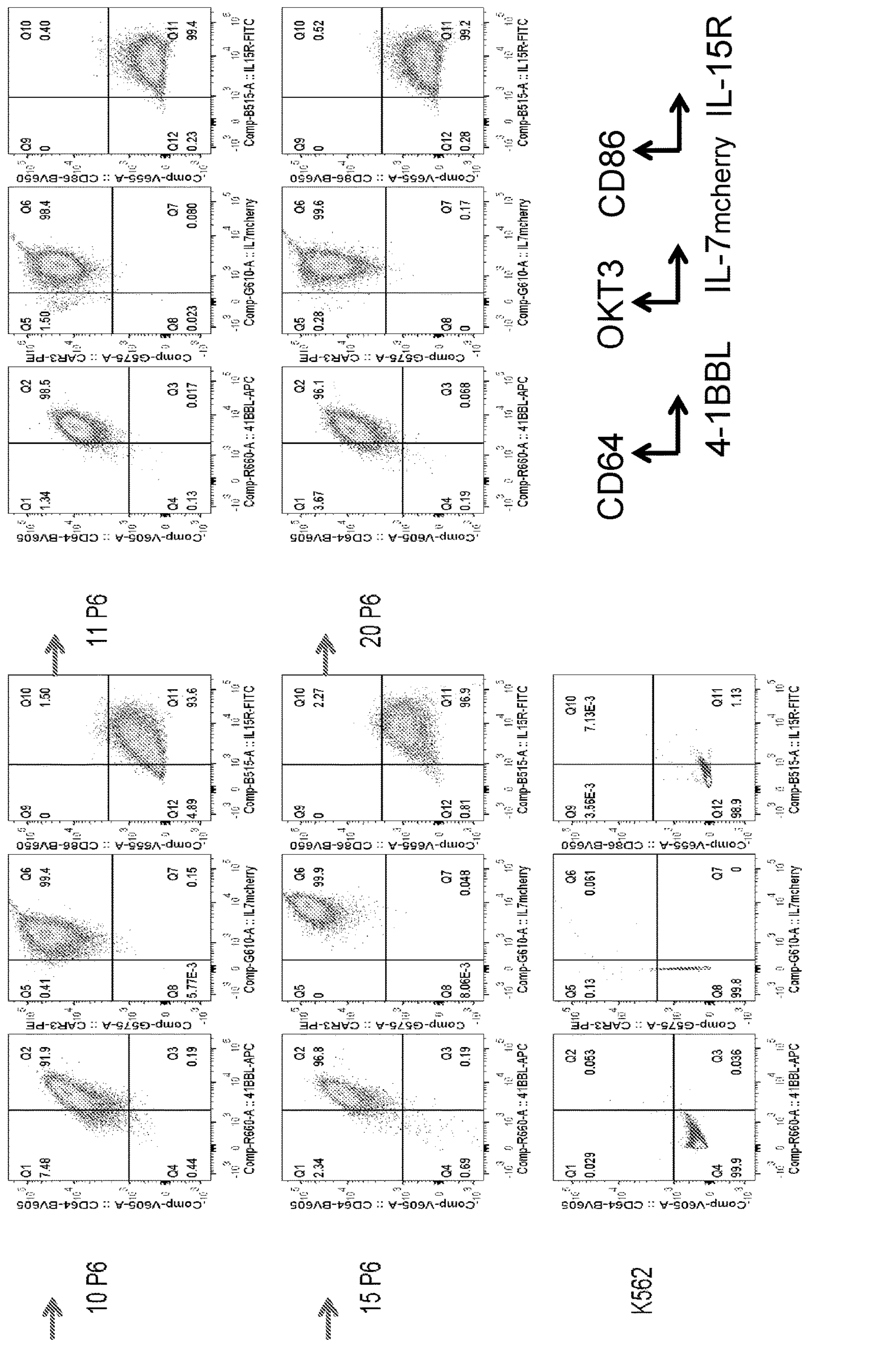
Figure 15A:
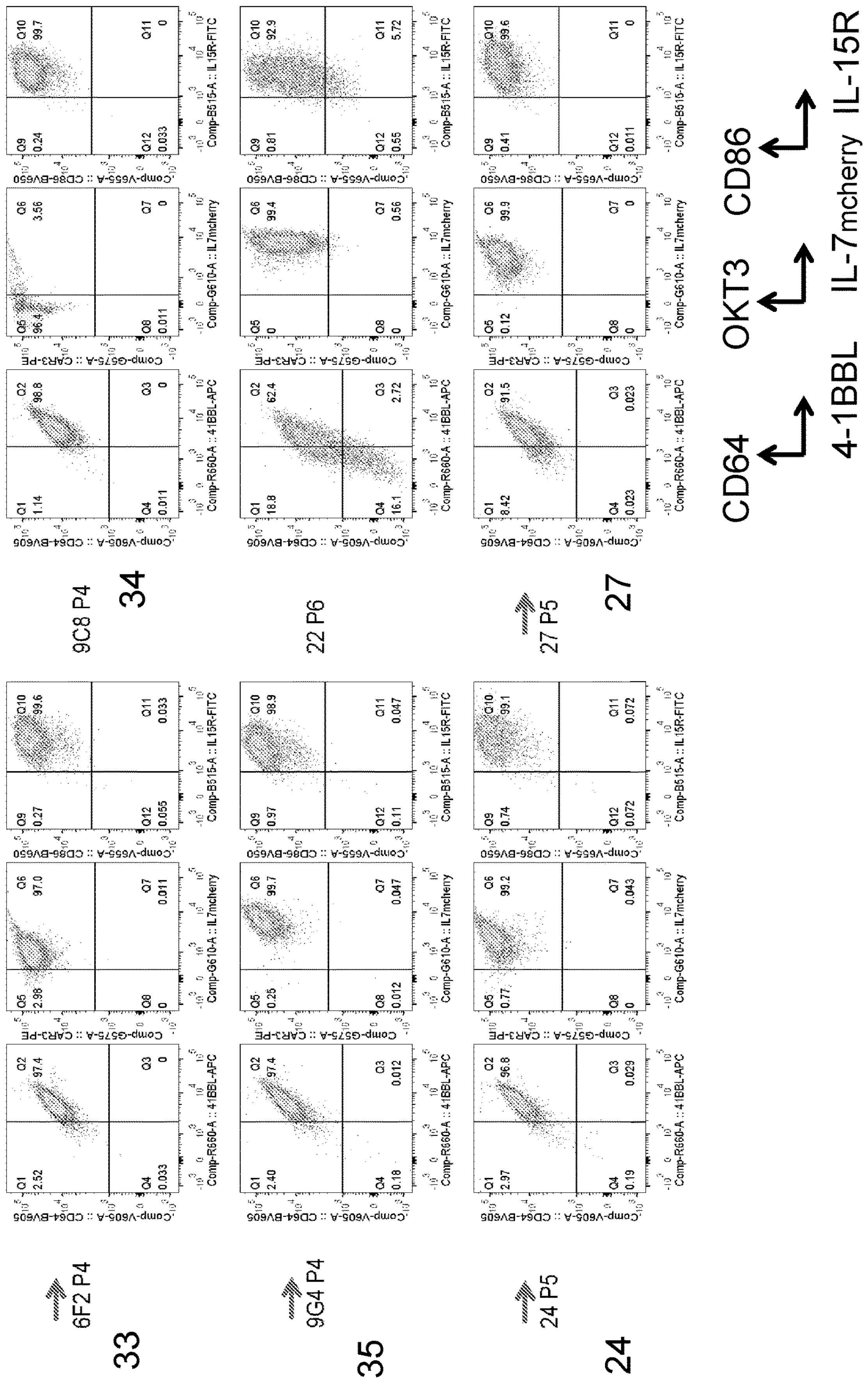
FIGS. 15A-15B illustrate the expression of transduced molecules in ten clones of APC5.1 cells (K562.64.41BBL.86.CAR3.IL7.IL15-15R) after four to six passages. Staining of parental K562 cells was used as a negative control. Arrows indicate high-expressing clones with minimal numbers of double-negative cells.
Figure 15B:
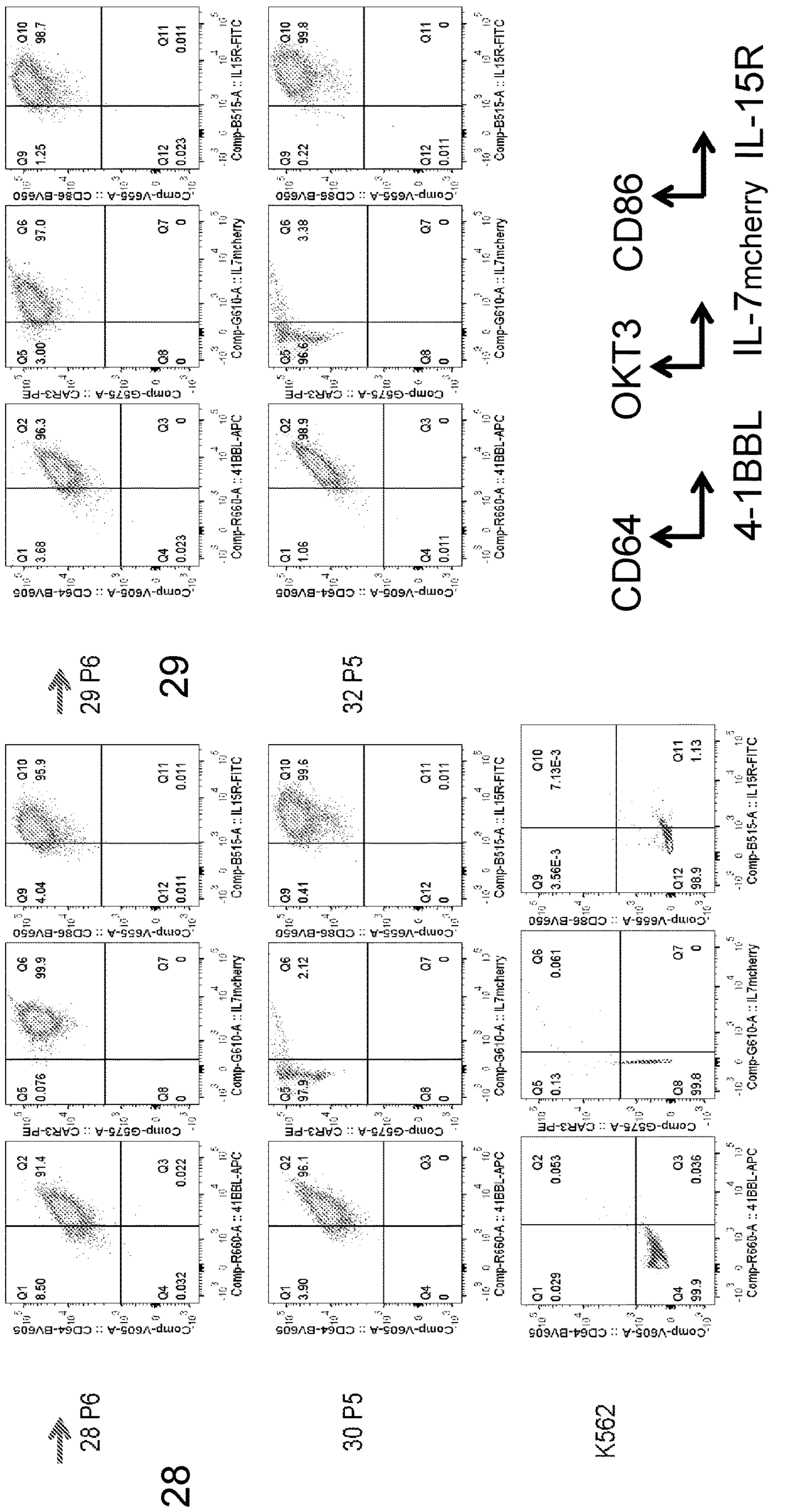
Figure 16:
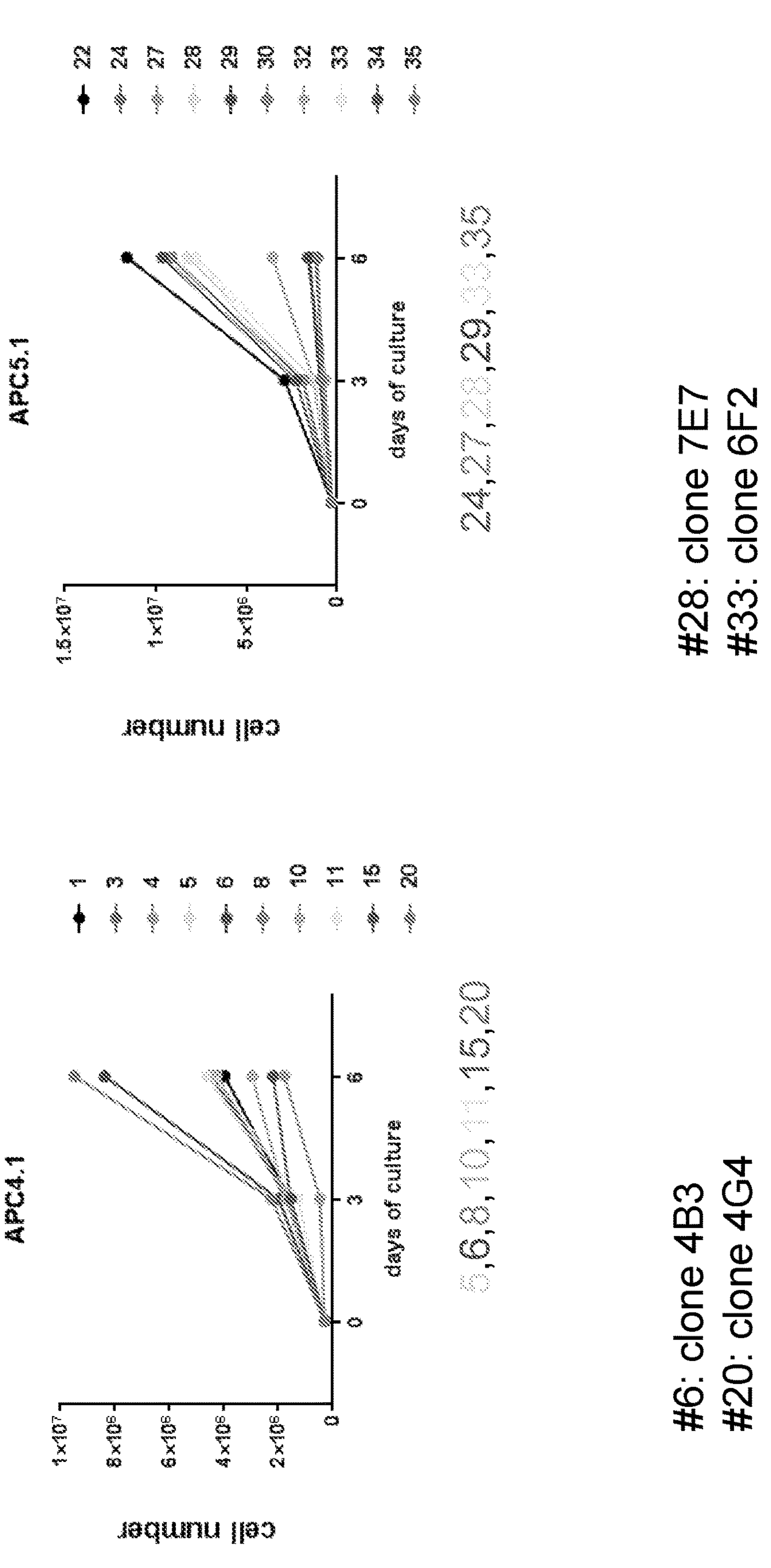
FIG. 16 illustrates the ability of the 10 APC4.1 (left) and APC5.1 (right) clones to stimulate the expansion of human T cells. Each clone was co-cultured with normal human donor T cells for six days, and T cell expansion was assessed at the indicated time points by determining the total number of cells per well.
Figure 17:
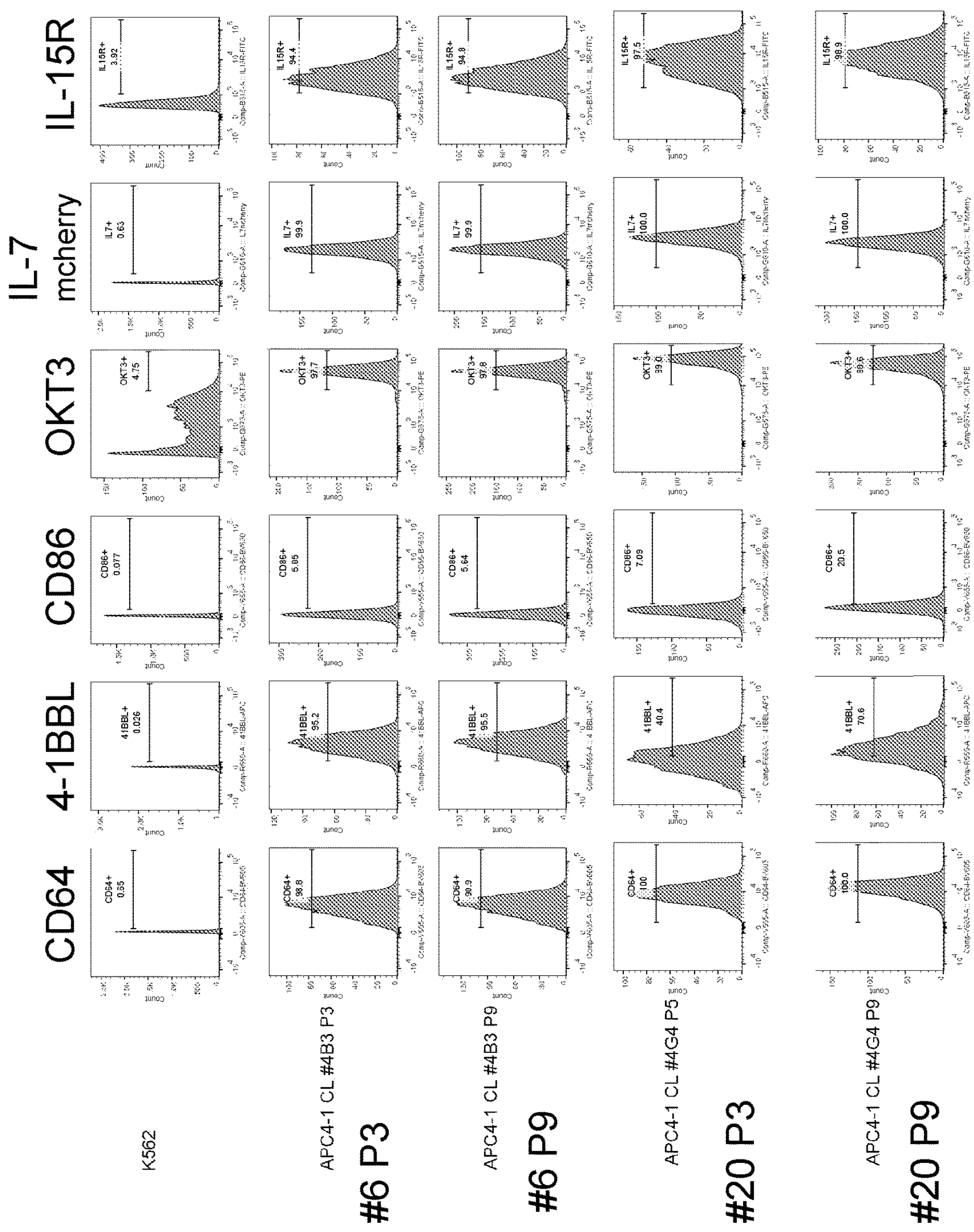
FIG. 17 illustrates the stability of the expression of transgenes in two APC4.1 clones. Expression of each transgene (columns) was assessed in each clone after 3 and 9 passages in vitro. For comparison, parental K562 cells were used as a negative control (top row).
Figure 18:
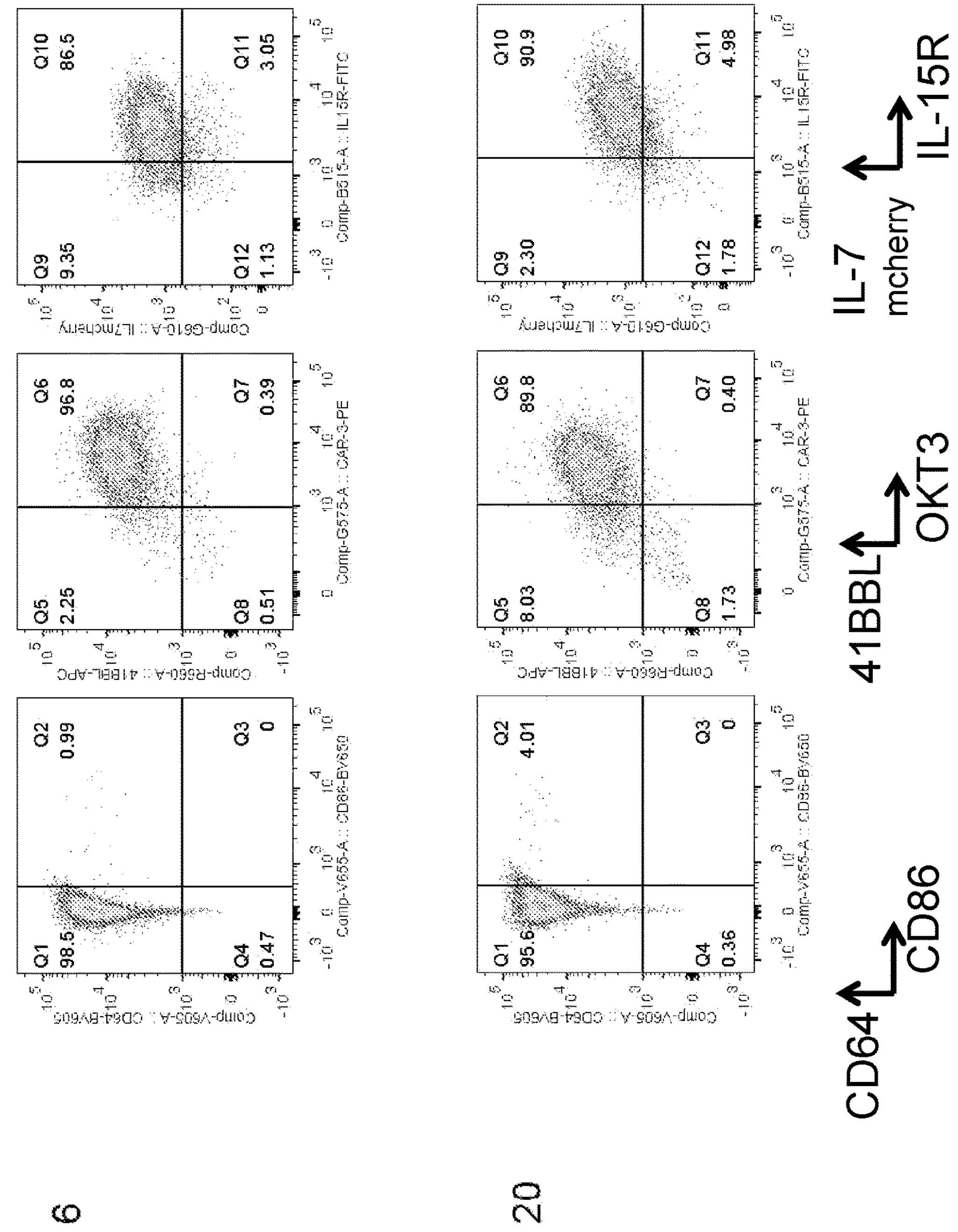
FIG. 18 illustrates the transgene expression of the APC4.1 clones used in FIG. 17 at an earlier passage. Cells from clone 6 (top row) and clone 20 (bottom row) were stained after 3 passages for the indicated proteins.
Figure 19:
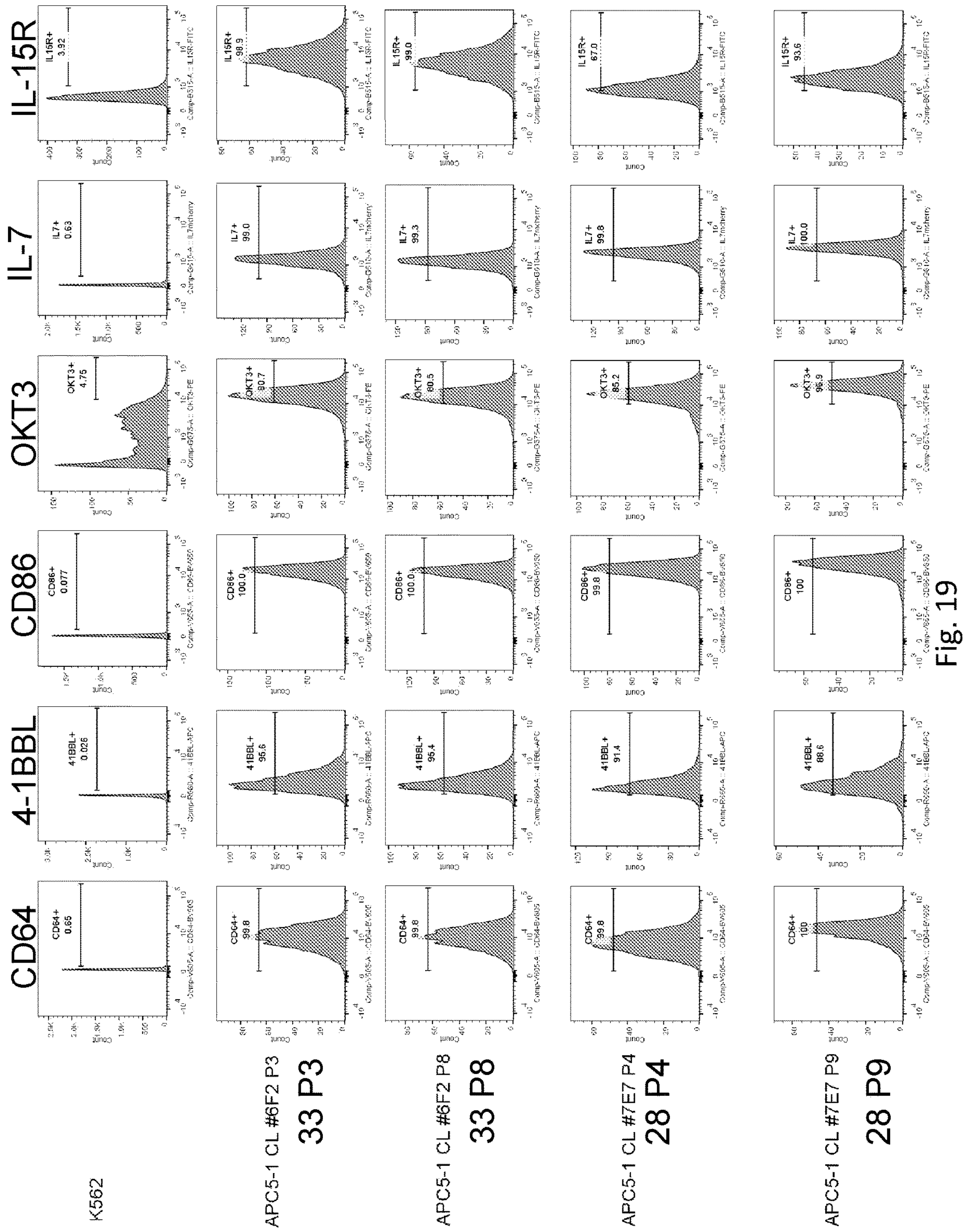
FIG. 19 illustrates the stability of transgene expression in two APC5.1 clones. Expression of each transgene (columns) was assessed in each clone after three, four, and eight passages in vitro. For comparison, parental K562 cells were stained with the same panel of antibodies as a negative control (top row).

Generation of aAPC cell lines: K562 cells that express Fc receptor CD64 and 4-1BB ligand (4-1BBL) were transduced to express the CD86 construct, which resulted in the K562.64.4-1BBL.86 cell line (APC3.0). Further, K562.64.4-1BBL.86 (APC3.0) and K562.64.4-1BBL (APC2.0) cell lines were transduced to express the anti-CD3 OKT3 construct, resulting in the K562.64.41BBL.OKT3 (APC2.1) and K562-64.86.4-1BBL.OKT3 (APC3.1) cell lines respectively. Then APC2.1 and APC3.1 were transduced to express both IL-7 mcherry and IL-15/15R constructs resulting in the K562.64.4-1BBL.OKT3.IL-7mcherry.IL-15/15R (APC4.1) cell line and K562-65.4-1BBL.86.OKT3IL-7mcherry.IL-15/15R (APC5.1) cell line, respectively. Expression of the CD64, 4-1BBL, CD86, OKT3, IL-7, IL-15/15R surface proteins was verified by flow cytometry. Various clones of the newly-created APC4.1 and APC5.1 were established by single-cell sorting followed by expansion in vitro. Particularly, several clones of APC4.1 that maintained expression of CD64, 4-1BBL, OKT3, IL-7, IL-15R were then selected for further culture (FIGS. 14A-14B). Likewise, several clones of APC5.1 were similarly selected for further expansion and use, based on additional CD86 expression (FIGS. 15A-15B). Based on the proliferation, two clones of APC4.1 and APC5.1 were selected for further testing (FIG. 16). The selected clones of APC4.1 clone 6 (4B3) and 20 (4G4) were then checked at different passages for maintaining the transgene expression (FIGS. 17-18). APC5.1 clone 33 (6F2) showed stable transgene expression over time (FIG. 19). Selected clones were plated at a cell density of $5\times10^5$ cells per mL overnight for IL-7, IL-15 and IL-15Rα detection. ELISA assay showed APC4.1 clone 20 can secrete 4 ng/mL IL-7 and 7.5 ng/mL IL-15, and APC5.1 clone 33 can secrete 3 ng/mL IL-7 and 8 ng/mL IL-15. K562.64.86 cells were transduced with the anti-CD3 F12Q construct to create K562.F12Q.64.

Antibodies for flow cytometry: CD64-PE-cy7 (Biolegend, Cat #305022), 41BBL-APC (Cat #311506), CD86-BV650 (Biolegend, Cat #305428) and IL-15Rα-FITC (eBioscience, Cat #11-7159-42) were purchased for flow cytometry. Biotin-goat-anti-mouse IgG Fab (Jackson Immuno Research, Cat #115-065-072) and streptavidin-PE (BD, Cat #554061) were used for detection of anti-CD3 OKT3. Biotinylated Human CD3 epsilon Protein (AcroBiosystems Cat #CDE-H82E1) and streptavidin-PE were used for detection of anti CD3 F12Q.

Irradiation of aAPCs: AAPCs were expanded in RPMI 1640+5% human serum and cells were resuspended to $2.5\times10^7$ cells per mL and irradiated under 100 Gy using irradiator XRAD 320iX.

T cell expansion in vitro: Cryopreserved elutriated lymphocytes or leukapheresis of multiple myeloma patients (n=3) were thawed and CD4 and CD8 T cells were selected using CD4 and CD8 microbeads (Miltenyi Biotec, Cat #130-045-101 and 130-045-201). T cells were stimulated with CTS CD3/CD28 Dynabeads (Thermo Fisher, Cat #40203D) at a T to beads ratio of 1:3 or with soluble anti-CD3/CD28 Cloudz (Quad Technologies, per manufacturer's protocol) or with different aAPCs at a T to irradiated aAPC ratio of 1:1 with different culture media for 7 days. $2\times10^6$ T cells were plated in G-REX 24-well plates (Wilson Wolf, Cat #80192M) in different culture media containing cytokines 5 ng/mL IL-7 (Miltenyi Biotec, Cat #170-076-111) and IL-15 (Miltenyi Biotec, Cat #170-076-114) except for T cells stimulation with APC4.1 and APC5.1. Several culture media formulations have been used to compare the T cell expansion. OpTmizer (Thermo Fisher, Cat #A1048501) or 1B2H with and without 5% CTS Immune Cell SR (Thermo Fisher, Cat #A2596101) were compared to X-VIVO15 (Lonza, Cat #04-744Q)-based modified medium, which was described previously (cite?). The cell number and volume were measured by Coulter Counter Multisizer 4. Supernatants were collected for detection of IL-7 and IL-15 by ELISA in the media.

Example 1: Creation of aAPC Cells Expressing an OKT3-Based CAR

Figure 1C:
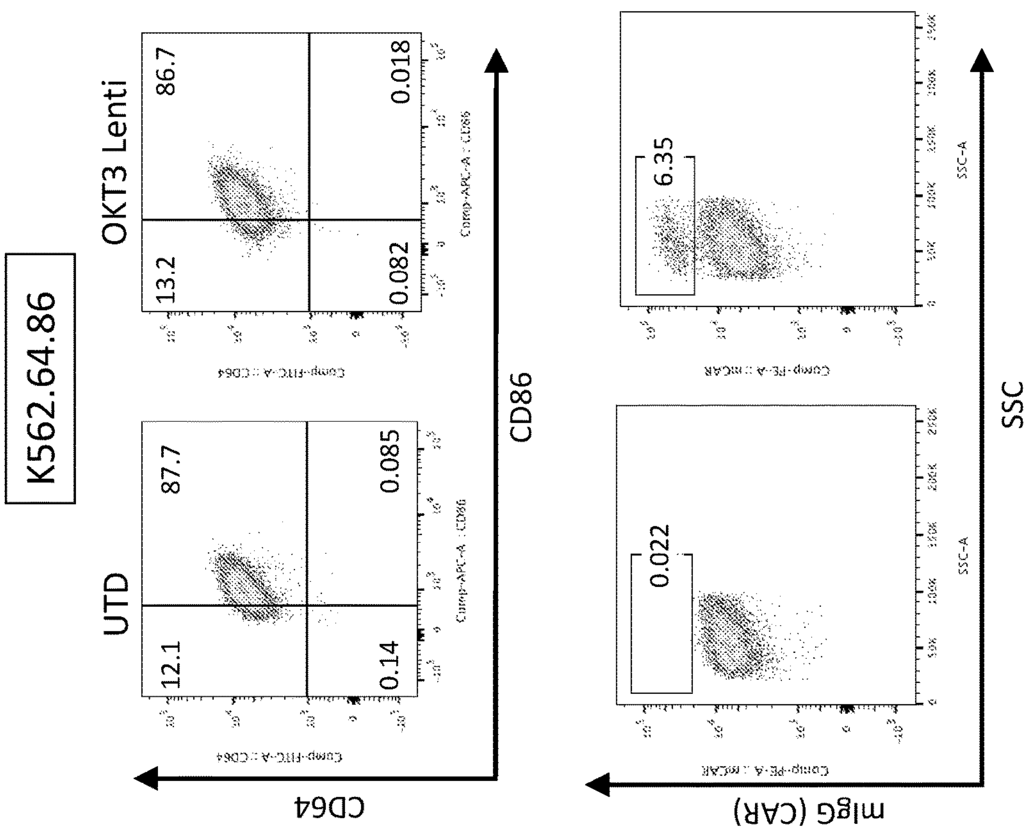
Figure 1B:
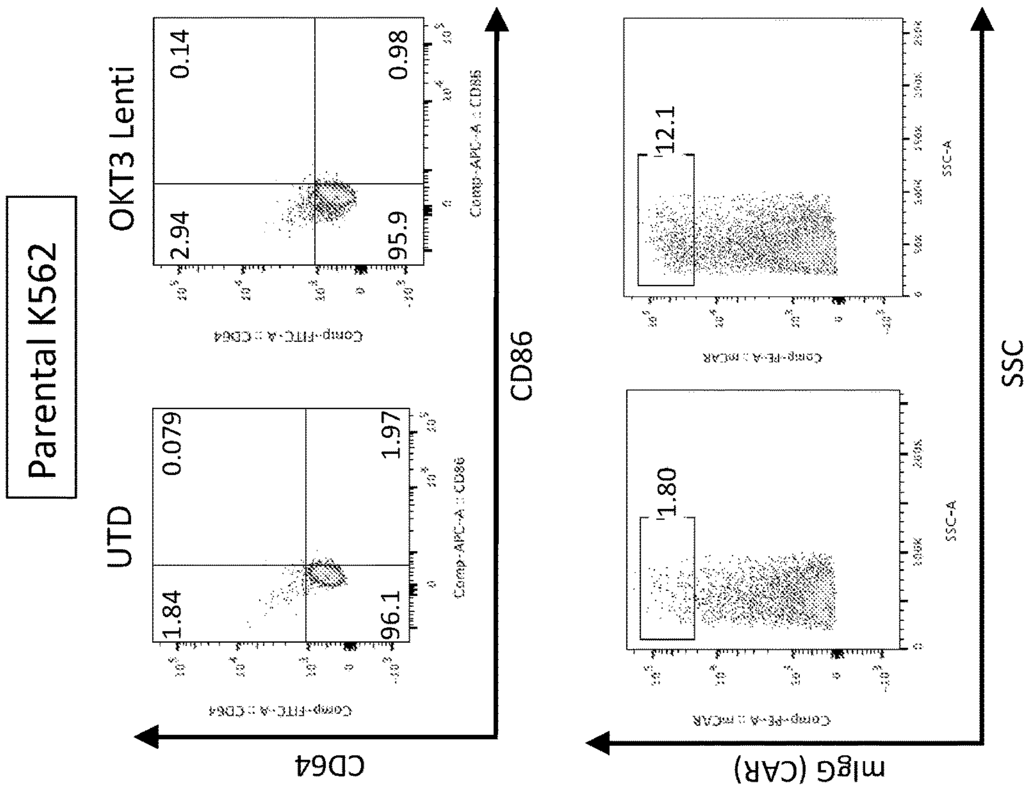

In order to develop artificial APCs capable of expanding human T cells in vitro without the need for tedious preparation steps involving coating cells with exogenous antibodies, a series of studies were undertaken to create a K562-based APC expressing a membrane-bound, scFv version of the anti-human CD3 antibody OKT3. A flowchart of the development steps is illustrated in FIG. 1A. K562 parental cells, as well as K562 cells that express the co-stimulatory protein CD86 and the Fc receptor CD64, were transduced to express the OKT-CAR construct, resulting in K562.OKT3 and K562.64.86.OKT3 cell lines, respectively. Expression of the OKT3 CAR, CD64, and CD86 surface proteins was verified by flow cytometry (FIGS. 1B-1C). Results are in comparison to an untransduced control (UTD).

Figure 2:
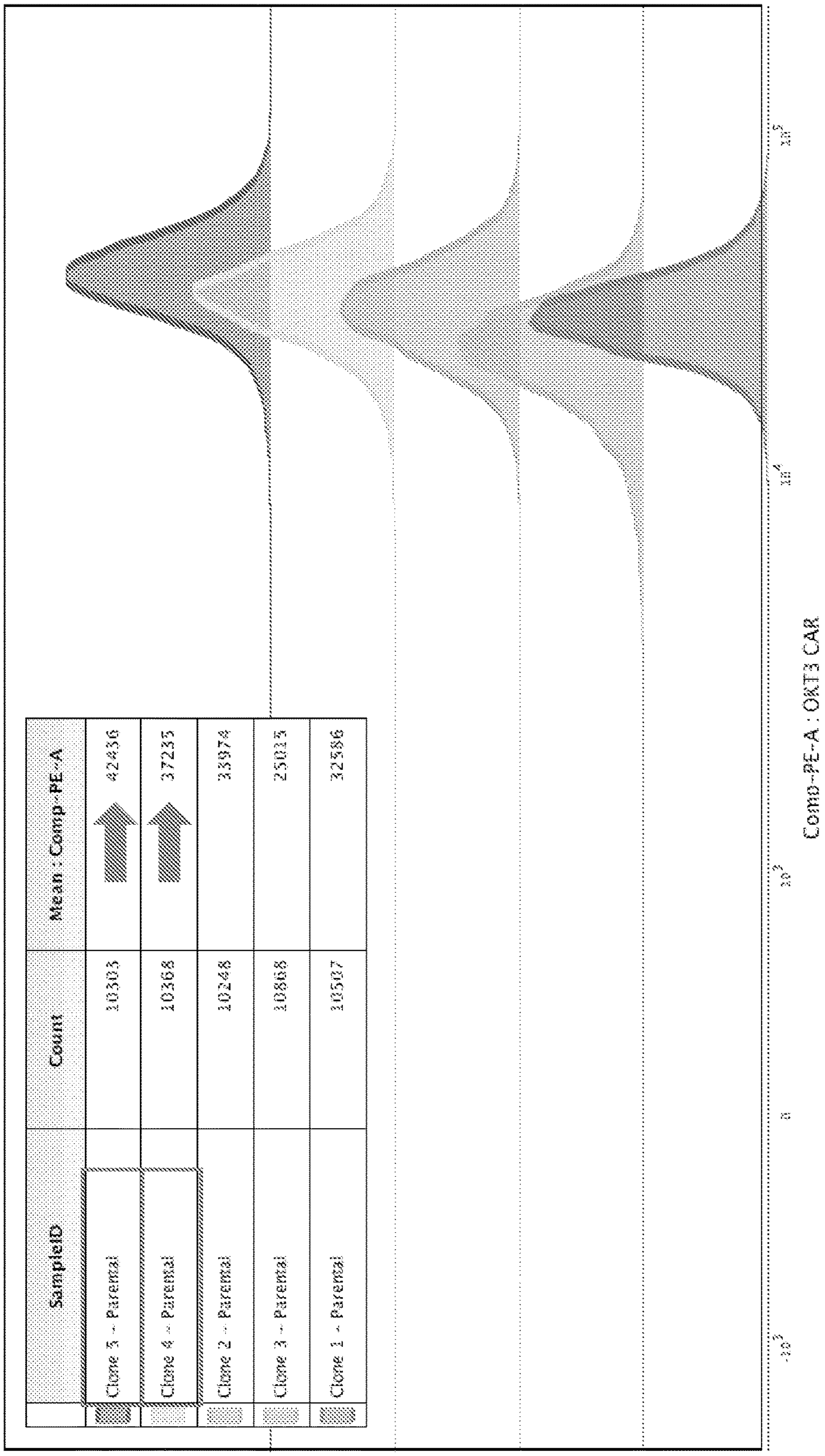
FIG. 2 illustrates the expression of the OKT3 CAR construct in various clones of the newly created K562.OKT3 cell line. Histograms indicate the level of expression of the CD3 CAR construct as assessed by flow cytometry. The legend indicates the mean fluorescence intensity (MFI) of each clone in the channel corresponding to CD3 CAR staining. Boxes and arrows indicate that the clones demonstrating the highest MFI (Clones 4 and 5) were selected for further development.
Figure 3:
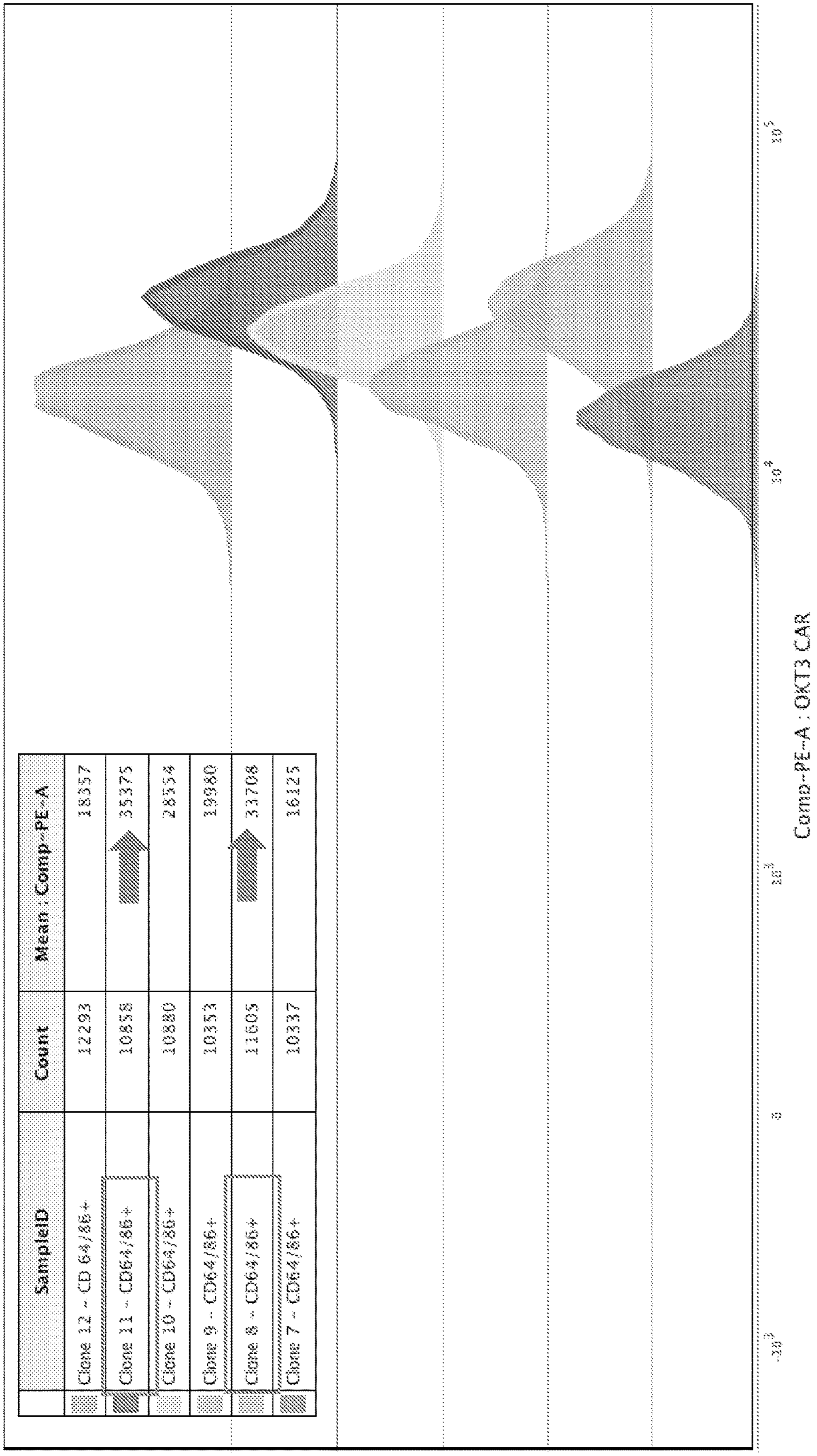
FIG. 3 illustrates the expression of the OKT3 CAR construct in various clones of the newly created K562.64.86.OKT3 cell line. Histograms indicate the level of expression of the CD3 CAR construct as assessed by flow cytometry. The legend indicates the mean fluorescence intensity (MFI) of each clone in the CD3 CAR staining channel. Boxes and arrows indicate the clones demonstrating the highest MFI (Clones 8 and 11) were selected for further development.

Various clones of the newly-created K562.OKT3 cell line were established by single-cell sorting followed by expansion in vitro. Two clones possessing the highest expression of the OKT3 CAR were then selected for further culture (FIG. 2). Likewise, two clones of the K562.64.86.OKT3 cell line were similarly selected for further expansion and use, based on level of CD3 CAR expression (FIG. 3).

Figure 4:
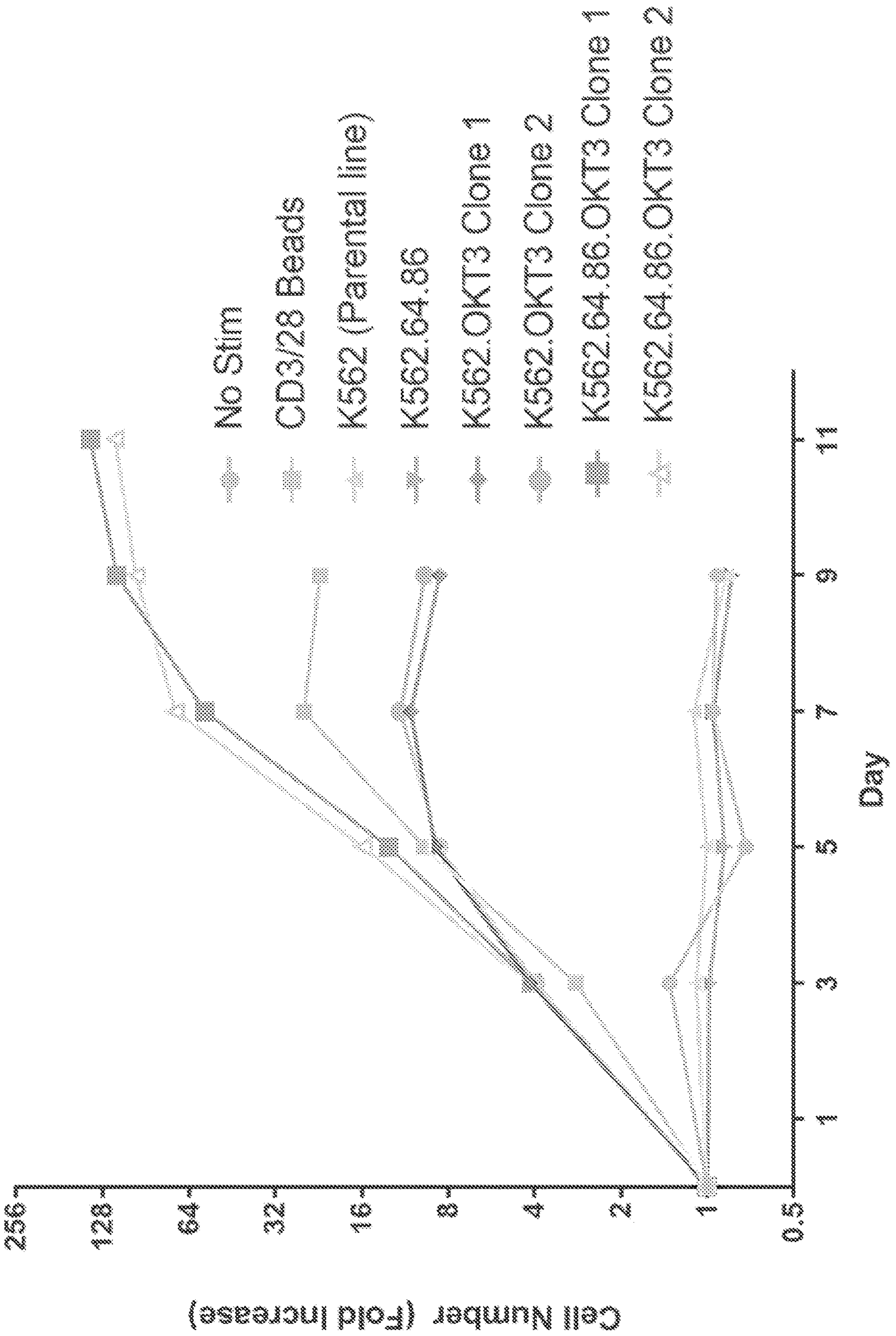
FIG. 4 illustrates the ability of the K562.OKT3 and K562.64.86.OKT3 cell lines to stimulate the expansion of human T cells. Normal donor T cells were co-incubated with various K562 cell lines for 9-12 days of culture during which the number of T cells was assessed at various time points. Data are represented as the relative fold-increase in cell number. Anti-CD3/CD28 coated beads were used as a positive control. Unstimulated T cells alone were used as a negative control.

The selected aAPC lines where then used to stimulate the expansion of human T cells in vitro. Normal donor T cells were co-incubated with various K562 cell lines for 9-12 days during which the number of T cells was assessed at various time points (FIG. 4). In these studies, anti-CD3/CD28 coated beads were used as a positive control. Unstimulated T cells alone were used as a negative control. The aAPC clones that resulted in the greatest T cell expansion were those that expressed both the OKT3 CAR and CD86, verifying the ability of these cells to provide both signal 1 and 2 to T cells, which is required for optimal activation. Stimulation with the K562-based aAPCs was more efficient than with commercially-available microbead preparations which are coated with anti-CD3 and anti-CD28 antibodies.

Figure 5:
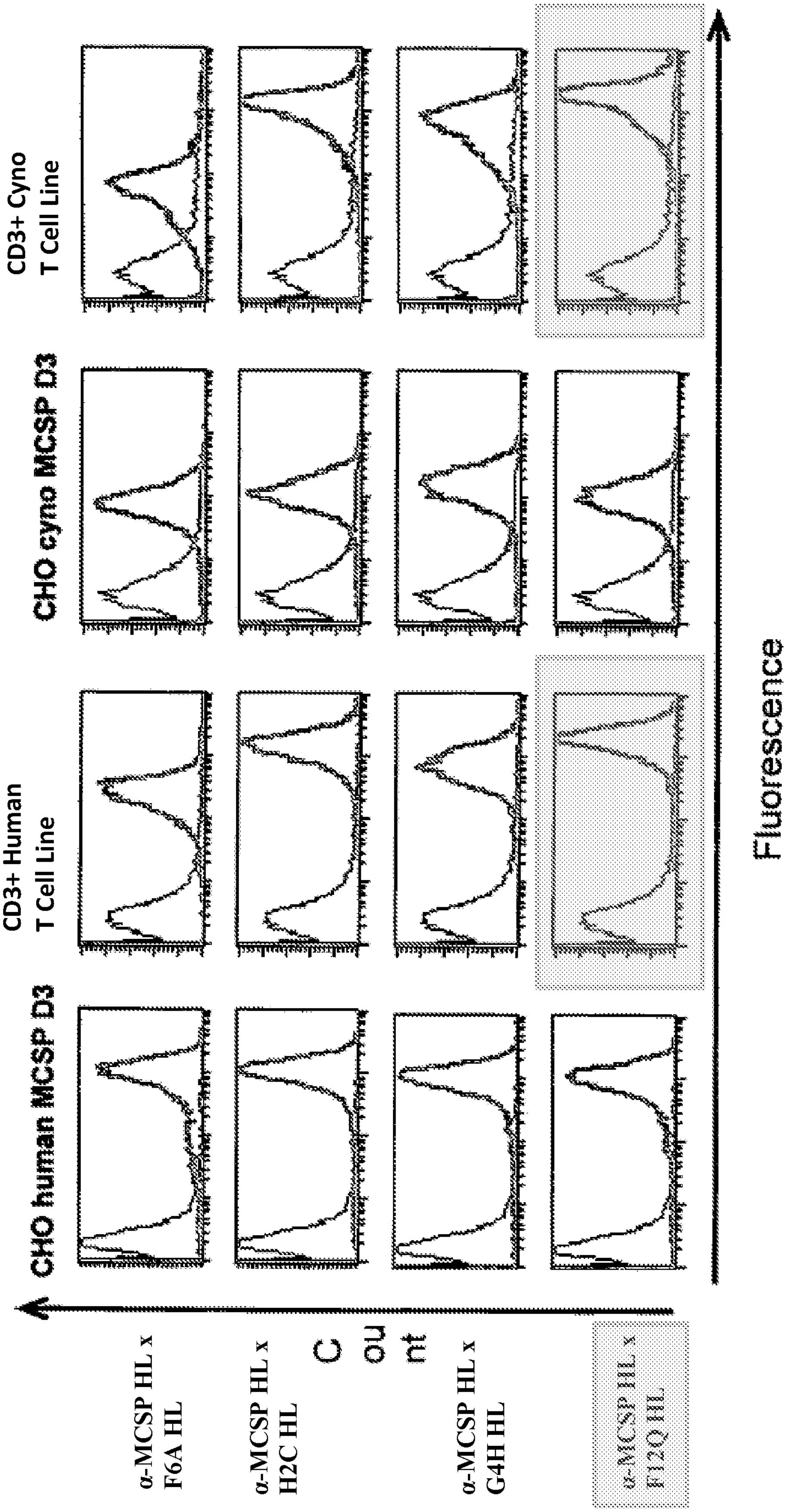
FIG. 5 illustrates, by way of background from PCT/EP2009/062795, the specificity of a Bi-specific T-cell Engager (BiTE) molecule specific for melanoma chondroitin sulphate proteoglycan (MCSP) and CD3 of both human and cynomolgus monkey origin, from which the F12Q anti-CD3 scFv was developed. Shown are flow cytometry plots illustrating the affinities of several CD3/MCSP BiTEs for MCSP-expressing CHO cells and human/monkey T cells. Shading indicates that the BiTE derived from the F12Q anti-CD3 scFv demonstrated the highest affinity for human and cynomologus CD3 and was subsequently selected for further development into an anti-CD3 scFv CAR.

Example 2: Development of an aAPC Capable of Expanding Both Human and Primate T Cells While OKT3-based aAPCs are capable of expanding human T cells, a need existed for an aAPC that was capable of expanding T cells of both human and non-human primate origins. In order to select an antibody with the highest possible affinity for both species, a number of already-constructed Bi-specific T-cell Engager (BiTE) molecules were screened (see PCT/EP2009/062795). These molecules were specific for melanoma chondroitin sulphate proteoglycan (MCSP) and CD3 of both human and cynomolgus monkey origin (FIG. 5, reproduced by way of background from PCT application PCT/EP2009/062795). The BiTE derived from the F12Q anti-CD3 scFv demonstrated the highest affinity for human and cynomologus CD3 and was subsequently selected for further development into an anti-CD3 scFv CAR.

Figure 6:
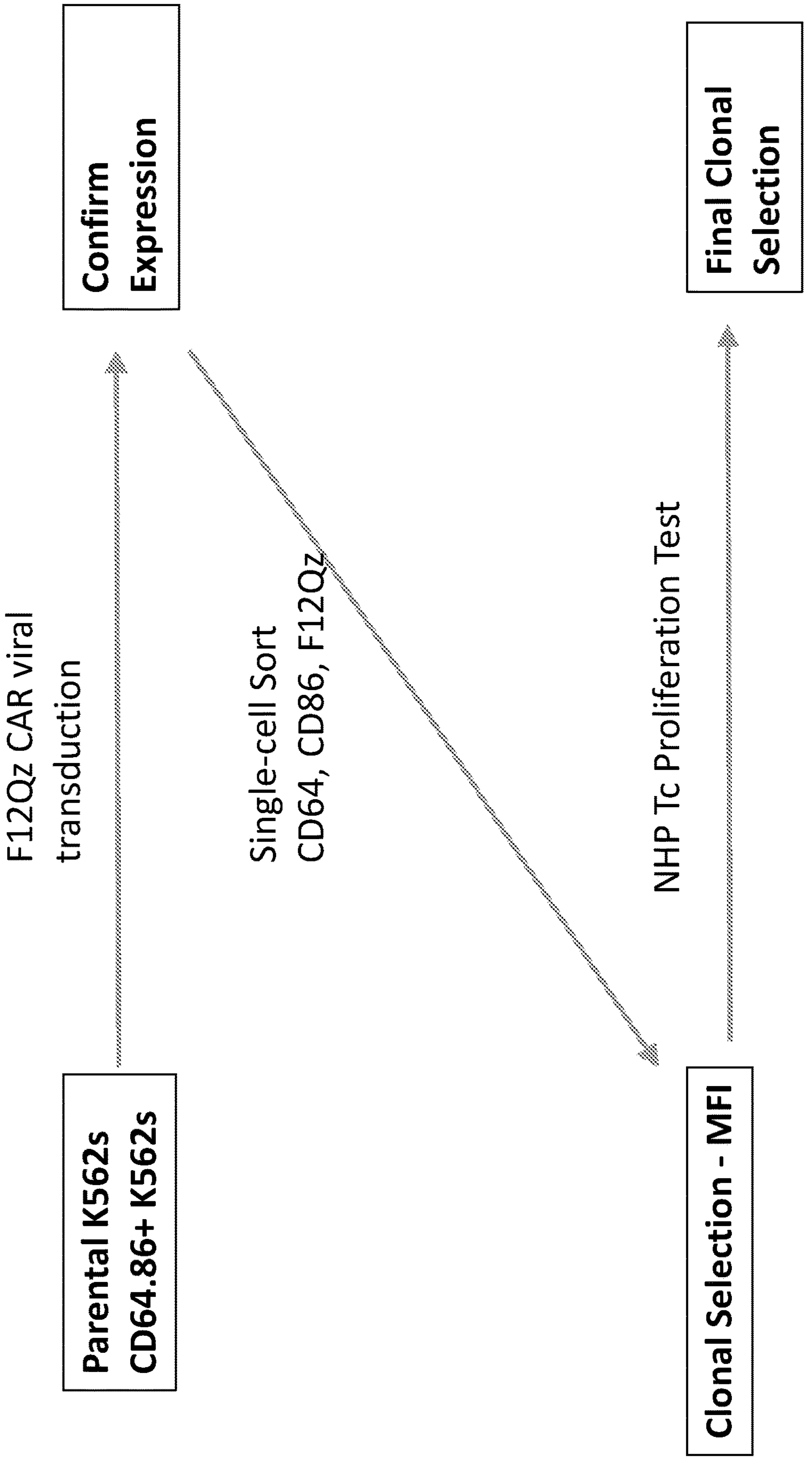
FIG. 6 illustrates the process of developing F12Qz CAR-expressing aAPCs. Parental K562 or CD64/CD86 expressing K562 cells were transduced with the F12Qz-based CAR construct, and subsequently selected for CAR expression and ability to stimulate human T cell expansion.
Figure 7:
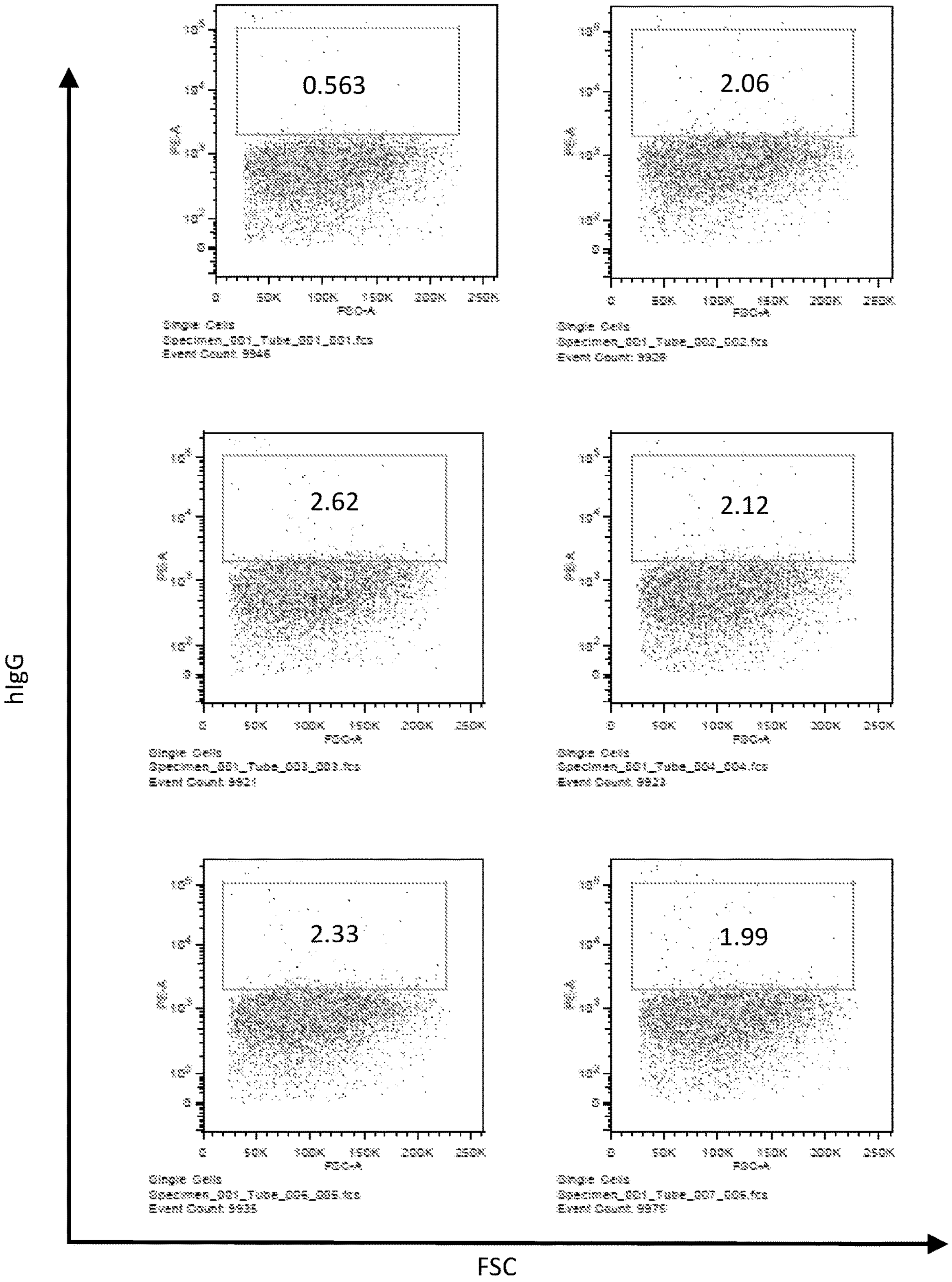
FIG. 7 illustrates that K562.64.86.F12Qz cells are undetectable using several anti-IgG antibodies of human specificity. Numbers indicate the percentage of cells staining positive.

The F12Q-based CAR was then transduced into K562 parental cells and K562 cells expressing CD86 and CD64, followed by clonal selection for those cells possessing the highest CD3 CAR expression and the greatest ability to expand human and primate T cells. A flowchart of these studies is illustrated in FIG. 6. In order to detect the expression of the F12Q scFv on the surface of the cells for, a number of anti-IgG antibodies were screened for binding (FIG. 7). As none of the tested antibodies demonstrated any detectable binding, subsequent studies used biotinylated CD3 protein as a primary stain followed by counterstaining with PE-conjugated streptavidin.

Figure 8:
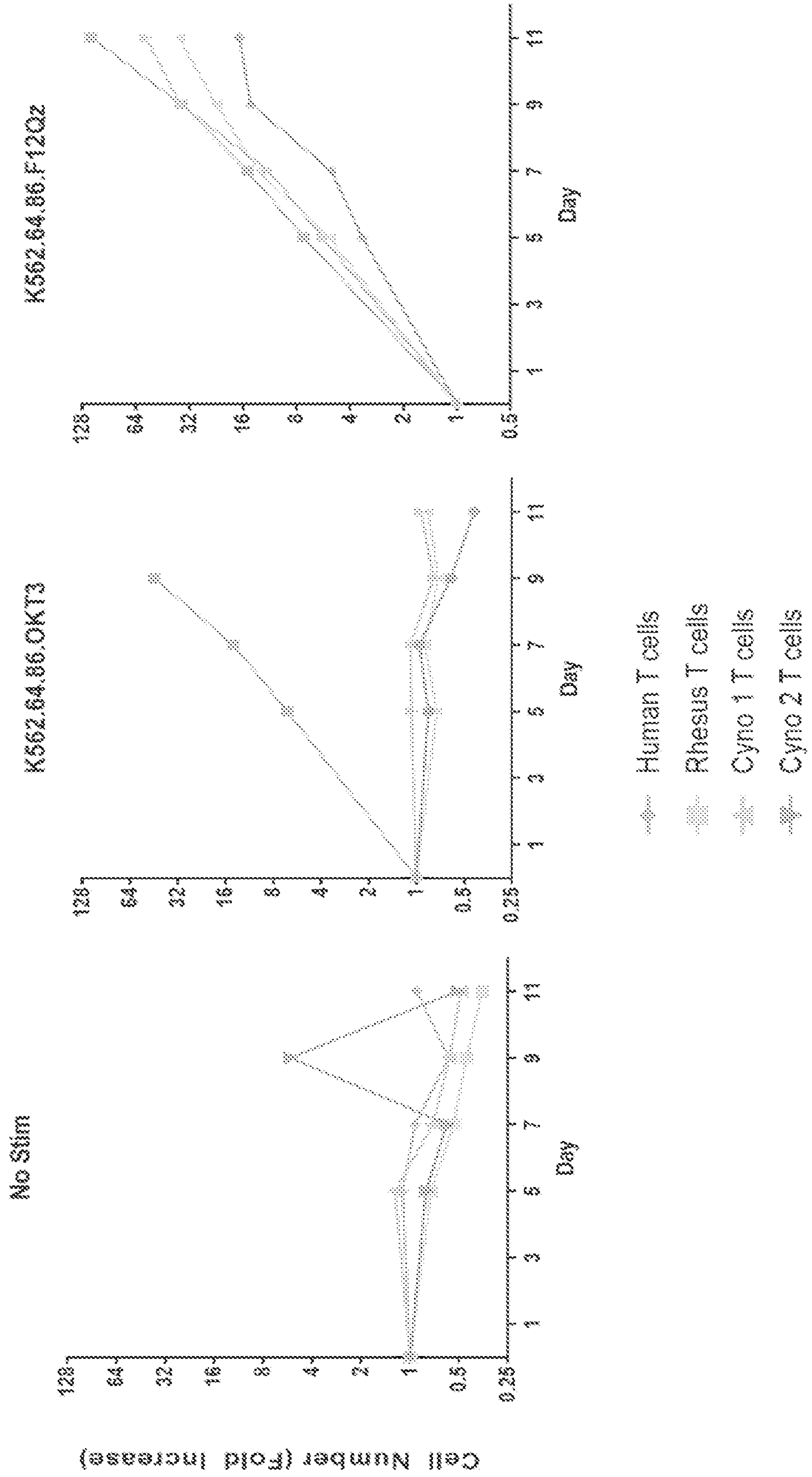
FIG. 8 illustrates the ability of F12Qz CAR-expressing K562.64.86 cells to induce the proliferation of both human and non-human primate T cells. K562.64.86 cells expressing either the OKT3-CAR (middle) or F12Qz-CAR (right) were co-incubated with human T cells or T cells from rhesus monkeys or cynomolgus monkeys. T cell expansion was assessed at various time points over 12 days, and data is represented as the fold increase in T cell number. As a negative control, T cells were left unstimulated (left panel).
Figure 9:
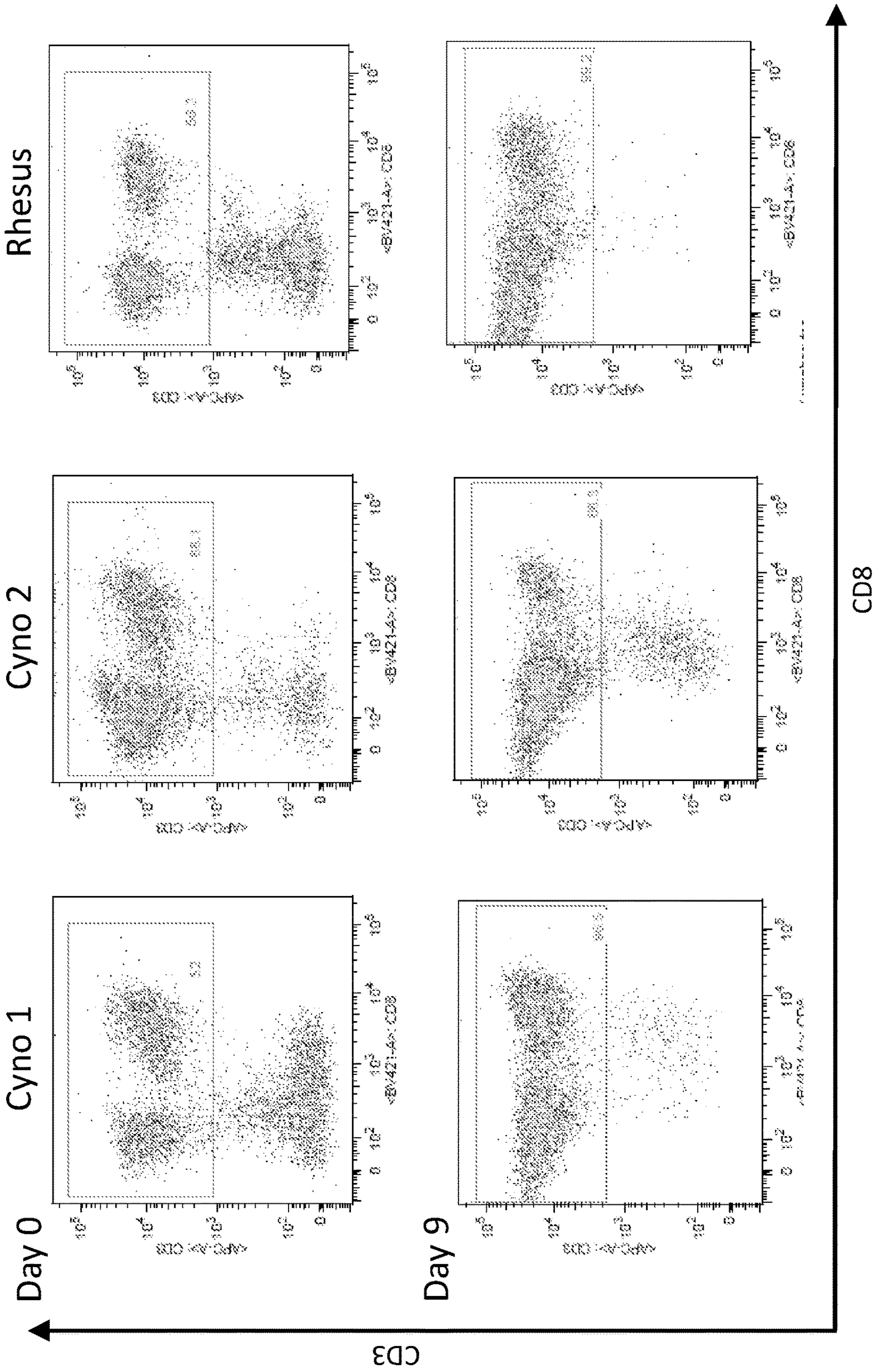
FIG. 9 illustrates that K562.64.86.F12Qz aAPCs selectively stimulate and expand non-human primate (NHP) T cells. T cell populations from two cynomolgus monkey donors or a rhesus monkey donor were stimulated with K562.64.86.F12Qz cells for 9 days followed by staining for CD3 and CD8 expression and read-out by flow cytometry. Donor cells stained prior to expansion are shown on the top row. The corresponding groups of cells stained after 9 days expansion are shown on the bottom row.

F12Q CAR-expressing K562.64.86 cells were used to expand T cells from a human donor and two non-human primates: rhesus and cynomolgus monkeys. As a control, OKT3-CAR based a APCs were used for comparison. Consistent with the cross-species specificity of the F12Q antibody, F12Q-CAR based aAPCs efficiently promoted the expansion of T cells from all three species (FIG. 8). Similarly, only human T cells expanded after stimulation with OKT3-CAR expressing aAPCs. In both studies, expansion was determined by assessing the fold increase in the number of cells. Staining for CD3 and CD8 after nine days of culture further demonstrated the loss of CD3-negative T cells, and thus the preferential expansion and survival of CD3+ T cells (FIG. 9).

Figure 10:
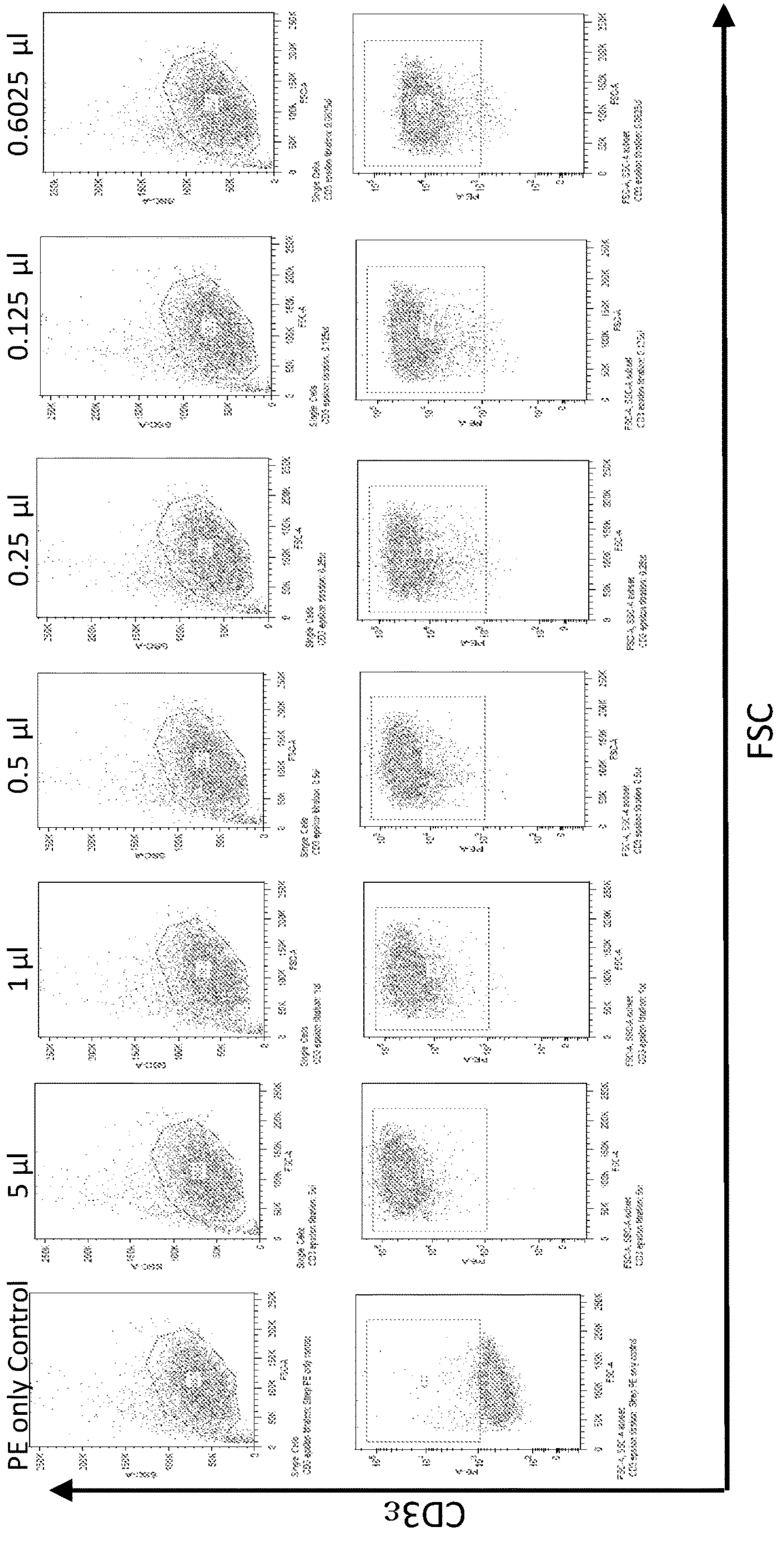
FIG. 10 illustrates the development of a soluble CD3c protein used to stain K562.64.86.F12Qz cells. Cells were stained with indicated amounts of soluble, biotinylated CD3ε protein followed by counterstaining with PE-conjugated streptavidin as a secondary stain. Stained cells were then analyzed using flow cytometry. The top row shows the forward/side scatter profile of each group, as well as the gating used for further assessment of PE (CD3c) staining (bottom row).
Figure 11:
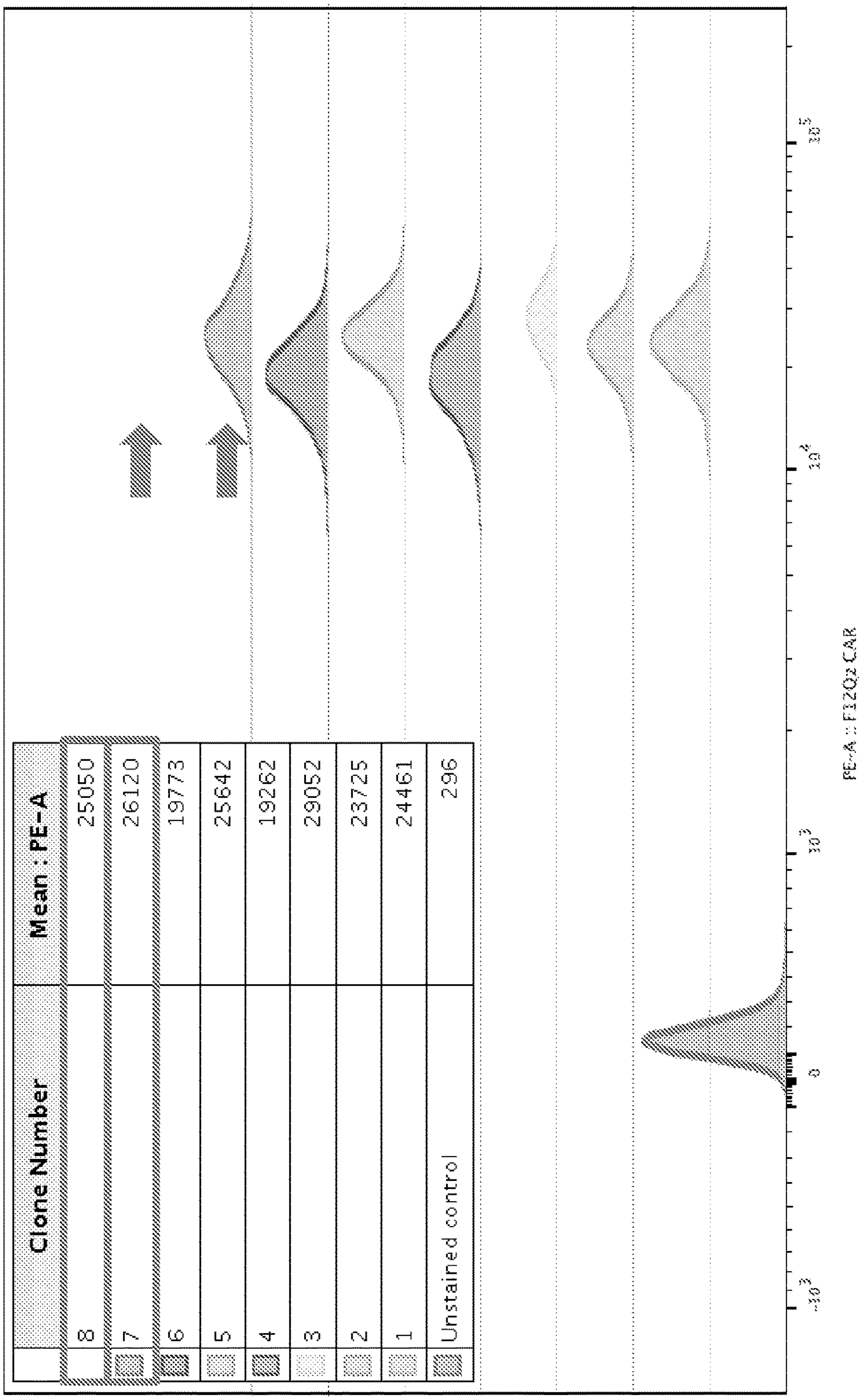
FIG. 11 illustrates the expression of F12Qz CAR constructs in various clones derived from the newly generated K562.64.86.F12Qz cell line. Histograms represent the level of construct expression, as assessed by staining with soluble, biotinylated CD3c protein followed by streptavidin-PE. The legend indicates the mean fluorescence intensity of staining for each clone. Boxes and arrows indicate that the clones demonstrating the highest MFI (clones 7 and 8) were selected for further development.

In order to allow for the specific staining of anti-CD3 CAR expressing aAPCs for identification using flow cytometry, a soluble CD3-epsilon protein and PE-conjugated streptavidin counterstain was utilized. Titration studies using various concentrations of the CD3E protein ranging from 0.6025 μg/ml to 5 μg/ml demonstrated clear staining with minimal background (FIG. 10). This CD3 CAR staining strategy was used to select two F12Q-CAR expressing aAPC clones demonstrating the highest level of expression for further use (FIG. 11).

Example 3: Enhancing aAPCs to Deliver Optimal T Cell Stimulation

The development of CD3-CAR expressing aAPC cells represents a substantial improvement over previous iterations of K562-based aAPCs in that the endogenously-expressed, membrane-bound anti-CD3 scFv constructs obviate in vitro loading of anti-CD3 antibody onto Fc receptors prior to co-culture with T cells, a step which previous generations of aAPC required. In addition to saving time and labor in a process which has become increasingly important as CAR-based immunotherapies develop into more common clinical treatments, anti-CD3 CARs also eliminate the constant expense of sourcing and testing anti-CD3 antibodies.

The use of exogenous cytokines such as IL-7 and IL-15 in T cell cultures promotes optimal expansion and maintenance of effector functions, even after multiple rounds of in vitro stimulation. Similar to the use of anti-CD3 CARs, the modification of aAPC to secrete IL-7 and IL-15 provides the benefits of these factors without the need to supplement cultures with purified preparations. K562 OKT3-CAR expressing aAPCs were transduced to secrete IL-7 with a construct that also expresses the red fluorescent protein (RFP) mCherry as a trackable marker. Cells were then further engineered to secrete a heterocomplex of IL-15 linked to the IL-15R alpha chain (sushi domain) via a linker. This modified version of IL-15 has been shown to be a higher affinity IL-15 agonist than the recombinant cytokine alone. The progression of K562-based aAPC development is illustrated in FIG. 12. Each "version" incorporates additional features to improve the efficiency of handling and T cell stimulation.

Figure 20:
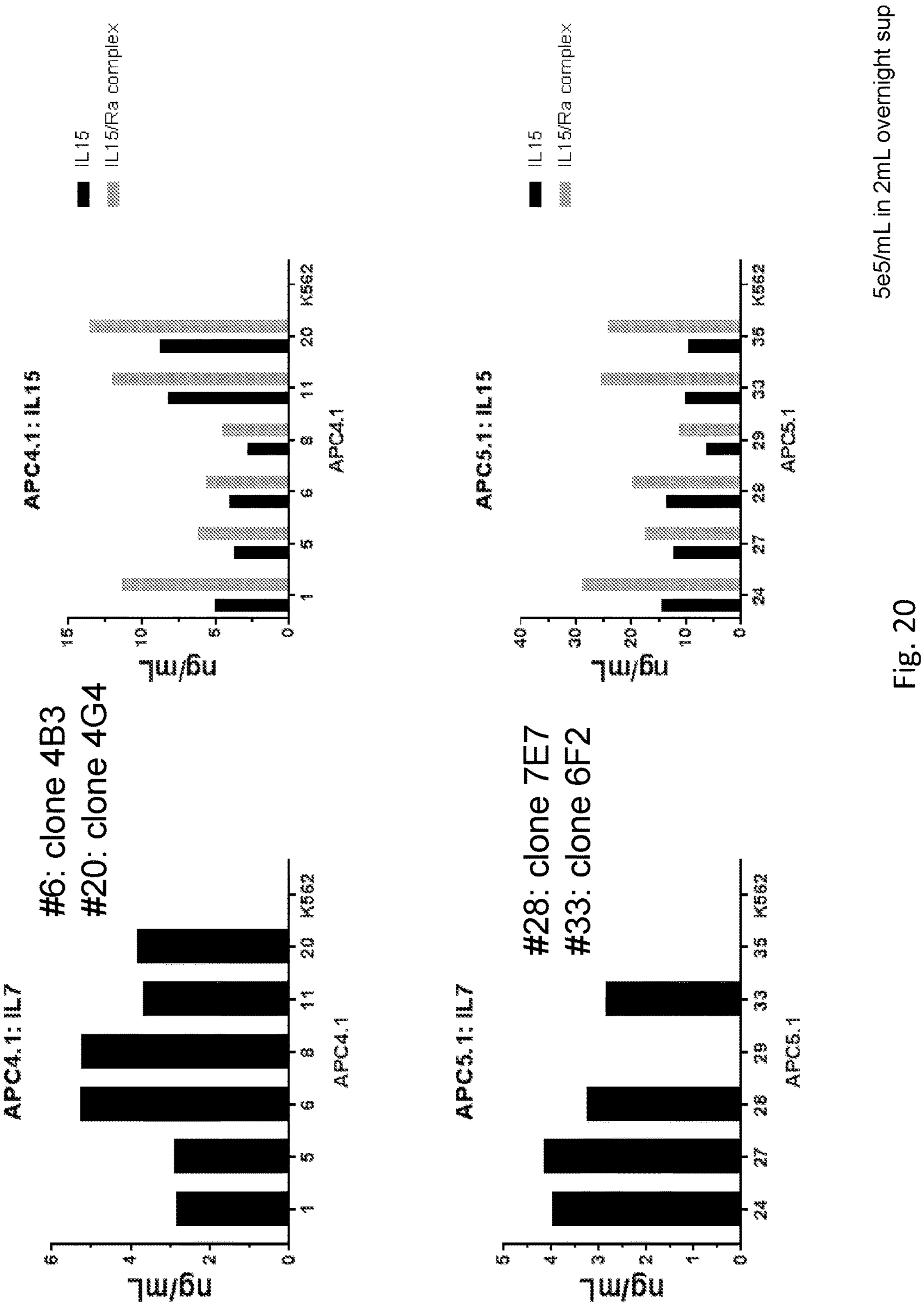
FIG. 20 illustrates the expression levels of transduced cytokine in six APC4.1 (top row) and six APC5.1 (bottom row) clones. 5e5 cells/mL were cultured in 2 mL total volume overnight followed by harvest of the conditioned media for cytokine measurement of IL-7 (left) and IL-15 (right) concentration by ELISA.

Ten clones were established from transduced "APC4.1" cells (CD64+4-1BBL+OKT3-CAR+IL-7+IL-15+CD86neg) and expression of transduced molecules was assessed by flow cytometry (FIG. 14A-14B). Similar staining of transduced "APC5.1" cells (CD64+4-1BBL+OKT3-CAR+IL-7+IL-15+CD86+) also identified a number of clones possessing high expression of transduced proteins (FIG. 15A-15B). Seven "APC4.1" and six "APC5.1" clones were then selected for further screening of their ability to expand human T cells (FIG. 16). Results demonstrated the ability of both "APC4.1" and "APC5.1" type aAPCs to expand human T cells, however the "APC5.1" aAPCs resulted in a greater degree of expansion. Two clones of each "version" were selected for further development based on transgene expression and ability to stimulate T cell expansion. In order to assess stability of transgene expression, these clones were then cultured for up to nine passages and stained for CD64, 4-1BBL, CD86, IL-15R, and OKT3-CAR expression (IL-7 expression was determined by mCherry expression). Both "APC4.1" (FIG. 17) and "APC5.1" (FIG. 19) maintained high levels of protein expression, as compared to low-passage cells (FIG. 18, showing "APC4.1" clones). Cytokine secretion by the various clones was also assessed by ELISA (FIG. 20). Those clones which had been previously identified based on their stimulation efficacy and transgene expression by flow cytometry staining also demonstrated the ability to produce significant amounts of cytokine as measured by ELISA.

Figure 21A:
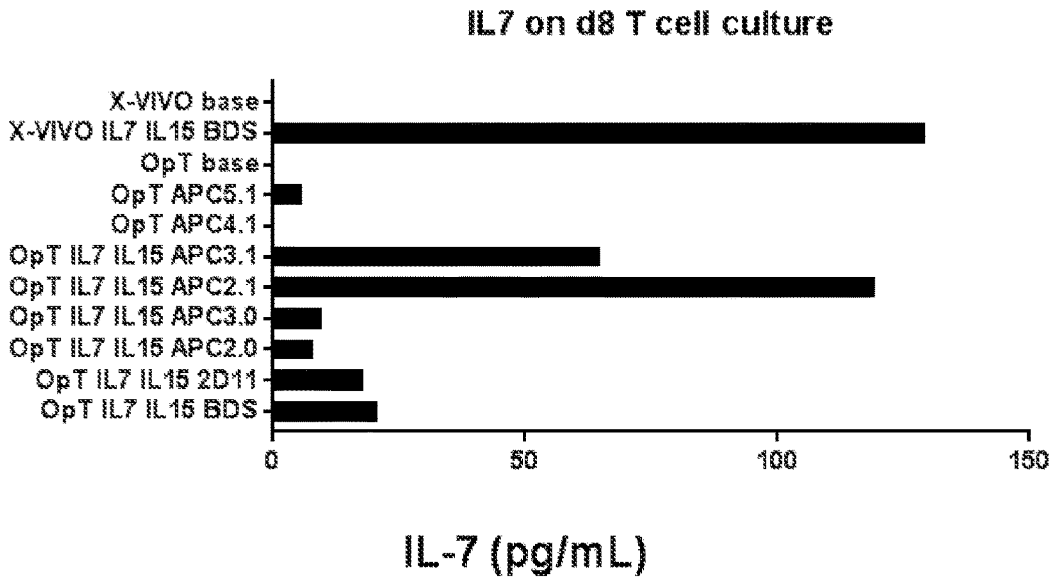
FIGS. 21A-21C illustrate the persistence of cytokine presence in T cell cultures after 8 days stimulation with various artificial APCs or beads in X-VIVO or OpTmizer serum-free media. T cells were stimulated by co-culture with the indicated APCs (APC2.0, 3.0, 2.1, 3.1, 4.1, or 5.1), anti-CD3 antibody loaded APCs (2D11), or anti-CD3/CD28 beads (BDS) for eight days. Exogenous IL-7 and IL-15 was added to cultures with APCs that did not produce them endogenously (beads, 2D11, and APC3.1/2.1/3.0/2.0). Unstimulated T cells cultured in X-VIVO and OpTmizer media alone was used as a negative control (base). Culture media was then assessed for the concentration of IL-7 (FIG. 21A), IL-15 (FIG. 21B), and IL-15/15R (FIG. 21C) by ELISA.
Figure 21B:
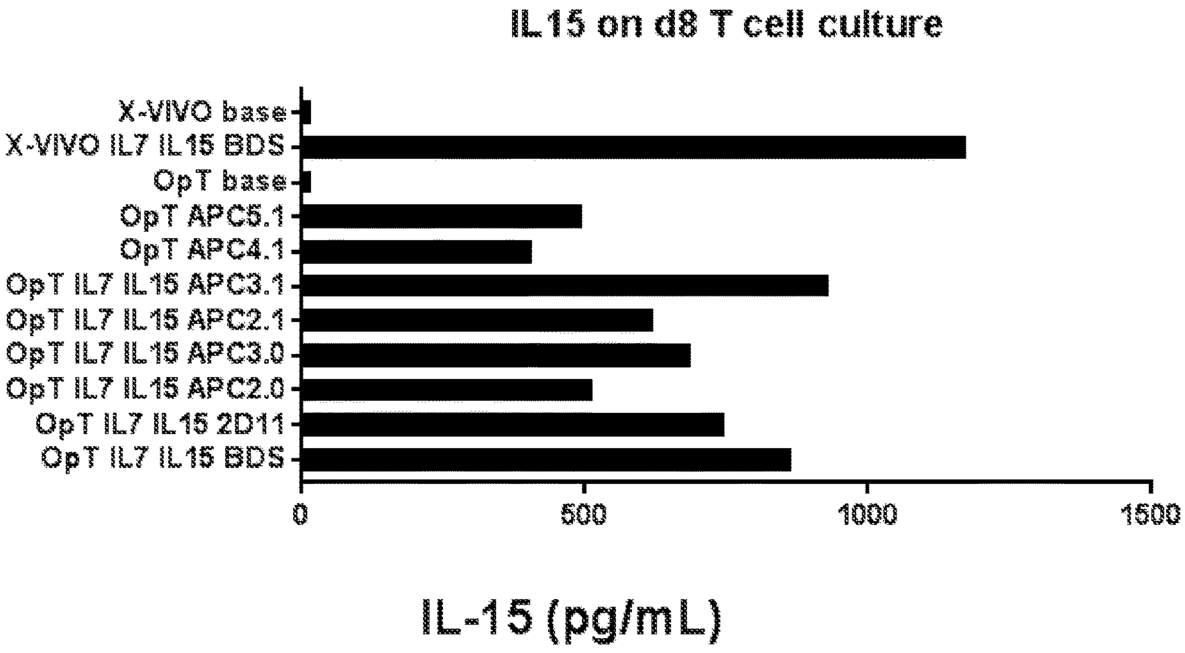
Figure 21C:
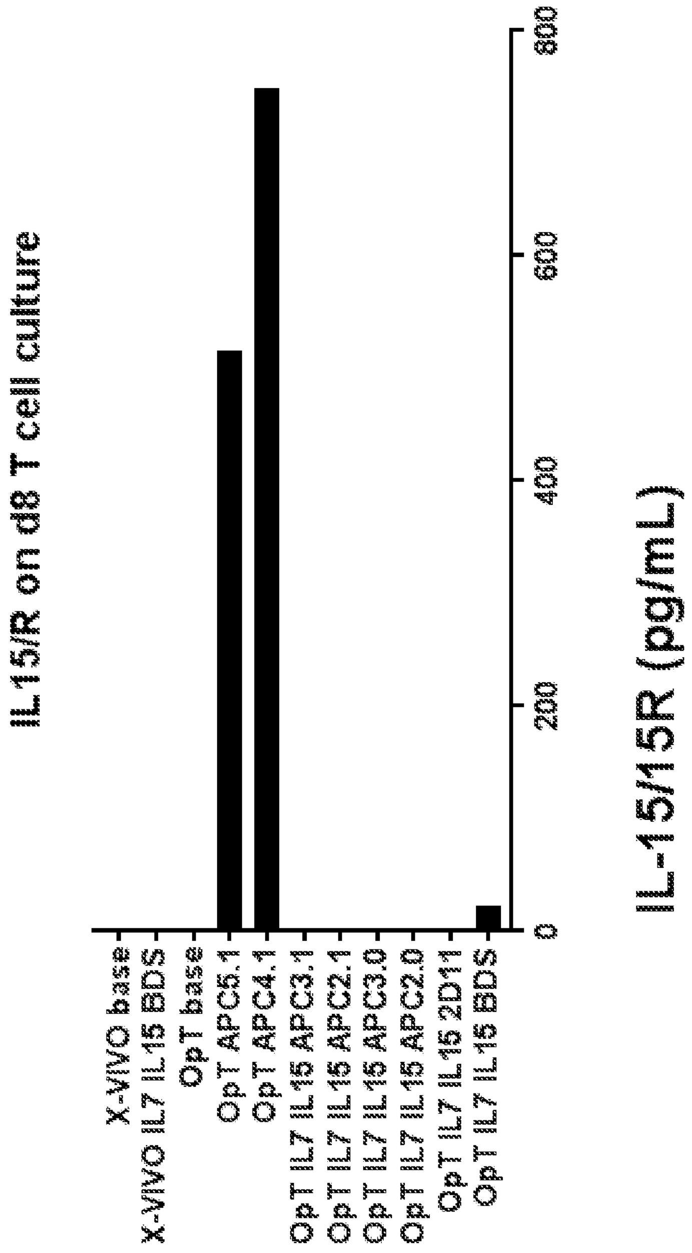

The presence of cytokines in culture media after 8 days of T cell expansion was then determined. In these studies, the ability of APC5.1 and APC4.1 cells to continuously produce IL-7 and IL-15 was assessed in comparison to various culture conditions with exogenous IL7 and IL-15 added, including APC2.0, 3.0, 2.1, and 3.1 aAPC cells, anti-CD3 antibody (2D11), as well as commercially available anti-CD3/anti-CD28 coated beads. Additionally, two kinds of serum-free culture media were evaluated: X-VIVO and OpTmizer. Measurement of IL-7 (FIG. 21A), IL-15 (FIG. 21B), and IL-15/15R (FIG. 21C) by ELISA revealed equivalent production of IL-15 by APC4.1 and APC5.1 cells. Likewise, these cells were the only ones producing IL-15R, as expected. However, IL-7 production was lower in these cells than in groups receiving exogenous IL-7.

Figure 22:
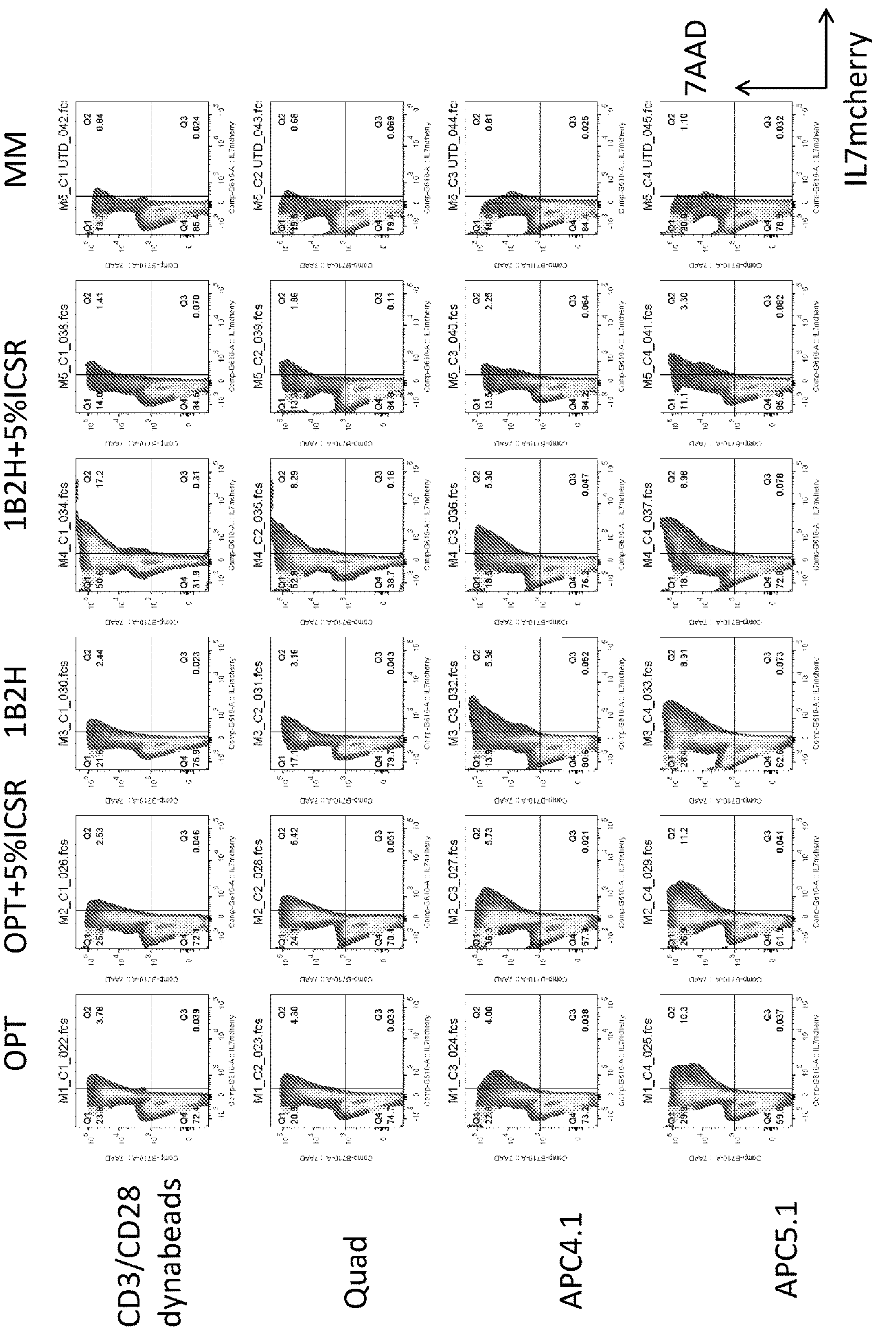
FIG. 22 illustrates the lack of persistence of artificial APCs in T cell co-cultures after 7 days. IL-7-mCherry expressing APCs were co-cultured with donor T cells from patient #3-07409_104 for 7 days under various culture conditions. Cultures were then stained with the viability dye 7-AAD and assessed for mCherry expression via flow cytometry. Control cultures were stimulated with anti-CD3/CD28 dynabeads and dynabeads plus cytokines (quad).
Figure 23:
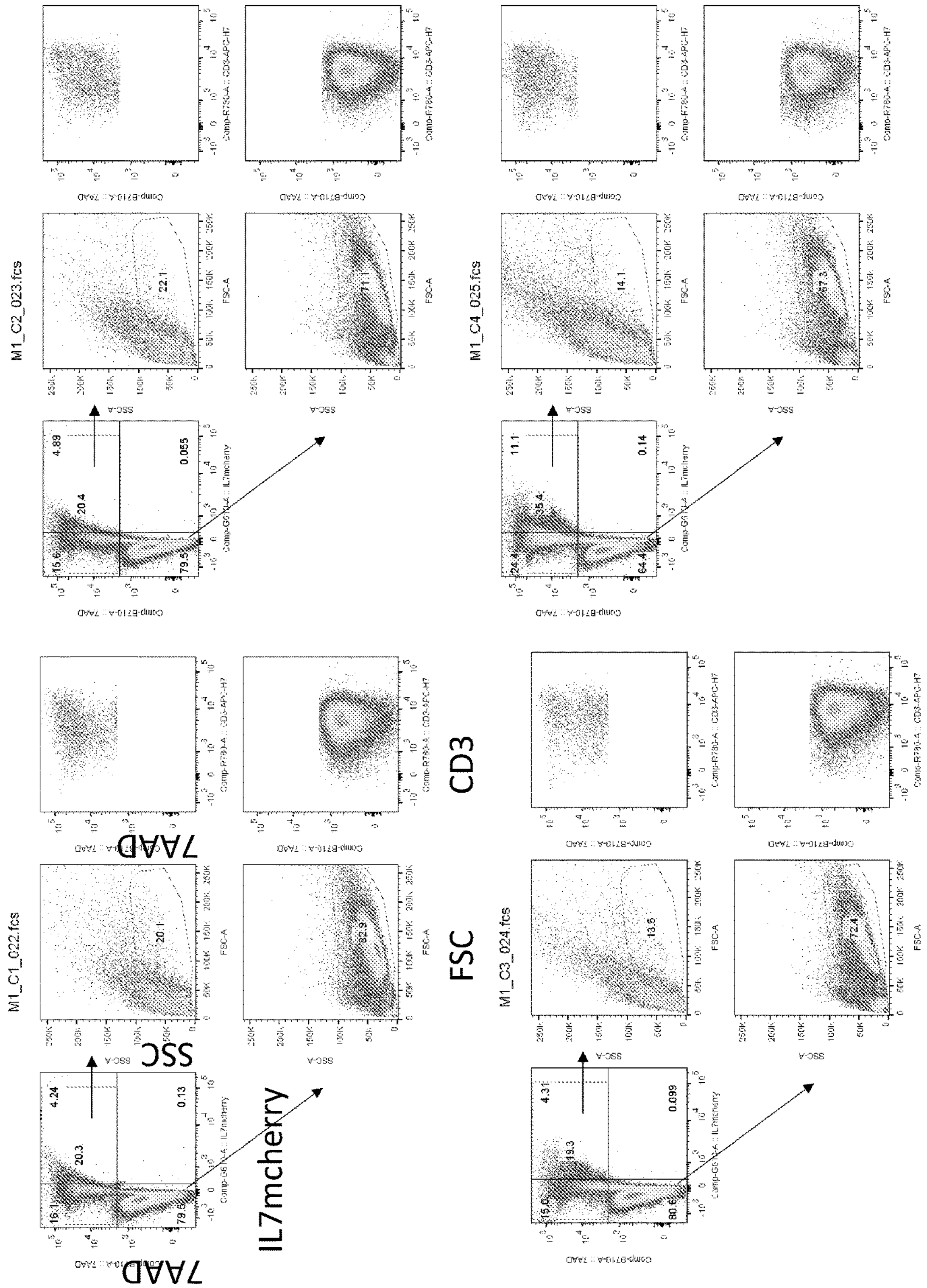
FIG. 23 illustrates the lack of persistence of artificial APCs in a T cell co-culture using cells from another human patient (#3-13406_03). After seven days of culture, cells were stained with the viability dye 7-AAD and mCherry expression was assessed by flow cytometry. Double positive and double-negative populations were separated by quadrant gating, and each population was assessed for forward/side scatter and CD3 expression to demonstrate that the remaining live cells were T cells.
Figure 24:
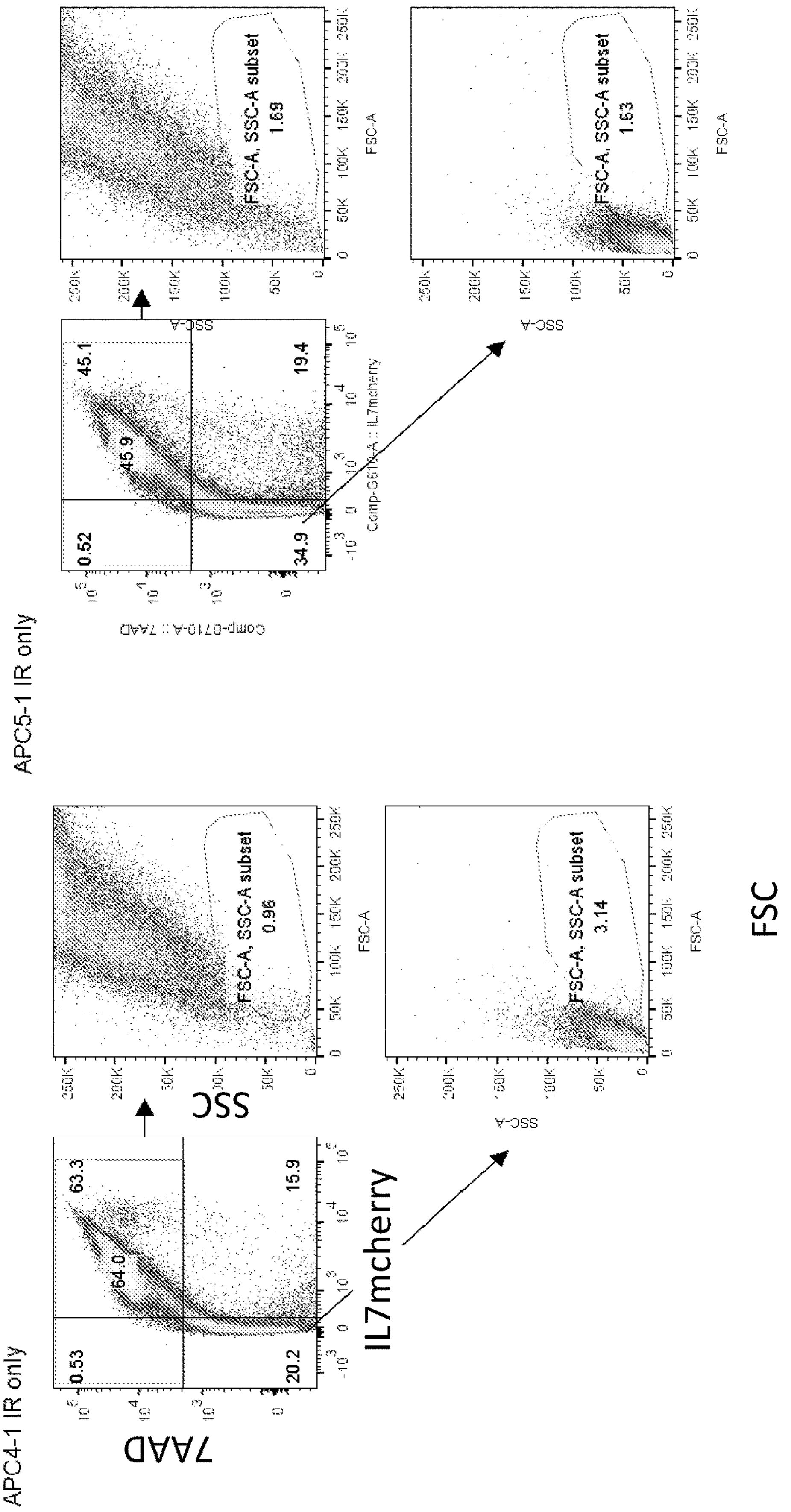
FIG. 24 illustrates that irradiated artificial APCs do not persist after a 7 day culture. APC4.1 (left) and APC5.1 (right) cells were irradiated and cultured for 7 days in vitro. Cells were then stained with 7-AAD and read-out by flow cytometry comparing viability dye staining and mCherry expression.

The continued presence of aAPCs in culture after stimulating the expansion of T cells can be detrimental to the health of the resulting T cells, in that the non-T cells contribute to overcrowding and consume nutrients otherwise necessary to support the T cells. As such, traditional T cell culture protocols often include treatments of stimulator cells that arrest their growth, including irradiation or treatment with mitomycin C. This step is also key in the production of T cells for immunotherapy, as it minimizes the amount of purification would need to be done to the culture to remove non-T cells prior to infusion into patients. APC4.1 and APC5.1 aAPCs were irradiated prior to use in T cell expansion co-cultures. After 7 days, the cultures were assessed for remaining aAPC cells by staining cells with the viability dye 7-AAD and assessing for mCherry expression (FIG. 22). Results showed virtually no persisting aAPCs (FIG. 23). Those cells that were positive for mCherry were uniformly non-viable, as indicated by 7-AAD positivity (FIG. 24).

Example 4: High Efficiency Expansion of T Cells for Therapeutic Use

Figure 13:
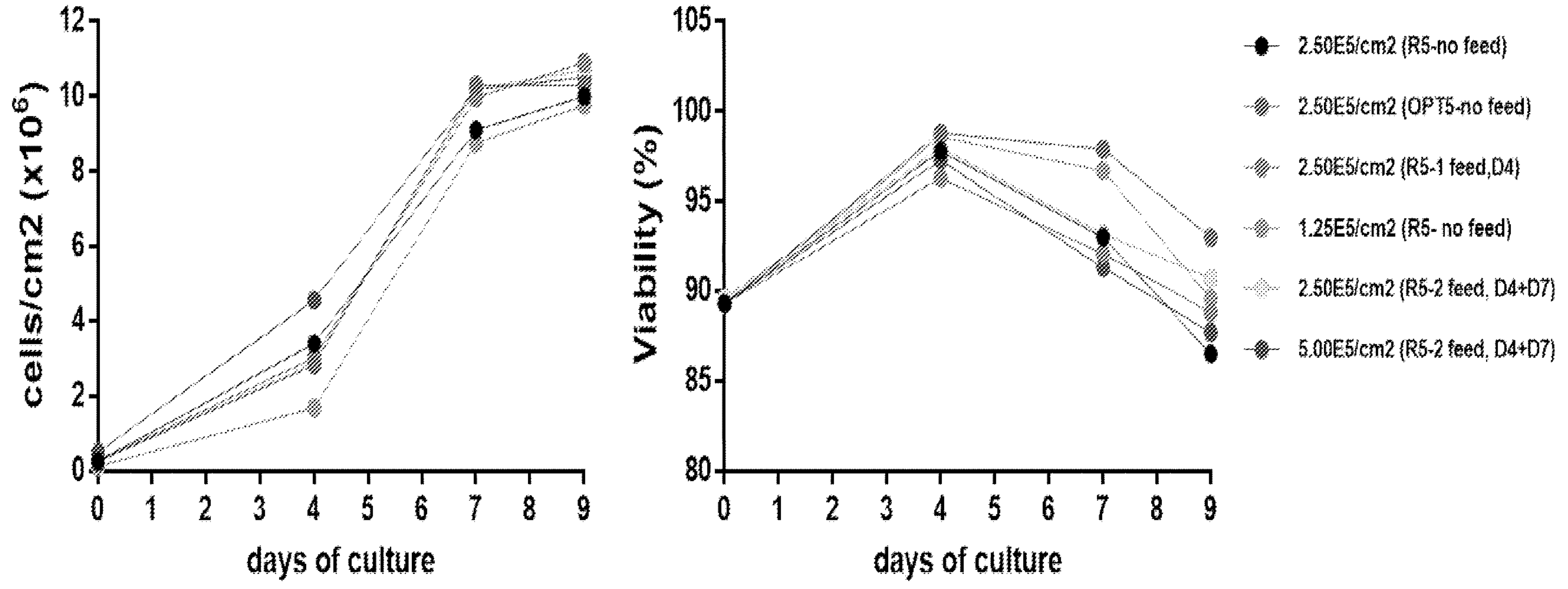
FIG. 13 illustrates a comparison of T cell expansion systems. Capabilities and costs of the existing (WAVE) process is compared to the newly developed (GREX) process.
Figure 25:
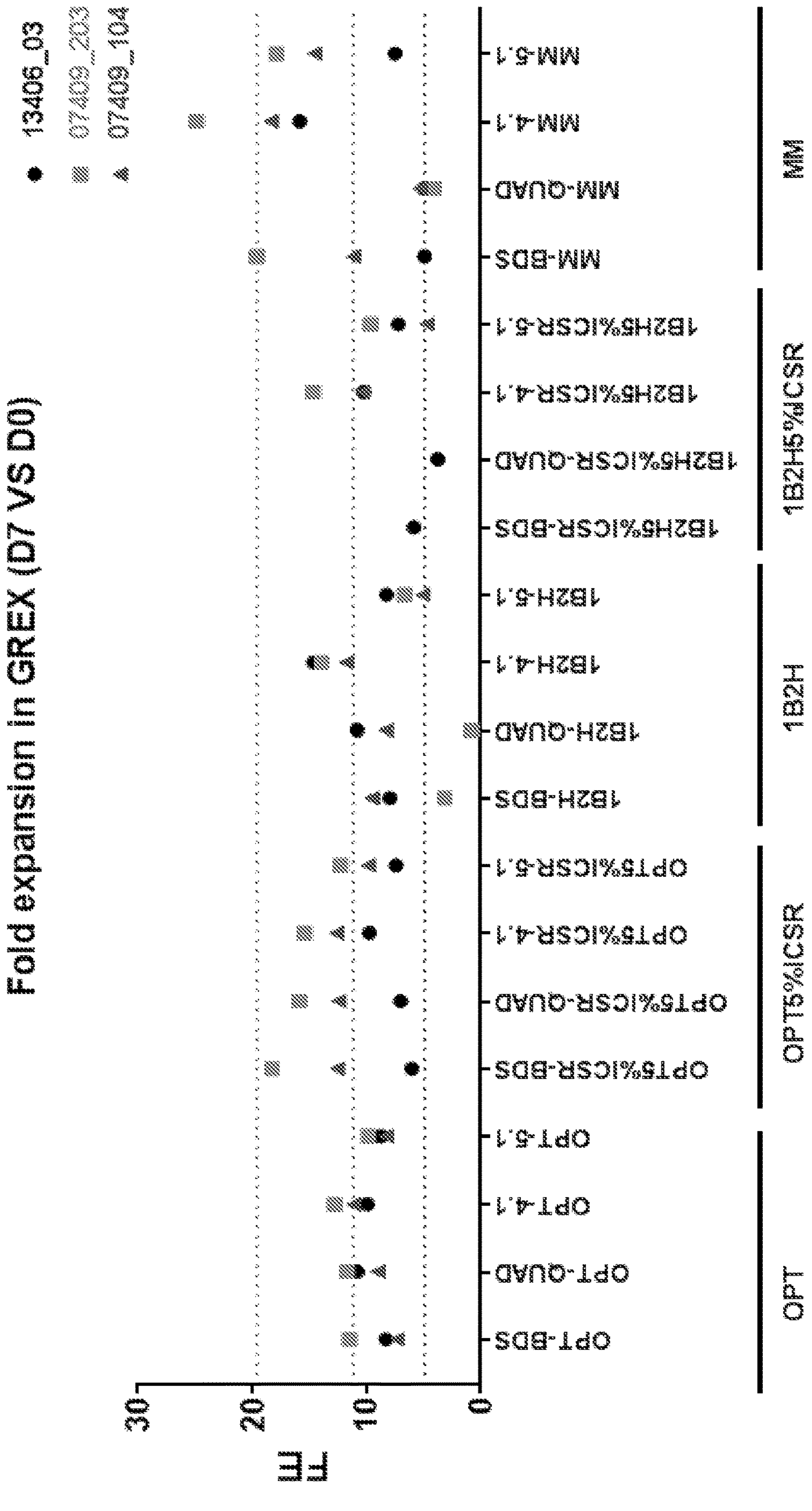
FIG. 25 illustrates the expansion of T cells from three human patients using various serum-free mediums in the GREX culture device. The degree of expansion for each culture condition/patient cell group was determined by comparing the number of cells at the beginning of the culture (day 0) to the end (day 7) and determining the fold expansion (FE).
Figure 26:
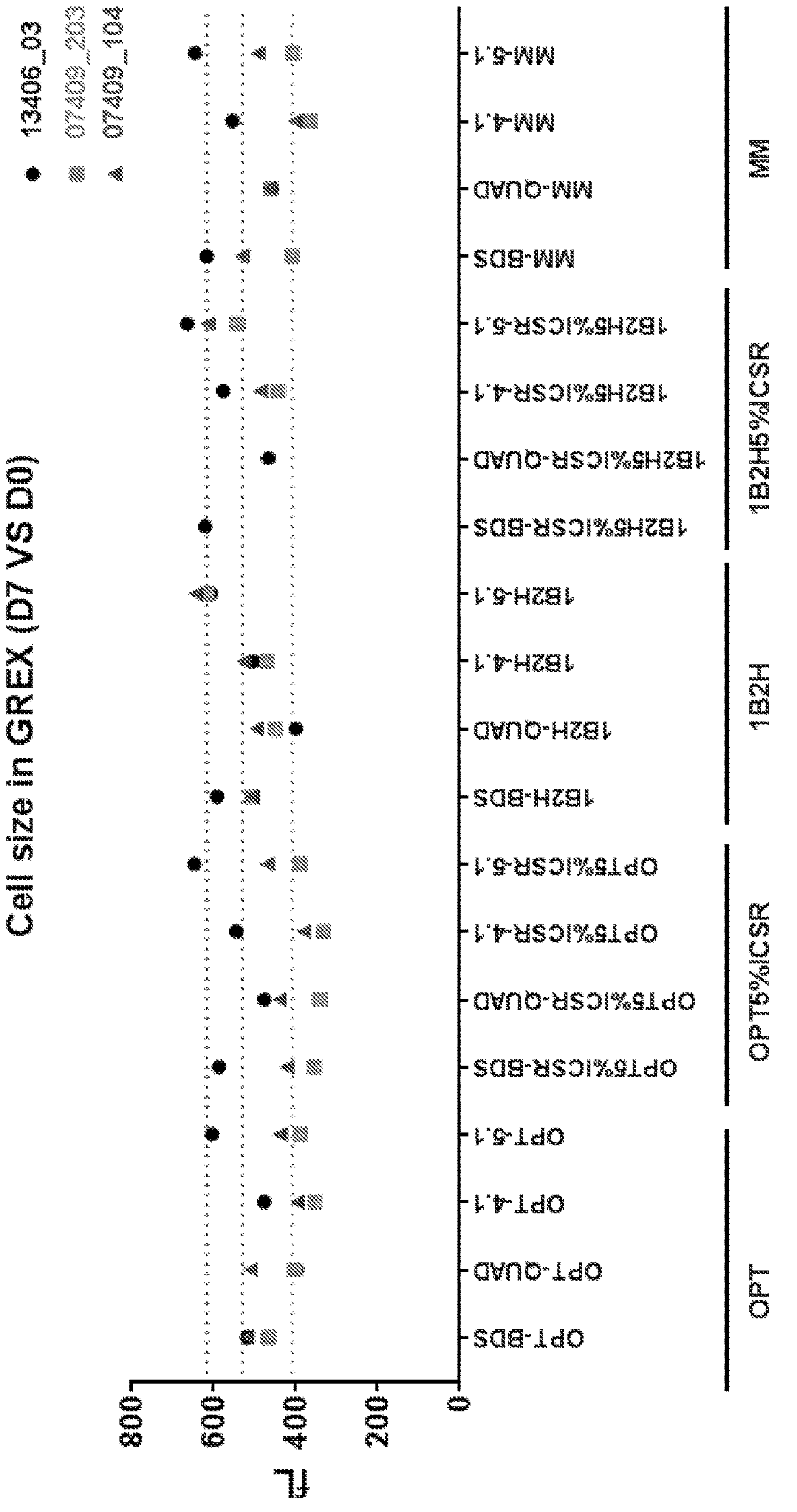
FIG. 26 illustrates the change in T cell size of human patient T cells under various culture conditions in the GREX culture device. T cells from three different patients were subjected to similar indicated culture conditions using various serum-free mediums and aAPCs.
Figure 29:
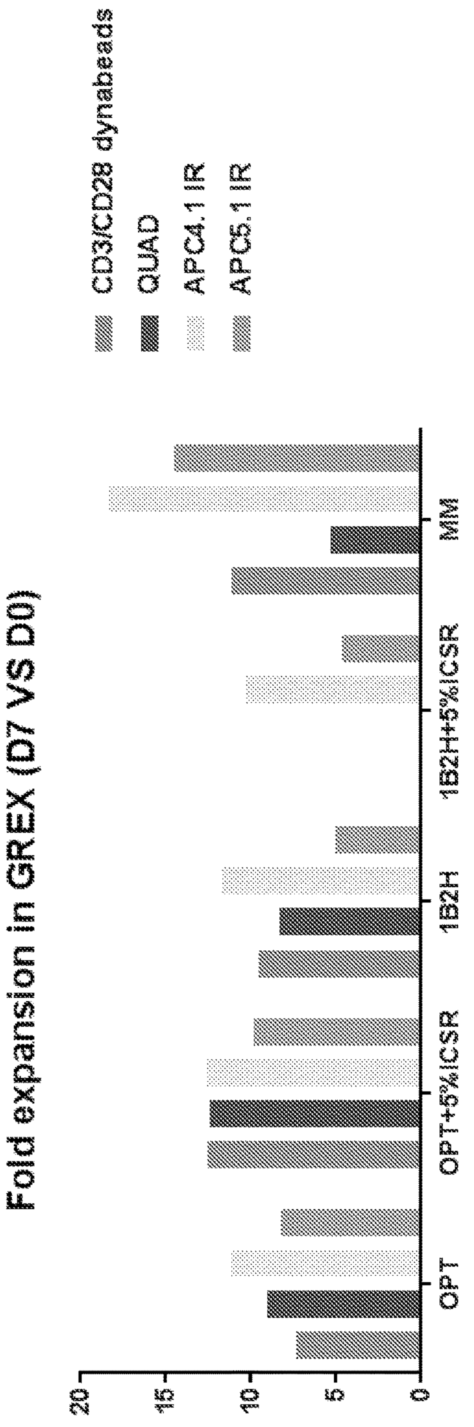
FIG. 29 illustrates the fold expansion of T cells using various stimulation methods and serum-free media formulations using the GREX culture device.
Figure 30:
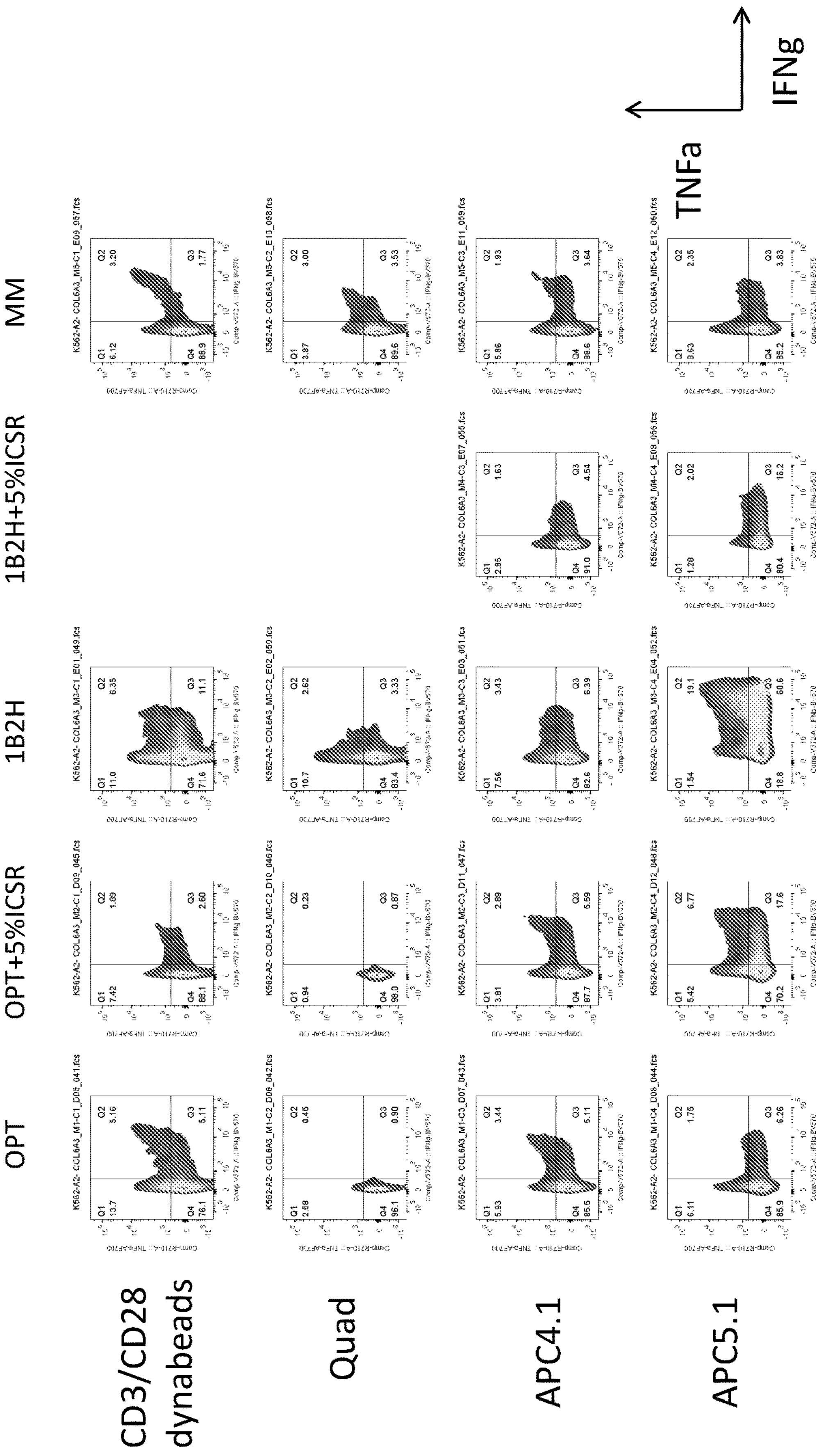
FIG. 30 illustrates cytokine production by restimulated T cells following expansion using various aAPC and stimulation methods and cultured in various serum-free media conditions as used in FIGS. 25, 26, and 29.

Cell-based immunotherapies such as chimeric antigen receptor (CAR) expressing T cells require the production of large numbers of T cells from individual patients using GMP-compatible methods. While current methods often make use of WAVE bioreactor technology, GREX bioreactors offer the possibility of expanding equivalent numbers of cells in shorter amounts of time with lower costs (FIG. 13). In order to assess the feasibility of combining APC4.1 and APC5.1 aAPCs with the GREX bioreactor, a series of studies were conducted which compared these aAPCs with conventional anti-CD3/CD28 microbeads (BDS) and soluble anti-CD3/CD28 stimulator Cloudz (QUAD) in several types of media preparations (FIG. 25). The fold expansion of T cells from three human patients was assessed over the course of seven days. Depending on the conditions, APC4.1 and APC5.1 cells induced expansion similar or better than microbeads. Likewise, cell size comparisons between day 0 and day 7 for each patient under each stimulation condition found consistent results (FIG. 26 and FIG. 29). T cells expanded using these methods were then restimulated, and the production of TNFα and IFNγ was then assessed (FIG. 30). Expansion with APC4.1 and APC5.1 cells resulted in similar or better levels of cytokine production as anti-CD3/anti-CD28 dynabeads with APC5.1 inducing the greatest cytokine production. These results demonstrated that APC4.1 and APC5.1 aAPC cells could be successfully used with efficient bioreactors to create large numbers of T cells sufficient for further use in applications such as immunotherapy.

Figure 27A:
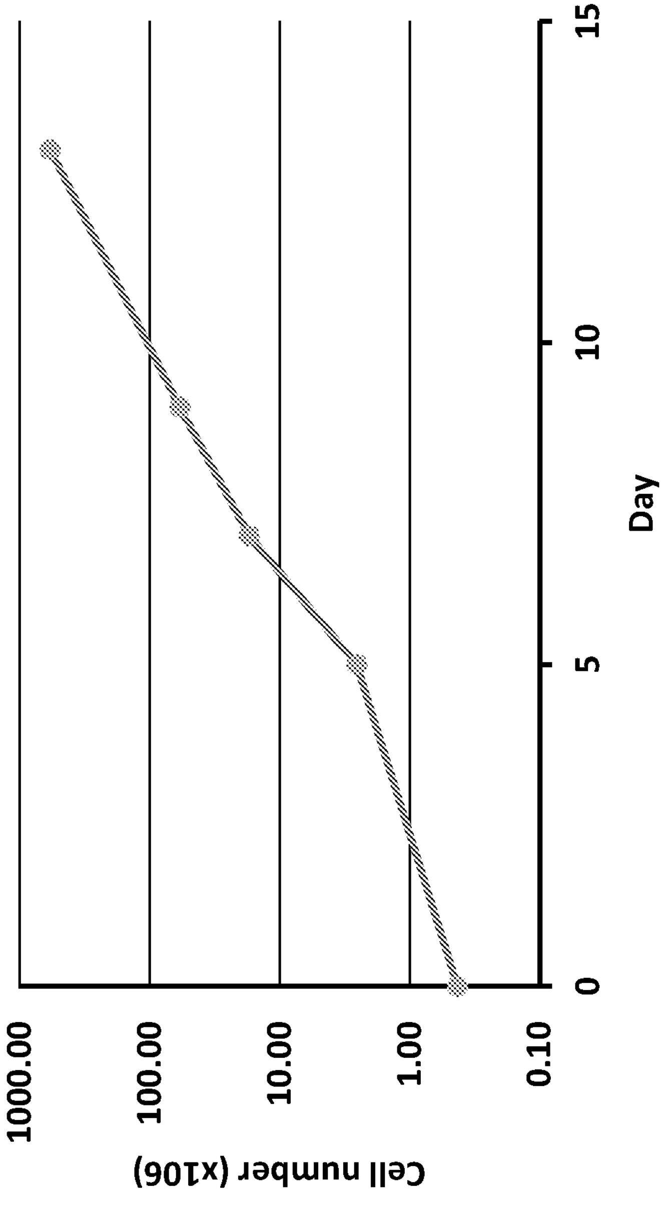
FIGS. 27A-27B illustrate the expansion of CD4+ CD25+ CD127low/− CD45RA+ regulatory T cells (Treg) from human donor peripheral blood by co-culture with APC3.1. Cells were cultured in XVIVO medium with 5% human AB serum, 1× glutamax, 1× pen/strep and 200 IU/mL IL-2 for 14 days. Cells were restimulated with APC3.1 on day 9. On day 14, cells were stained with CD4-BV421 (OKT4), CD8-BV510 (RPA-T8), CD25-APC (BC96), and FoxP3-PE-Dazzle594 (206D).
Figure 27B:
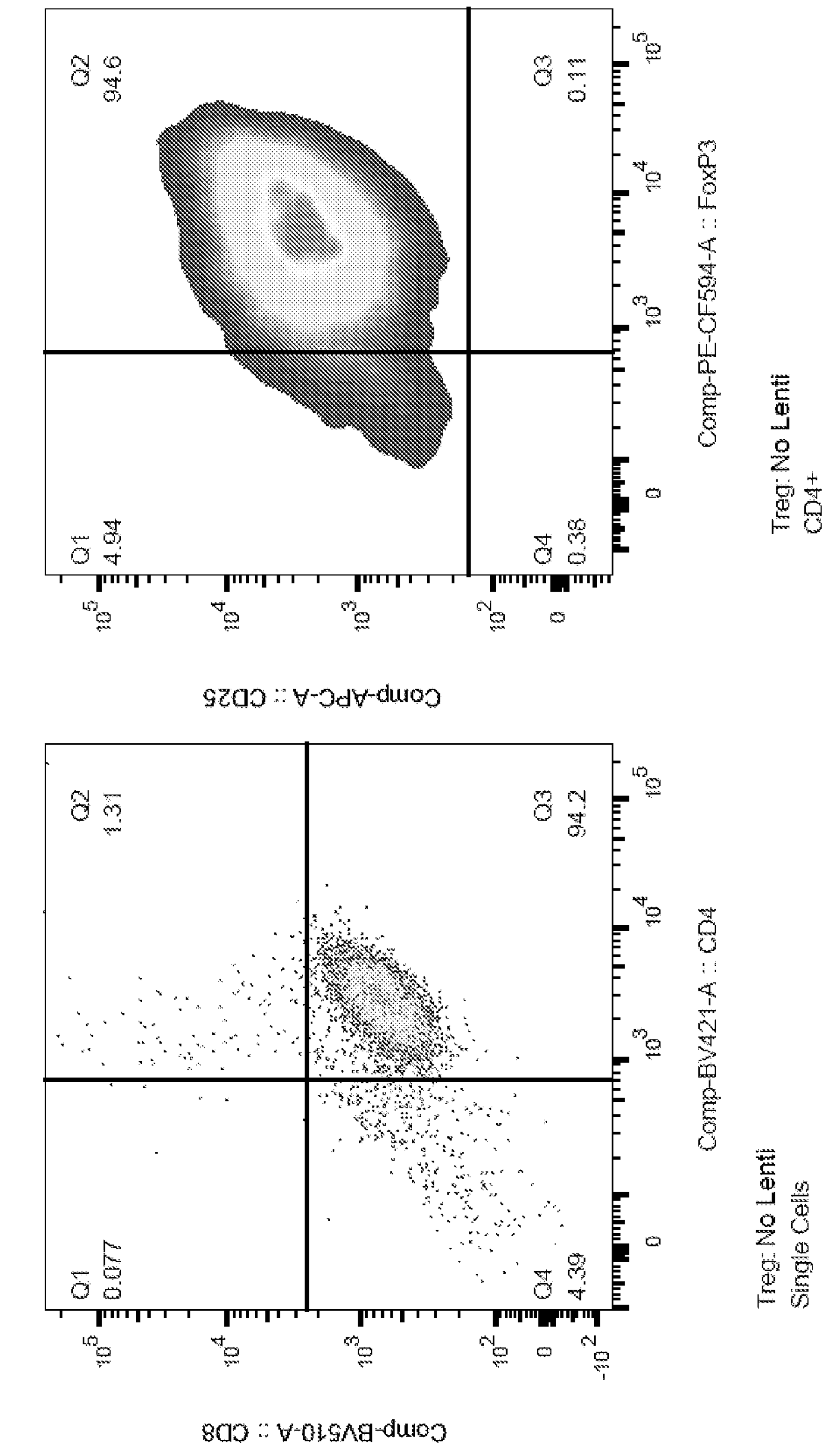
Figure 28:
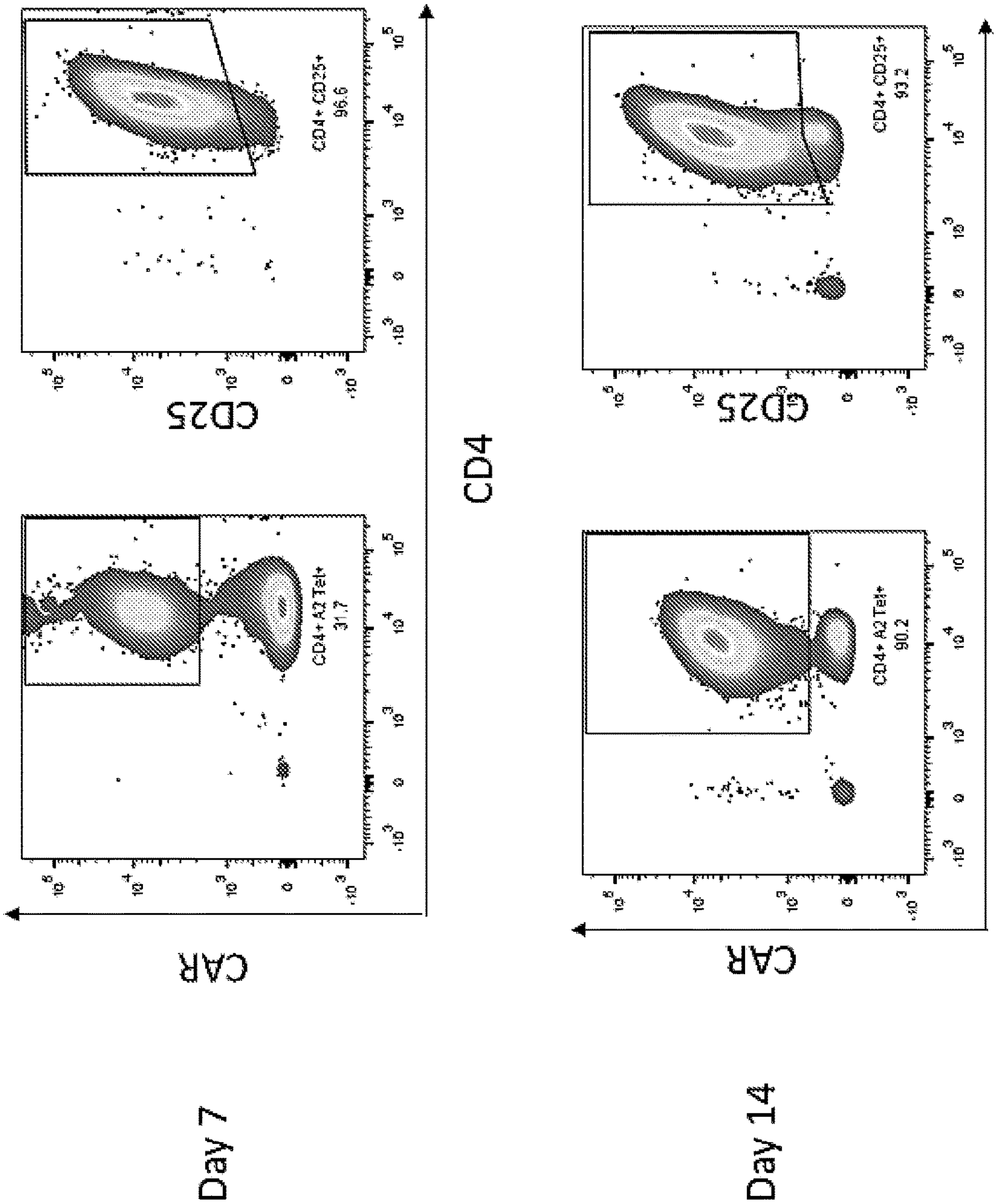
FIG. 28 illustrates the expansion and transduction of non-human primate regulatory T cells (Treg). Cynomolgus macaque regulatory T cells were stimulated on day 0 with irr. K562.F12Q.64.86 in RPMI+10% FBS+10 mM HEPES+1× Glutamax+1× pen/strep+IL-2. On day 2, virus encoding for human HLA-A2 specific CAR was added to the cell culture. On day 7, cells were restimulated with irradiated K562.A2.86 cells to restimulate cells such that only the CAR+ cells would expand, increasing the percentage of CAR+ cells.

The high-volume expansion of CD4+ regulatory T cells (Tregs) offers the ability to use adoptive T cell therapy to reduce or ameliorate immune disorders arising from inappropriate or excessive immune activation. To determine whether the aAPCs and culture methods of the current disclosure could efficiently expand regulatory T cells, CD4+ Treg were sorted from donor peripheral blood and expanded by co-culture with APC3.1 in XVIVO medium with 5% human AB serum, 1× glutamax, 1× pen/strep and 200 IU/mL IL-2 for 13 days. Cells were then restimulated with APC3.1 on day 9. FIG. 27A is a growth curve illustrating the efficient expansion of CD4+ Treg over the course of the study. On day 14, cells were stained for expression of CD4, CD8, CD25, and Foxp3 (FIG. 27B) which demonstrated that expanded cells retained an expression phenotype consistent with CD4+ regulatory T cells. The clinical utility of expanded Tregs would be increased if the cells could also be engineered to express chimeric antigen receptors. In this way, expanded Treg could be directed to specific antigenic targets. To assess whether CD4+ Treg expanded using the aAPC of the current invention, Treg sorted from non-human primate (cynomolgus macaques) peripheral blood were stimulated on with irradiated K562.F12Q.64.86 cells with IL-2. On day 2, virus encoding for human HLA-A2 specific CAR was added to the cell culture. On day 7, cells were restimulated with irradiated K562.A2.86 cells such that only the CAR+ cells would expand, increasing the percentage of CAR+ cells. On days 7 and 14, expression of the CAR and CD25 expression as assessed on the expanding Treg (FIG. 28). These stains demonstrated that Treg were efficiently transduced and retained CD25 expression. Overall, and without wishing to be bound by theory, these results demonstrated the utility of the aAPCs of the current invention for the in vitro expansion of CD4+ regulatory T cells from both human and non-human primate donors such that the expanded cells retained the ability to be efficiently transduced to express chimeric antigen receptor constructs, which increase their clinical utility.

Example 5: Expansion of T Cells Using aAPC-Derived Membrane Vesicles

Figure 31A:
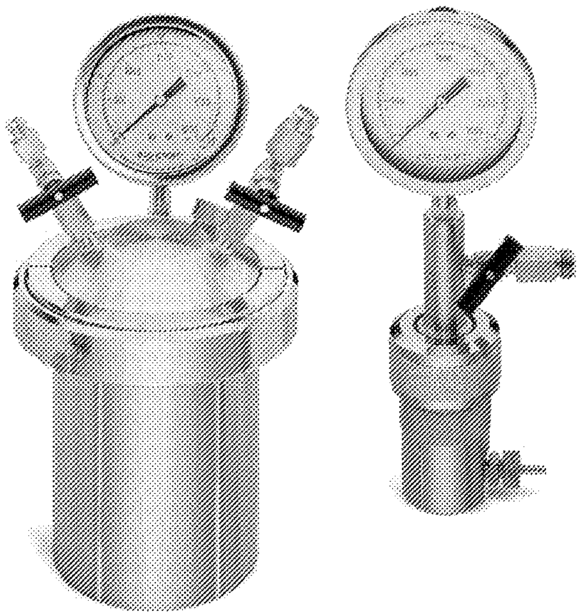
FIGS. 31A-31B depict the use of nitrogen cavitation to disrupt aAPCs in order to generate APC-like membrane vesicles.
Figure 31B:
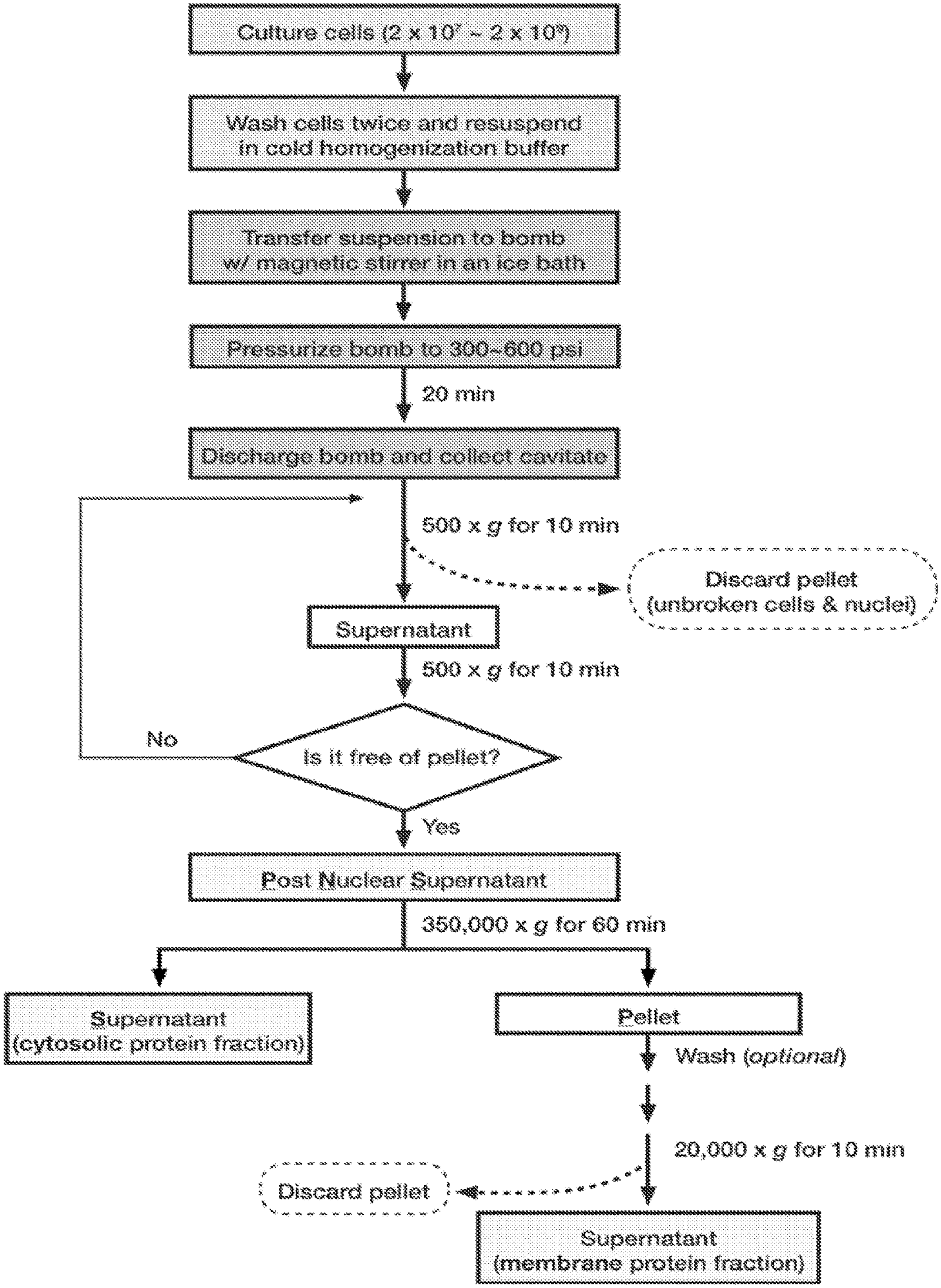
Figure 32:
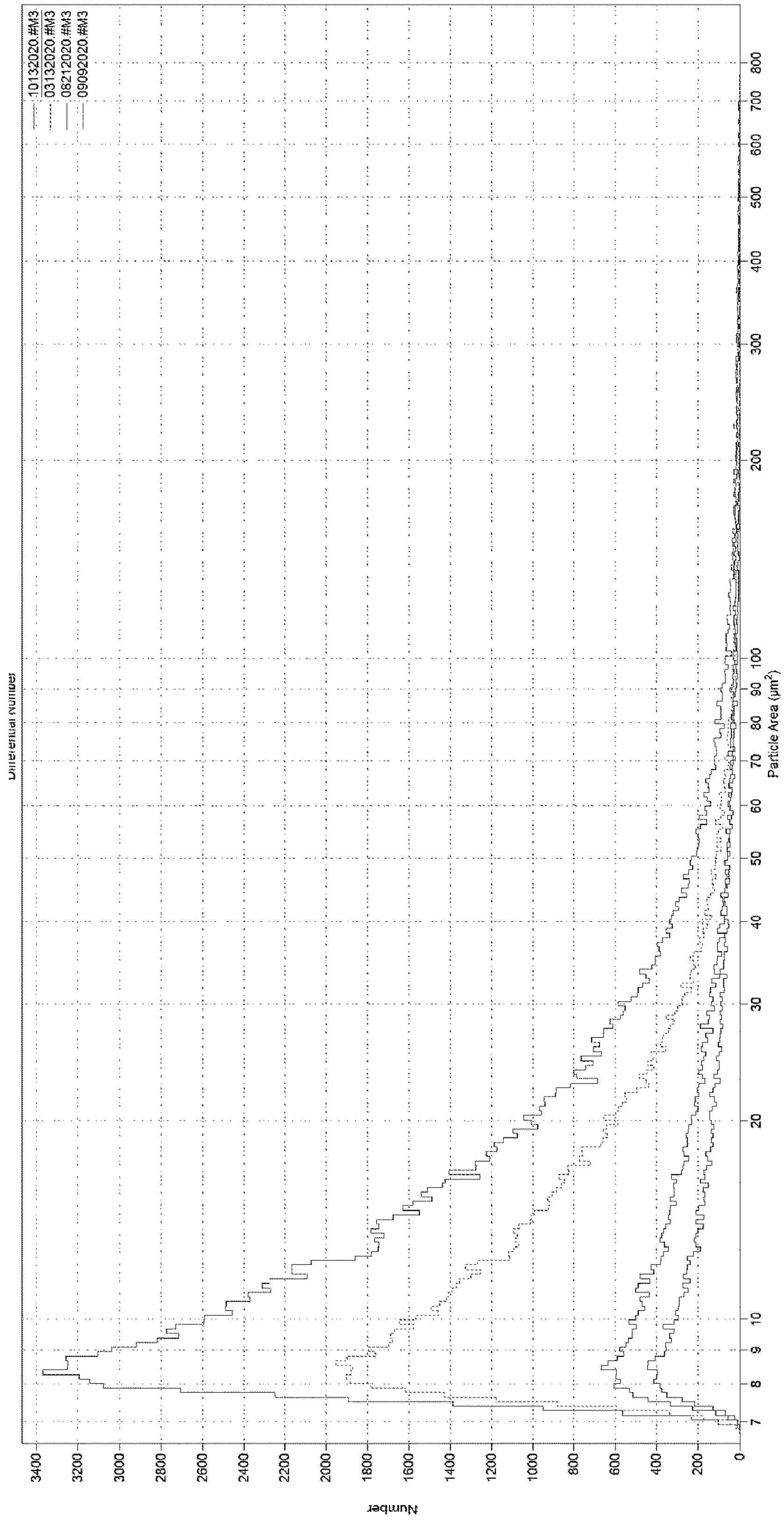
FIG. 32 illustrates sizes of particles of four independent preparations of membrane vesicle aAPCs generating using the nitrogen cavitation method.
Figure 33:
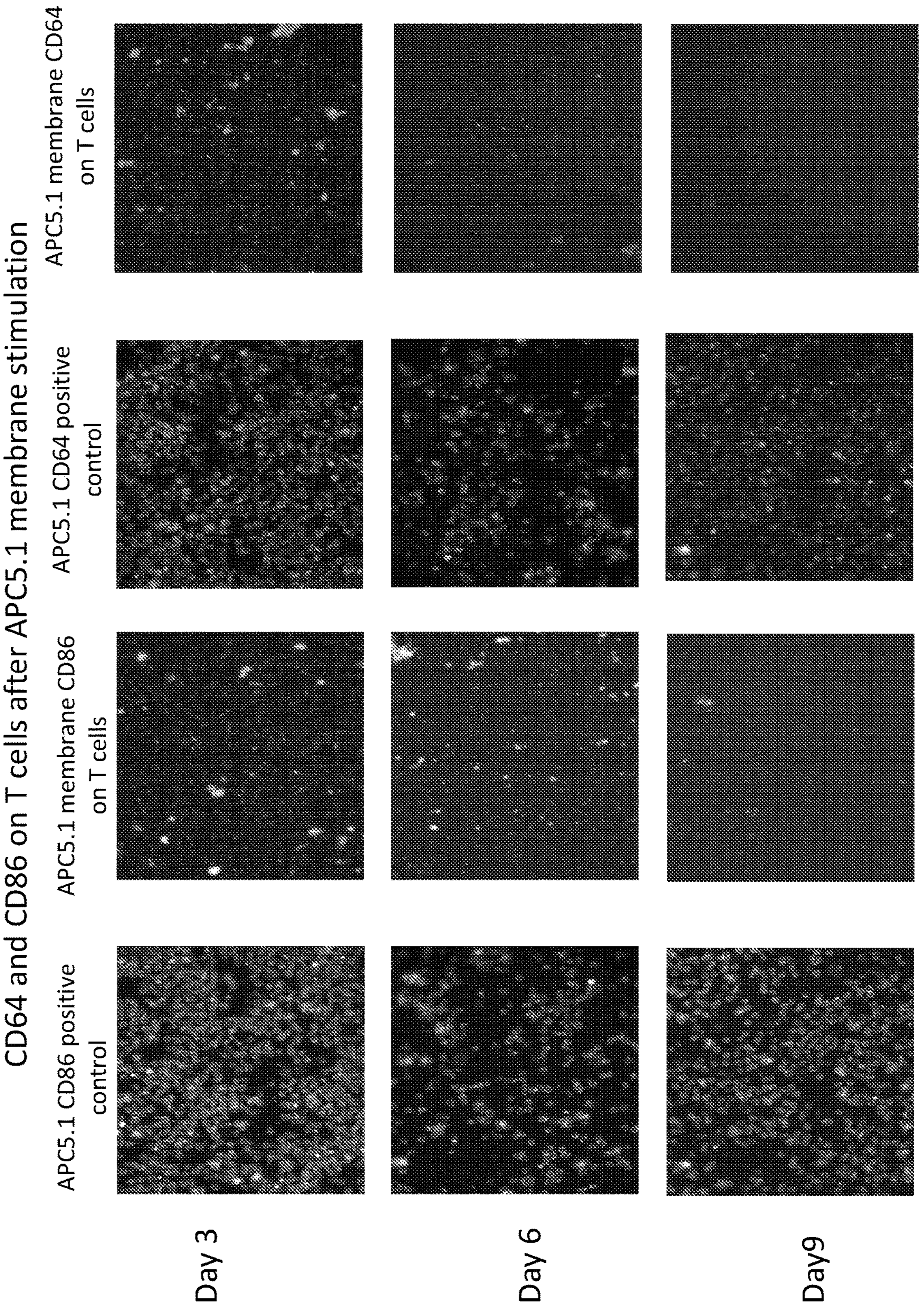
FIG. 33 is a series of micrographs illustrating CD64 and CD86 on T cells after stimulation with aAPC membrane vesicles generated from APC5.1 cells.
Figure 34:
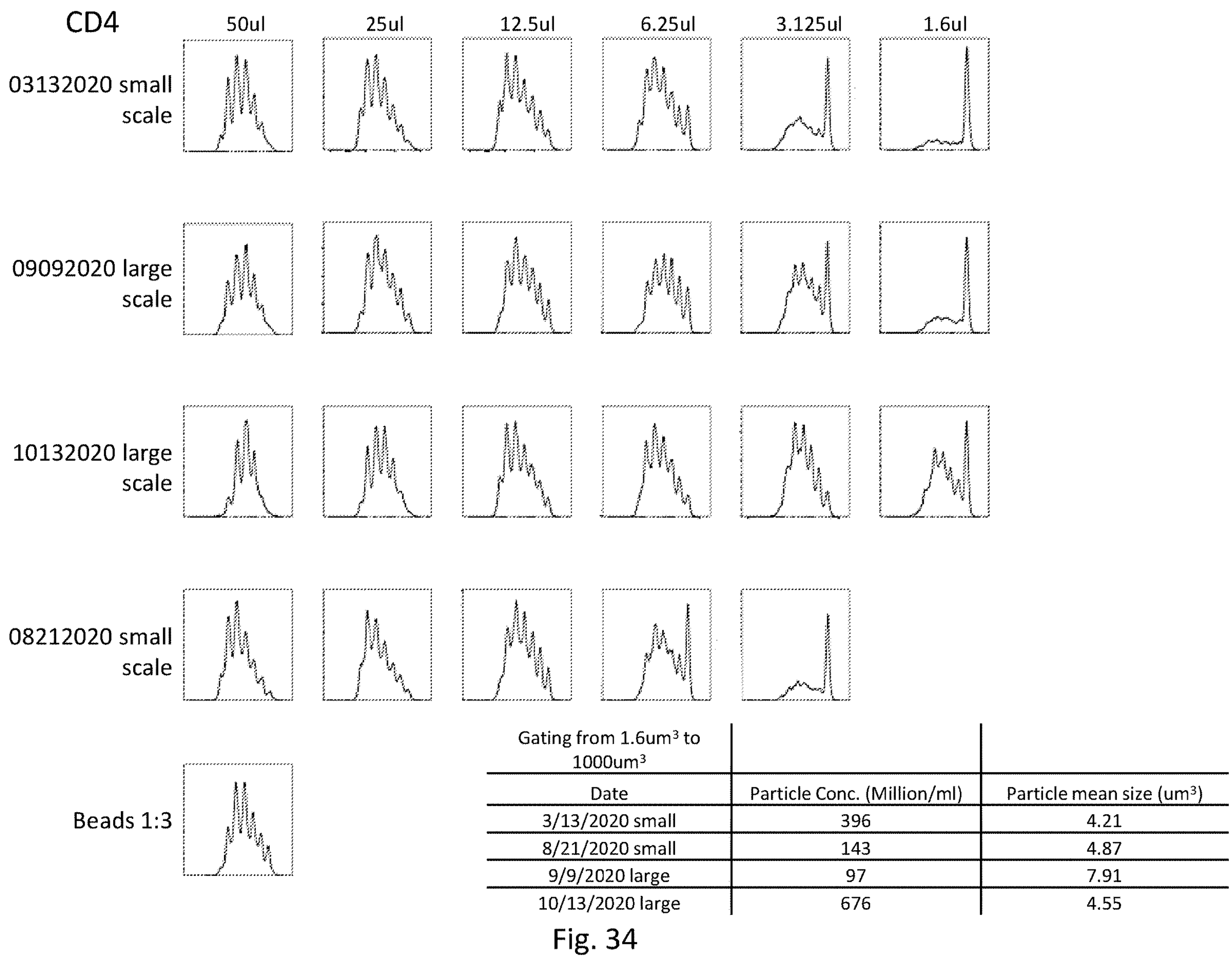
FIG. 34 illustrates the proliferation of human donor CD4+ T cells following incubation with various concentrations of several preparations of aAPC membrane vesicles as compared to anti-CD3/anti-CD28 coated microbeads (“beads”). Inset table illustrates the particle concentration and mean particle size of each membrane vesicle preparation.
Figure 35:
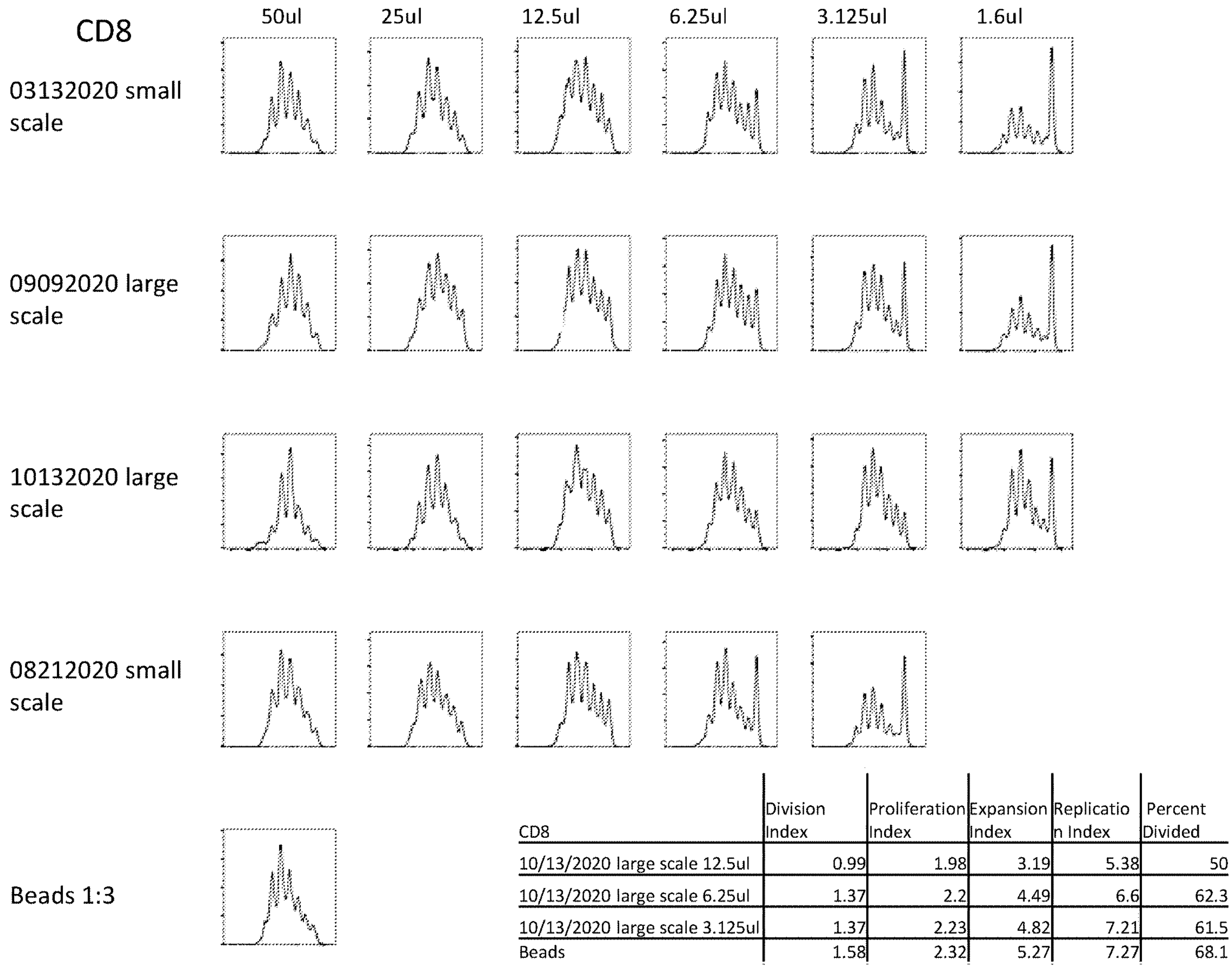
FIG. 35 illustrates the proliferation of human donor CD8+ T cells following incubation with various concentrations of several preparations of aAPC membrane vesicles as compared to anti-CD3/anti-CD28 coated microbeads (“beads”). Inset table illustrates the division index, expansion index, replication index, and percent division resulting from each membrane vesicle preparation.
Figure 36:
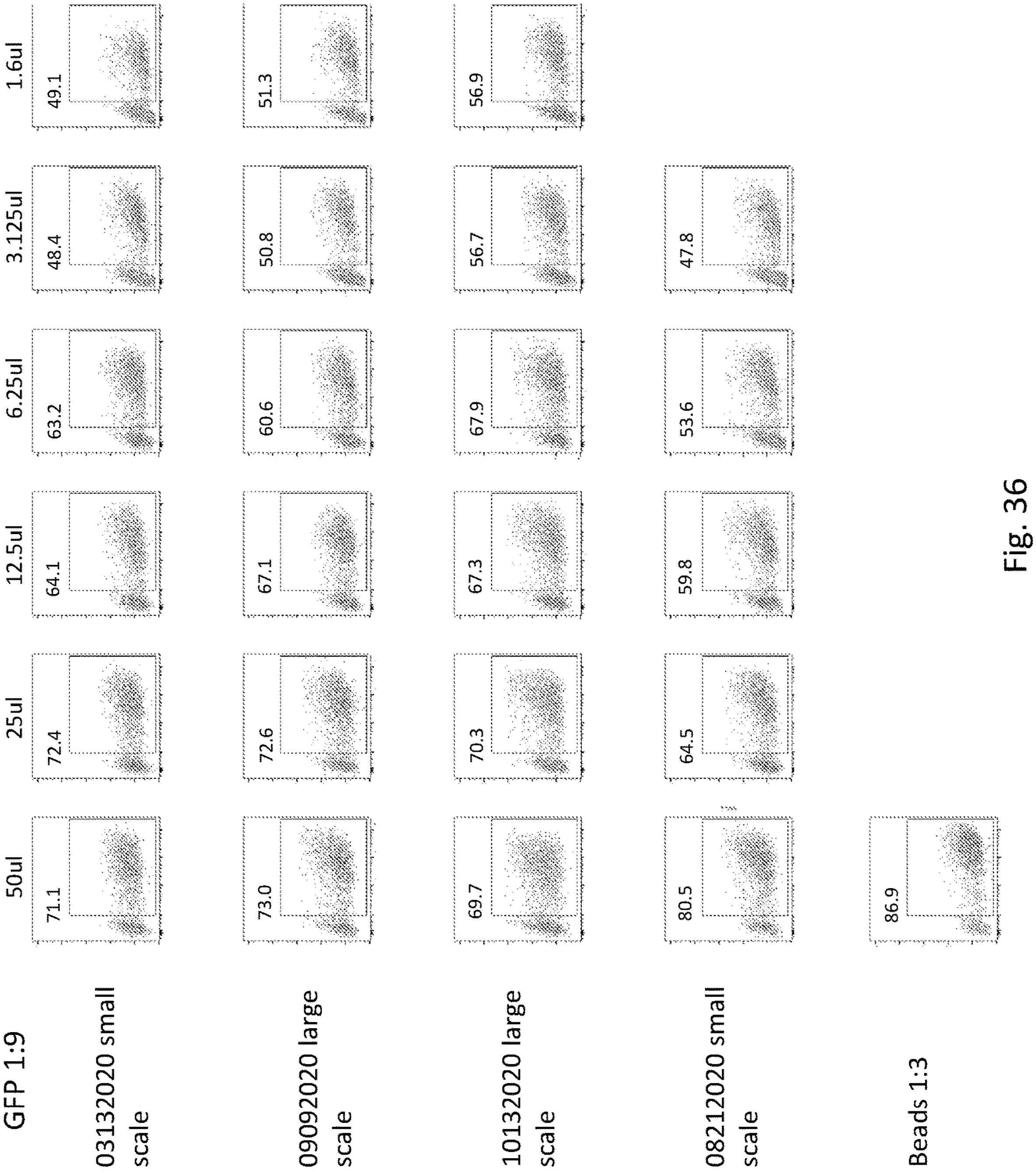
FIG. 36 illustrates the lentiviral transduction of T cells during expansion with various concentrations of several preparations of aAPC membrane vesicles as compared to anti-CD3/anti-CD28 coated beads.

The production of functional nanoparticles or membrane vesicles from the APCs of the present disclosure would offer several benefits for large-scale T cell expansion over intact aAPCs. For applications requiring the simultaneous transduction of expanding T cells, the use of aAPC-derived vesicles could increase the efficiency of viral transduction systems. For example, the aAPC-derived vesicles would be less able to interact with the viral particles, thus preventing the aAPC portion of the culture mixture from absorbing significant amounts of virus. Likewise, aAPC-derived vesicles obviate the need for inactivation of the aAPCs through treatments such as cytotoxic chemicals, irradiation, or the like that may negatively affect the cultured T cells. Further, aAPC vesicles are not metabolically active and do not require subsequent purification procedures to remove them from the resulting population of expanded T cells. While many methods of cell disruption are known in the art and would be appropriate for the generation of aAPC-derived vesicles or nanoparticles, the method of nitrogen cavitation offers several advantages in that the method is simple and requires minimal cell manipulation and no chemical detergents. FIG. 31A illustrates two examples of nitrogen cavitation pressure vessels (also known as "bombs"). FIG. 31B illustrates a sample workflow of the generation of aAPC-derived membrane vesicles. FIG. 32 illustrates a series of studies in which APC5.1 cells of the current invention were used to create vesicle preparations using nitrogen cavitation. The graph illustrates the mean size of the particles resulting from the procedure. These preparations of APC5.1-derived vesicles were then incubated with human donor T cells for nine days. FIG. 33 illustrates that CD86 and CD64 molecules originating from the vesicle preparations was observed to be present on the surface of the T cells, indicating successful interaction between the cells and vesicles. FIGS. 34 and 35 illustrate the ability of aAPC-derived vesicles to induce the proliferation of T cells in vitro. Anti-CD3/anti-CD28 coated beads were used as a comparison, as one of the most commonly used methods for expanding T cells. Both CD8+ and CD4+ T cells exhibited equivalent or better proliferation as compared to beads at various concentrations of vesicles ranging from 3.125 μl to 50 μl. Similar studies were also conducted to observe whether aAPC-derived vesicle stimulation of T cells could also support the concurrent viral transduction of T cells using a lentiviral vector bearing a GFP-expressing construct (FIG. 36). Similar to the proliferation data, aAPC-derived vesicle expanded T cells demonstrated robust expression of GFP at levels comparable to bead-stimulated T cells at a number of concentrations. In all, these data suggested the utility of aAPC-derived vesicles as a method of efficient expansion of T cells comparable to anti-CD3/anti-CD28 microbeads (FIG. 37).

Enumerated Embodiments

The following enumerated embodiments are provided, the numbering of which is not to be construed as designating levels of importance.

Embodiment 1 provides an artificial antigen presenting cell (aAPC) comprising a chimeric receptor molecule comprising an antigen binding domain having specificity for human CD3 and a non-human primate CD3, and a transmembrane domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

Embodiment 2 provides the aAPC of embodiment 1, wherein the antigen binding domain comprises a heavy chain variable region comprising the amino acid sequence set forth in SEQ ID NO: 6.

Embodiment 3 provides the aAPC of embodiments 1 or 2, wherein the antigen binding domain comprises a light chain variable region comprising the amino acid sequence set forth in SEQ ID NO: 7.

Embodiment 4 provides the aAPC of any preceding embodiment, wherein the antigen binding domain comprises a heavy chain variable region comprising the amino acid sequence set forth in SEQ ID NO: 6, and a light chain variable region comprising the amino acid sequence set forth in SEQ ID NO: 7.

Embodiment 5 provides the aAPC of any preceding embodiment, wherein the antigen binding domain is a single chain variable fragment (scFv).

Embodiment 6 provides the aAPC of embodiment 5, wherein the scFv comprises the amino acid sequence set forth in SEQ ID NO: 8.

Embodiment 7 provides the aAPC of any preceding embodiment, wherein the non-human primate is *Macaca fascicularis.*

Embodiment 8 provides the aAPC of any preceding embodiment, wherein the non-human primate is *Macaca mulatta.*

Embodiment 9 provides the aAPC of any preceding embodiment, wherein the chimeric receptor molecule further comprises an intracellular domain.

Embodiment 10 provides the aAPC of embodiment 9, wherein the intracellular domain comprises the intracellular domain of CD3 zeta.

Embodiment 11 provides the aAPC of embodiment 9, wherein the intracellular domain comprises the amino acid sequence set forth in SEQ ID NO: 19.

Embodiment 12 provides an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

Embodiment 13 provides the aAPC of embodiment 12, wherein the intracellular domain comprises the intracellular domain of CD3 zeta.

Embodiment 14 provides the aAPC of embodiment 12, wherein the intracellular domain comprises the amino acid sequence set forth in SEQ ID NO: 19.

Embodiment 15 provides an artificial antigen presenting cell (aAPC) comprising a chimeric receptor molecule comprising an antigen binding domain having specificity for human CD3, and a transmembrane domain, wherein the antigen binding domain comprises:

a heavy chain variable region comprising three heavy chain complementarity determining regions (HCDRs), wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and a light chain variable region comprising three light chain complementarity determining regions (LCDRs), wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14.

Embodiment 16 provides the aAPC of embodiment 15, wherein the antigen binding domain comprises a heavy chain variable region comprising the amino acid sequence set forth in SEQ ID NO: 15.

Embodiment 17 provides the aAPC of embodiment 15 or 16, wherein the antigen binding domain comprises a light chain variable region comprising the amino acid sequence set forth in SEQ ID NO: 16.

Embodiment 18 provides the aAPC of any preceding embodiment, wherein the antigen binding domain comprises a heavy chain variable region comprising the amino acid sequence set forth in SEQ ID NO: 15, and a light chain variable region comprising the amino acid sequence set forth in SEQ ID NO: 16.

Embodiment 19 provides the aAPC of any preceding embodiment, wherein the antigen binding domain is a single chain variable fragment (scFv).

Embodiment 20 provides the aAPC of embodiment 19, wherein the scFv comprises the amino acid sequence set forth in SEQ ID NO: 17.

Embodiment 21 provides the aAPC of any preceding embodiment, wherein the chimeric receptor molecule further comprises a hinge domain.

Embodiment 22 provides the aAPC of embodiment 21, wherein the hinge domain is a CD8 hinge domain.

Embodiment 23 provides the aAPC of embodiment 21, wherein the hinge domain comprises the amino acid sequence set forth in SEQ ID NO: 21.

Embodiment 24 provides the aAPC of any preceding embodiment, wherein the transmembrane domain is a CD8 transmembrane domain.

Embodiment 25 provides the aAPC of any preceding embodiment, wherein the transmembrane domain comprises the amino acid sequence set forth in SEQ ID NO: 22.

Embodiment 26 provides the aAPC of any preceding embodiment, wherein the chimeric receptor molecule comprises the amino acid sequence set forth in SEQ ID NO: 23 or 24.

Embodiment 27 provides the aAPC of any preceding embodiment, wherein the chimeric receptor molecule is encoded by a nucleic acid comprising the nucleic acid sequence set forth in SEQ ID NO: 25 or 26.

Embodiment 28 provides the aAPC of any preceding embodiment, wherein the chimeric receptor molecule consists of the amino acid sequence set forth in SEQ ID NO: 23 or 24.

Embodiment 29 provides the aAPC of any preceding embodiment, wherein the chimeric receptor molecule is encoded by a nucleic acid consisting of the nucleic acid sequence set forth in SEQ ID NO: 25 or 26.

Embodiment 30 provides the aAPC of any preceding embodiment, wherein the chimeric receptor molecule is constitutively expressed.

Embodiment 31 provides the aAPC of any preceding embodiment, wherein the aAPC is an engineered K562 cell.

Embodiment 32 provides the aAPC of any preceding embodiment, wherein the engineered K562 cell does not endogenously express one or more molecules selected from the group consisting of HLA class I, HLA class II, CD1d, CD16, CD64, CD83, CD86, 4-1BBL, OX40L, ICOSL, CD40L, PD-L1, PD-L2, B7-H3, and B7-H4.

Embodiment 33 provides the aAPC of any preceding embodiment, wherein the aAPC further comprises an Fc receptor expressed at the cell surface.

Embodiment 34 provides the aAPC of embodiment 33, wherein the Fc receptor is CD64.

Embodiment 35 provides the aAPC of any preceding embodiment, wherein the aAPC further comprises a co-stimulatory molecule expressed at the cell surface.

Embodiment 36 provides the aAPC of embodiment 35, wherein the co-stimulatory molecule is CD86.

Embodiment 37 provides the aAPC of any preceding claim, wherein the aAPC further comprises an Fc receptor expressed at the cell surface, and a co-stimulatory molecule expressed at the cell surface.

Embodiment 38 provides the aAPC of embodiment 37, wherein the Fc receptor is CD64, and the co-stimulatory molecule is CD86.

Embodiment 39 provides the aAPC of any one of embodiments 33-38, wherein the aAPC is loaded with an antibody, wherein the Fc fragment of the antibody is bound by the Fc receptor.

Embodiment 40 provides the aAPC of embodiment 39, wherein the antibody has specificity for a molecule selected from the group consisting of CD3, CD28, PD-1, B7-H3, 4-1BB, OX40, ICOS, CD30, HLA-DR, MHCII, Toll Ligand Receptor and LFA-1.

Embodiment 41 provides the aAPC of any preceding embodiment, wherein the aAPC further comprises a co-stimulatory ligand.

Embodiment 42 provides the aAPC of embodiment 41, wherein the co-stimulatory ligand is selected from the group consisting of CD7, B7-1 (CD80), PD-L1, PD-L2, 4-1BBL, OX40L, ICOS-L, ICAM, CD30L, CD40, CD70, CD83, HLA-G, MICA, MICB, HVEM, lymphotoxin beta receptor, ILT3, ILT4, 3/TR6, and a ligand that specifically binds with B7-H3.

Embodiment 43 provides the aAPC of embodiment 41 or 42, wherein the co-stimulatory ligand is 4-1BBL.

Embodiment 44 provides the aAPC of any preceding embodiment, wherein the aAPC expresses one or more cytokines selected from the group consisting of IL-2, IL-4, IL-5, IL-7, IL-10, IL-12, IL-13, IL-15, IL-17, IL-18, IL-21, IL-35, and TGF-β.

Embodiment 45 provides the aAPC of any preceding embodiment, wherein the aAPC expresses IL-7.

Embodiment 46 provides the aAPC of any preceding embodiment, wherein the aAPC expresses IL-15.

Embodiment 47 provides the aAPC of any preceding embodiment, wherein the aAPC expresses IL-7 and IL-15.

Embodiment 48 provides the aAPC of any preceding embodiment, wherein the aAPC expresses an IL-15R.

Embodiment 49 provides the aAPC of embodiment 49, wherein the IL-15R is IL-15Rα.

Embodiment 50 provides the aAPC of any one of embodiments 44-49, wherein the cytokine is constitutively expressed.

Embodiment 51 provides an artificial antigen presenting cell (aAPC) comprising:

a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell.

Embodiment 52 provides an artificial antigen presenting cell (aAPC) comprising:

a chimeric receptor molecule comprising an antigen binding domain having specificity for human CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and a light chain variable region comprising three light chain complementarity determining regions (LCDRs), wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14;

CD64;

CD86; and 4-1BBL, and expresses IL-7 and IL-15, wherein the aAPC is an engineered K562 cell.

Embodiment 53 provides the aAPC of embodiment 51 or 52, wherein the aAPC further comprises an IL-15R.

Embodiment 54 provides the aAPC of embodiment 53, wherein the IL-15R is IL-15Rα.

Embodiment 55 provides a composition comprising the aAPC of any preceding embodiment.

Embodiment 56 provides the composition of embodiment 55, further comprising a pharmaceutically acceptable carrier.

Embodiment 57 provides a method for stimulating and expanding a T cell, comprising contacting the T cell with the artificial presenting cell (aAPC) of any one of embodiments 1-56.

Embodiment 58 provides the method of embodiment 57, wherein the T cell is an autologous T cell.

Embodiment 59 provides the method of embodiment 57 or 58, wherein the T cell is a human T cell.

Embodiment 60 provides a method for stimulating and expanding a regulatory T cell (Treg), comprising contacting the Treg with the artificial presenting cell (aAPC) of any one of embodiments 1-56.

Embodiment 61 provides the method of embodiment 60, wherein the regulatory T cell is a human T cell.

Embodiment 62 provides the method of embodiment 60, wherein the regulatory T cell is a non-human primate T cell.

Embodiment 63 provides the method of embodiment 62, wherein the non-human primate is *Macaca fascicularis*.

Embodiment 64 provides the method of embodiment 62, wherein the non-human primate is *Macaca mulatta*.

Embodiment 65 provides a method for stimulating and expanding a T cell, comprising contacting the T cell with an artificial antigen presenting cell (aAPC), wherein the aAPC comprises:

a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell.

Embodiment 66 provides a method for stimulating and expanding a T cell, comprising contacting the T cell with an artificial antigen presenting cell (aAPC), wherein the aAPC comprises:

a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86;

4-1BBL;

IL-15Rα, and expresses IL-7 and IL-15, wherein the aAPC is an engineered K562 cell.

Embodiment 67 provides a composition comprising membrane vesicles derived from an artificial antigen-presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell, and wherein the membrane vesicles are generated by the disruption of the aAPC.

Embodiment 68 provides the composition of embodiment 67, wherein the disruption of the aAPC is accomplished by a method selected from the group consisting of mechanical homogenization, ultrasonic homogenization, pressure homogenization, temperature cycling, and nitrogen cavitation.

Embodiment 69 provides the composition of embodiment 68, wherein the disruption of the aAPC is accomplished by nitrogen cavitation.

Embodiment 70 provides a composition comprising membrane vesicles derived from an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5; and CD64; and CD86; and 4-1BBL; and IL-15Rα; and expresses IL-7 and IL-15, wherein the aAPC is an engineered K562 cell, and wherein the membrane vesicles are generated by the disruption of the aAPC.

Embodiment 71 provides the composition of embodiment 69, wherein the disruption of the aAPC is accomplished by a method selected from the group consisting of mechanical homogenization, ultrasonic homogenization, pressure homogenization, temperature cycling, and nitrogen cavitation.

Embodiment 72 provides the composition of embodiment 71, wherein the disruption of the aAPC is accomplished by nitrogen cavitation.

Embodiment 73 provides a method for stimulating and expanding a T cell, comprising contacting the T cell with the composition of embodiments 67 to 69 or embodiments 70 to 72.

Embodiment 74 provides a method for stimulating and expanding a T cell, comprising contacting the T cell with a composition comprising membrane vesicles derived from an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5;

CD64;

CD86; and 4-1BBL, and expresses IL-7 and IL-15, wherein the aAPC is an engineered K562 cell, and wherein the membrane vesicles are generated by the disruption of the aAPC.

Embodiment 75 provides the method of embodiment 74, wherein disruption of the aAPC is accomplished by a method selected from the group consisting of mechanical homogenization, ultrasonic homogenization, pressure homogenization, temperature cycling, and nitrogen cavitation.

Embodiment 76 provides the method of embodiment 75, wherein the disruption of the aAPC is accomplished by nitrogen cavitation.

Embodiment 77 provides a method for stimulating and expanding a T cell, comprising contacting the T cell with a composition comprising membrane vesicles derived from an artificial antigen presenting cell (aAPC) comprising a chimeric receptor molecule comprising an antigen binding domain having specificity for human CD3 and a non-human primate CD3, a transmembrane domain, and an intracellular domain, wherein the antigen binding domain comprises:

a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5; and CD64; and CD86; and 4-1BBL; and IL-15Rα; and expresses IL-7 and IL-15, wherein the aAPC is an engineered K562 cell, and wherein the membrane vesicles are generated by the disruption of the aAPC.

Embodiment 78 provides the method of embodiment 77, wherein the disruption of the aAPC is accomplished by a method selected from the group consisting of mechanical homogenization, ultrasonic homogenization, pressure homogenization, temperature cycling, and nitrogen cavitation.

Embodiment 79 provides the method of embodiment 78, wherein the disruption of the aAPC is accomplished by nitrogen cavitation.

OTHER EMBODIMENTS

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising membrane vesicles derived from an artificial antigen-presenting cell (aAPC) comprising a chimeric receptor molecule comprising an antigen binding domain having specificity for human CD3 and a non-human primate CD3 or for human CD3, a transmembrane domain, and an intracellular domain, wherein the antigen binding domain comprises:

(a) a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5; or (b) a heavy chain variable region comprising three heavy chain complementarity determining regions (HCDRs), wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and a light chain variable region comprising three light chain complementarity determining regions (LCDRs), wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14;

wherein the membrane vesicles comprise:

the chimeric receptor molecule;

CD86;

4-1BBL;

IL-7; and a complex of IL-15 and IL-15Rα, wherein the aAPC is an engineered K562 cell, and wherein the membrane vesicles are generated by the disruption of the aAPC.

2. The composition of claim 1, wherein the disruption of the aAPC is accomplished by a method selected from the group consisting of mechanical homogenization, ultrasonic homogenization, pressure homogenization, temperature cycling, and nitrogen cavitation.

3. The composition of claim 1, wherein the disruption of the aAPC is accomplished by nitrogen cavitation.

4. The composition of claim 1, wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

5. The composition of claim 1, wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14.

6. The composition of claim 1, wherein the membrane vesicles further comprise:

IL-15Rα.

7. The composition of claim 6, wherein the disruption of the aAPC is accomplished by a method selected from the group consisting of mechanical homogenization, ultrasonic homogenization, pressure homogenization, temperature cycling, and nitrogen cavitation.

8. The composition of claim 6, wherein the disruption of the aAPC is accomplished by nitrogen cavitation.

9. The composition of claim 6, wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

10. The composition of claim 6, wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14.

11. A method for stimulating and expanding a T cell, comprising contacting the T cell with a composition comprising membrane vesicles derived from an artificial antigen presenting cell (aAPC) comprising a chimeric receptor molecule comprising an antigen binding domain having specificity for human CD3 and a non-human primate CD3 or for human CD3, a transmembrane domain, and an intracellular domain, wherein the antigen binding domain comprises:

(a) a heavy chain variable region comprising three heavy chain complementarity determining regions (HCDRs), wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and a light chain variable region comprising three light chain complementarity determining regions (LCDRs), wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5; or (b) a heavy chain variable region comprising three heavy chain complementarity determining regions (HCDRs), wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and a light chain variable region comprising three light chain complementarity determining regions (LCDRs), wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14;

wherein the membrane vesicles comprise:

the chimeric receptor molecule;

CD86;

4-1BBL;

IL-7; and a complex of IL-15 and IL-15Rα, wherein the aAPC is an engineered K562 cell, and wherein the membrane vesicles are generated by the disruption of the aAPC.

12. The method of claim 11, wherein disruption of the aAPC is accomplished by a method selected from the group consisting of mechanical homogenization, ultrasonic homogenization, pressure homogenization, temperature cycling, and nitrogen cavitation.

13. The method of claim 11, wherein the disruption of the aAPC is accomplished by nitrogen cavitation.

14. The method of claim 11, wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

15. The method of claim 11, wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14.

16. The method of claim 11, wherein the membrane vesicles further comprise: IL-15Rα.

17. The method of claim 16, wherein the disruption of the aAPC is accomplished by a method selected from the group consisting of mechanical homogenization, ultrasonic homogenization, pressure homogenization, temperature cycling, and nitrogen cavitation.

18. The method of claim 16, wherein the disruption of the aAPC is accomplished by nitrogen cavitation.

19. The method of claim 16, wherein HCDR1 comprises the amino acid sequence set forth in SEQ ID NO: 1, HCDR2 comprises the amino acid sequence set forth in SEQ ID NO: 2, and HCDR3 comprises the amino acid sequence set forth in SEQ ID NO: 3; and wherein LCDR1 comprises the amino acid sequence set forth in SEQ ID NO: 4, LCDR2 comprises the amino acid sequence GTK, and LCDR3 comprises the amino acid sequence set forth in SEQ ID NO: 5.

20. The method of claim 16, wherein HCDR1 comprises the amino acid sequence set forth in SEQ ID NO: 10, HCDR2 comprises the amino acid sequence set forth in SEQ ID NO: 11, and HCDR3 comprises the amino acid sequence set forth in SEQ ID NO: 12; and wherein LCDR1 comprises the amino acid sequence set forth in SEQ ID NO: 13, LCDR2 comprises the amino acid sequence DTS, and LCDR3 comprises the amino acid sequence set forth in SEQ ID NO: 14.

* * * * *

SEQUENCE LISTING

```
<160> NUMBER OF SEQ ID NOS: 50

<210> SEQ ID NO 1
<211> LENGTH: 8
<212> TYPE: PRT
<213> ORGANISM: Artificial Sequence
<220> FEATURE:
<223> OTHER INFORMATION: F12Q HCDR1

<400> SEQUENCE: 1

Gly Phe Thr Phe Asn Ser Tyr Ala
1               5


<210> SEQ ID NO 2
<211> LENGTH: 10
```

<212> TYPE: PRT
<213> ORGANISM: Artificial Sequence
<220> FEATURE:
<223> OTHER INFORMATION: F12Q HCDR2

<400> SEQUENCE: 2

Ile Arg Ser Lys Tyr Asn Asn Tyr Ala Thr
1               5                   10

<210> SEQ ID NO 3
<211> LENGTH: 16
<212> TYPE: PRT
<213> ORGANISM: Artificial Sequence
<220> FEATURE:
<223> OTHER INFORMATION: F12Q HCDR3

<400> SEQUENCE: 3

Val Arg His Gly Asn Phe Gly Asn Ser Tyr Val Ser Trp Trp Ala Tyr
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: F12Q LCDR1

<400> SEQUENCE: 4

Thr Gly Ala Val Thr Ser Gly Asn Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: F12Q LCDR3

<400> SEQUENCE: 5

Val Leu Trp Tyr Ser Asn Arg Trp Val
1               5

<210> SEQ ID NO 6
<211> LENGTH: 125
<212> TYPE: PRT
<213> ORGANISM: Artificial Sequence
<220> FEATURE:
<223> OTHER INFORMATION: F12Q VH

<400> SEQUENCE: 6

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

```
Ala Tyr Trp Gly Gln Gly Thr Leu Val Thr Val Ser Ser
        115                 120                 125


<210> SEQ ID NO 7
<211> LENGTH: 109
<212> TYPE: PRT
<213> ORGANISM: Artificial Sequence
<220> FEATURE:
<223> OTHER INFORMATION: F112Q VL

<400> SEQUENCE: 7

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105


<210> SEQ ID NO 8
<211> LENGTH: 249
<212> TYPE: PRT
<213> ORGANISM: Artificial Sequence
<220> FEATURE:
<223> OTHER INFORMATION: F12Q scFv

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
```

```
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245


<210> SEQ ID NO 9
<211> LENGTH: 455
<212> TYPE: PRT
<213> ORGANISM: Artificial Sequence
<220> FEATURE:
<223> OTHER INFORMATION: F12Q CAR

<400> SEQUENCE: 9

Met Ala Leu Pro Val Thr Ala Leu Leu Leu Pro Leu Ala Leu Leu Leu
1               5                   10                  15

His Ala Ala Arg Pro Gly Ser Glu Val Gln Leu Val Glu Ser Gly Gly
            20                  25                  30

Gly Leu Val Gln Pro Gly Gly Ser Leu Lys Leu Ser Cys Ala Ala Ser
        35                  40                  45

Gly Phe Thr Phe Asn Ser Tyr Ala Met Asn Trp Val Arg Gln Ala Pro
    50                  55                  60

Gly Lys Gly Leu Glu Trp Val Ala Arg Ile Arg Ser Lys Tyr Asn Asn
65                  70                  75                  80

Tyr Ala Thr Tyr Tyr Ala Asp Ser Val Lys Gly Arg Phe Thr Ile Ser
                85                  90                  95

Arg Asp Asp Ser Lys Asn Thr Ala Tyr Leu Gln Met Asn Asn Leu Lys
            100                 105                 110

Thr Glu Asp Thr Ala Val Tyr Tyr Cys Val Arg His Gly Asn Phe Gly
        115                 120                 125

Asn Ser Tyr Val Ser Trp Trp Ala Tyr Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Gln Thr Val Val Thr Gln Glu Pro Ser Leu Thr Val Ser
                165                 170                 175

Pro Gly Gly Thr Val Thr Leu Thr Cys Gly Ser Ser Thr Gly Ala Val
            180                 185                 190

Thr Ser Gly Asn Tyr Pro Asn Trp Val Gln Gln Lys Pro Gly Gln Ala
        195                 200                 205

Pro Arg Gly Leu Ile Gly Gly Thr Lys Phe Leu Ala Pro Gly Thr Pro
    210                 215                 220

Ala Arg Phe Ser Gly Ser Leu Leu Gly Gly Lys Ala Ala Leu Thr Leu
225                 230                 235                 240

Ser Gly Val Gln Pro Glu Asp Glu Ala Glu Tyr Tyr Cys Val Leu Trp
                245                 250                 255

Tyr Ser Asn Arg Trp Val Phe Gly Gly Gly Thr Lys Leu Thr Val Leu
            260                 265                 270

Ser Gly Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
```

```
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455
```

<210> SEQ ID NO 10
<211> LENGTH: 8
<212> TYPE: PRT
<213> ORGANISM: Artificial Sequence
<220> FEATURE:
<223> OTHER INFORMATION: OKT3 HCDR1

<400> SEQUENCE: 10

```
Gly Tyr Thr Phe Thr Arg Tyr Thr
1               5
```

<210> SEQ ID NO 11
<211> LENGTH: 8
<212> TYPE: PRT
<213> ORGANISM: Artificial Sequence
<220> FEATURE:
<223> OTHER INFORMATION: OKT3 HCDR2

<400> SEQUENCE: 11

```
Ile Asn Pro Ser Arg Gly Tyr Thr
1               5
```

<210> SEQ ID NO 12
<211> LENGTH: 12
<212> TYPE: PRT
<213> ORGANISM: Artificial Sequence
<220> FEATURE:
<223> OTHER INFORMATION: OKT3 HCDR3

<400> SEQUENCE: 12

```
Ala Arg Tyr Tyr Asp Asp His Tyr Cys Leu Asp Tyr
1               5                   10
```

<210> SEQ ID NO 13
<211> LENGTH: 5
<212> TYPE: PRT
<213> ORGANISM: Artificial Sequence
<220> FEATURE:
<223> OTHER INFORMATION: OKT3 LCDR1

<400> SEQUENCE: 13

```
Ser Ser Val Ser Tyr
1               5
```

<210> SEQ ID NO 14
<211> LENGTH: 9
<212> TYPE: PRT
<213> ORGANISM: Artificial Sequence
<220> FEATURE:
<223> OTHER INFORMATION: OKT3 LCDR3

<400> SEQUENCE: 14

```
Gln Gln Trp Ser Ser Asn Pro Phe Thr
1               5
```

<210> SEQ ID NO 15
<211> LENGTH: 119
<212> TYPE: PRT
<213> ORGANISM: Artificial Sequence
<220> FEATURE:
<223> OTHER INFORMATION: OKT3 VH

<400> SEQUENCE: 15

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

<210> SEQ ID NO 16
<211> LENGTH: 106
<212> TYPE: PRT
<213> ORGANISM: Artificial Sequence
<220> FEATURE:
<223> OTHER INFORMATION: OKT3 VL

<400> SEQUENCE: 16

```
Ser Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95
```

```
Phe Gly Ser Gly Thr Lys Leu Glu Ile Asn
            100                 105


<210> SEQ ID NO 17
<211> LENGTH: 244
<212> TYPE: PRT
<213> ORGANISM: Artificial Sequence
<220> FEATURE:
<223> OTHER INFORMATION: OKT3 scFv

<400> SEQUENCE: 17

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ser Gly Gly Gly Gly Ser Gly Gly Gly
        115                 120                 125

Gly Ser Gly Gly Gly Gly Ser Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240

Arg Ala Ala Ala


<210> SEQ ID NO 18
<211> LENGTH: 339
<212> TYPE: PRT
<213> ORGANISM: Artificial Sequence
<220> FEATURE:
<223> OTHER INFORMATION: OKT3 CAR

<400> SEQUENCE: 18

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Ala Arg Pro Gly Ala Ser Val Lys Met Ser Cys Lys Ala Ser Gly Tyr
        35                  40                  45
```

```
Thr Phe Thr Arg Tyr Thr Met His Trp Val Lys Gln Arg Pro Gly Gln
    50                  55                  60

Gly Leu Glu Trp Ile Gly Tyr Ile Asn Pro Ser Arg Gly Tyr Thr Asn
65                  70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Tyr Tyr Asp Asp His Tyr Cys Leu Asp
        115                 120                 125

Tyr Trp Gly Gln Gly Thr Thr Leu Thr Val Ser Ser Ser Gly Gly Gly
    130                 135                 140

Gly Ser Gly Gly Gly Gly Ser Gly Gly Gly Gly Ser Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met Asn Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Ala His Phe Arg Gly Ser Gly Ser Gly Thr Ser
    210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ala Ala Ala Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys


<210> SEQ ID NO 19
<211> LENGTH: 112
<212> TYPE: PRT
<213> ORGANISM: Artificial Sequence
<220> FEATURE:
<223> OTHER INFORMATION: F12Q CAR Intracellular Domain

<400> SEQUENCE: 19

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60
```

```
Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 20
<211> LENGTH: 74
<212> TYPE: PRT
<213> ORGANISM: Artificial Sequence
<220> FEATURE:
<223> OTHER INFORMATION: OKT3 CAR Intracellular Domain

<400> SEQUENCE: 20

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys Lys Arg Gly Arg Lys
65                  70


<210> SEQ ID NO 21
<211> LENGTH: 45
<212> TYPE: PRT
<213> ORGANISM: Artificial Sequence
<220> FEATURE:
<223> OTHER INFORMATION: CD8 Hinge Domain

<400> SEQUENCE: 21

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 22
<211> LENGTH: 24
<212> TYPE: PRT
<213> ORGANISM: Artificial Sequence
<220> FEATURE:
<223> OTHER INFORMATION: CD8 TM Domain

<400> SEQUENCE: 22

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 23
<211> LENGTH: 455
<212> TYPE: PRT
<213> ORGANISM: Artificial Sequence
<220> FEATURE:
<223> OTHER INFORMATION: F12Q chimeric receptor

<400> SEQUENCE: 23
```

-continued

```
Met Ala Leu Pro Val Thr Ala Leu Leu Leu Pro Leu Ala Leu Leu Leu
1               5                   10                  15

His Ala Ala Arg Pro Gly Ser Glu Val Gln Leu Val Glu Ser Gly Gly
            20                  25                  30

Gly Leu Val Gln Pro Gly Gly Ser Leu Lys Leu Ser Cys Ala Ala Ser
        35                  40                  45

Gly Phe Thr Phe Asn Ser Tyr Ala Met Asn Trp Val Arg Gln Ala Pro
    50                  55                  60

Gly Lys Gly Leu Glu Trp Val Ala Arg Ile Arg Ser Lys Tyr Asn Asn
65                  70                  75                  80

Tyr Ala Thr Tyr Tyr Ala Asp Ser Val Lys Gly Arg Phe Thr Ile Ser
                85                  90                  95

Arg Asp Asp Ser Lys Asn Thr Ala Tyr Leu Gln Met Asn Asn Leu Lys
            100                 105                 110

Thr Glu Asp Thr Ala Val Tyr Tyr Cys Val Arg His Gly Asn Phe Gly
        115                 120                 125

Asn Ser Tyr Val Ser Trp Trp Ala Tyr Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Gln Thr Val Val Thr Gln Glu Pro Ser Leu Thr Val Ser
                165                 170                 175

Pro Gly Gly Thr Val Thr Leu Thr Cys Gly Ser Ser Thr Gly Ala Val
            180                 185                 190

Thr Ser Gly Asn Tyr Pro Asn Trp Val Gln Gln Lys Pro Gly Gln Ala
        195                 200                 205

Pro Arg Gly Leu Ile Gly Gly Thr Lys Phe Leu Ala Pro Gly Thr Pro
    210                 215                 220

Ala Arg Phe Ser Gly Ser Leu Leu Gly Gly Lys Ala Ala Leu Thr Leu
225                 230                 235                 240

Ser Gly Val Gln Pro Glu Asp Glu Ala Glu Tyr Tyr Cys Val Leu Trp
                245                 250                 255

Tyr Ser Asn Arg Trp Val Phe Gly Gly Gly Thr Lys Leu Thr Val Leu
            260                 265                 270

Ser Gly Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Arg Val Lys Phe Ser Arg Ser Ala Asp
            340                 345                 350

Ala Pro Ala Tyr Gln Gln Gly Gln Asn Gln Leu Tyr Asn Glu Leu Asn
        355                 360                 365

Leu Gly Arg Arg Glu Glu Tyr Asp Val Leu Asp Lys Arg Arg Gly Arg
    370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
```

```
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455


<210> SEQ ID NO 24
<211> LENGTH: 339
<212> TYPE: PRT
<213> ORGANISM: Artificial Sequence
<220> FEATURE:
<223> OTHER INFORMATION: OKT3 chimeric receptor

<400> SEQUENCE: 24

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Ala Arg Pro Gly Ala Ser Val Lys Met Ser Cys Lys Ala Ser Gly Tyr
        35                  40                  45

Thr Phe Thr Arg Tyr Thr Met His Trp Val Lys Gln Arg Pro Gly Gln
    50                  55                  60

Gly Leu Glu Trp Ile Gly Tyr Ile Asn Pro Ser Arg Gly Tyr Thr Asn
65                  70                  75                  80

Tyr Asn Gln Lys Phe Lys Asp Lys Ala Thr Leu Thr Thr Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Tyr Tyr Asp Asp His Tyr Cys Leu Asp
        115                 120                 125

Tyr Trp Gly Gln Gly Thr Thr Leu Thr Val Ser Ser Ser Gly Gly Gly
    130                 135                 140

Gly Ser Gly Gly Gly Gly Ser Gly Gly Gly Gly Ser Ile Val Leu Thr
145                 150                 155                 160

Gln Ser Pro Ala Ile Met Ser Ala Ser Pro Gly Glu Lys Val Thr Met
                165                 170                 175

Thr Cys Ser Ala Ser Ser Ser Val Ser Tyr Met Asn Trp Tyr Gln Gln
            180                 185                 190

Lys Ser Gly Thr Ser Pro Lys Arg Trp Ile Tyr Asp Thr Ser Lys Leu
        195                 200                 205

Ala Ser Gly Val Pro Ala His Phe Arg Gly Ser Gly Ser Gly Thr Ser
    210                 215                 220

Tyr Ser Leu Thr Ile Ser Gly Met Glu Ala Glu Asp Ala Ala Thr Tyr
225                 230                 235                 240

Tyr Cys Gln Gln Trp Ser Ser Asn Pro Phe Thr Phe Gly Ser Gly Thr
                245                 250                 255

Lys Leu Glu Ile Asn Arg Ala Ala Ala Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
```

325 330 335

Gly Arg Lys

<210> SEQ ID NO 25
<211> LENGTH: 1368
<212> TYPE: DNA
<213> ORGANISM: Artificial Sequence
<220> FEATURE:
<223> OTHER INFORMATION: F12Q chimeric receptor

<400> SEQUENCE: 25
atggccttac cagtgaccgc cttgctcctg ccgctggcct tgctgctcca cgccgccagg 60
ccgggatccg aagtacaact tgtagagtct ggagggggac tcgtccagcc cggtggctcc 120
ctgaaacttt catgcgcagc aagcgggttc acgtttaact cttatgcaat gaattgggtc 180
cgacaagctc caggcaaagg acttgaatgg gtcgccagga ttcggagcaa atacaacaac 240
tacgcgacat attatgctga tagtgtaaaa ggacggttca cgatctcaag agacgattct 300
aagaatacag cgtatcttca aatgaacaac ttgaaaacag aagacaccgc cgtttattat 360
tgcgtcagac atggcaactt tggaaacagt tacgtttctt ggtgggccta ctggggtcaa 420
gggacgcttg tcaccgtcag ctcaggaggc gggggatctg gcggcggcgg ttcaggtggt 480
ggtggatctc agacagtggt cacacaagag ccatcactta ccgtatcccc tggggggact 540
gtaaccctta cctgcgggtc ctctacgggg gctgttacta gcggcaacta tccaaactgg 600
gtgcaacaaa agcctggtca agctccccgc gggctgatcg gcggtactaa gttccttgcg 660
ccgggcactc ctgcaagatt ttcaggttct cttcttgggg gaaaagctgc attgactctc 720
agtggtgtcc agccggagga cgaagccgag tattactgtg tcctctggta ttccaatagg 780
tgggtgttcg gggtggtac taaactcact gtgctttccg gaaccacgac gccagcgccg 840
cgaccaccaa caccggcgcc caccatcgcg tcgcagcccc tgtccctgcg cccagaggcg 900
tgccggccag cggcgggggg cgcagtgcac acgagggggc tggacttcgc ctgtgatatc 960
tacatctggg cgcccttggc cgggacttgt ggggtccttc tcctgtcact ggttatcacc 1020
ctttactgca gagtgaagtt cagcaggagc gcagacgccc ccgcgtacca gcagggccag 1080
aaccagctct ataacgagct caatctagga cgaagagagg agtacgatgt tttggacaag 1140
agacgtggcc gggaccctga gatgggggga aagccgagaa ggaagaaccc tcaggaaggc 1200
ctgtacaatg aactgcagaa agataagatg gcggaggcct acagtgagat tgggatgaaa 1260
ggcgagcgcc ggaggggcaa ggggcacgat ggcctttacc agggtctcag tacagccacc 1320
aaggacacct acgacgccct tcacatgcag gccctgcccc ctcgctaa 1368

<210> SEQ ID NO 26
<211> LENGTH: 1023
<212> TYPE: DNA
<213> ORGANISM: Artificial Sequence
<220> FEATURE:
<223> OTHER INFORMATION: OKT3 chimeric receptor

<400> SEQUENCE: 26
atggcactgc ccgtgaccgc cctcctcctg cccctcgcgc tactcctgca cgccgccaga 60
ccccaggtgc agctgcagca gagtggcgct gagctggccc gccccggcgc ctccgtgaag 120
atgtcctgca aggctagtgg gtataccttc accaggtata ctatgcactg ggtgaagcag 180
cgtccggggc aggggctcga gtggatcggc tacatcaatc cctcccgcgg ctacaccaat 240
tacaaccaga agttcaagga taaggccacg ctgaccacag acaagagtag ctccacggcc 300

```
tacatgcagt tatcaagtct gacctctgag gactccgctg tgtactattg tgcgaggtac    360

tacgacgacc actactgtct ggactactgg ggccaaggca caaccctgac tgtaagttcc    420

tccggcggcg gggggtccgg cggcggcggc tccggcgggg ggggtagtat cgtgctgaca    480

cagagtcccg caatcatgtc cgcaagcccc ggagagaagg tgaccatgac gtgtagtgct    540

tccagctccg tgtcctatat gaactggtac cagcagaaat ccgggacttc ccccaagaga    600

tggatctacg acaccagtaa gctggccagt ggcgtgcctg cacacttccg cggcagtggc    660

tccggcacta gttacagtct caccatctcc gggatggaag ctgaggacgc cgctacctac    720

tactgccagc agtggagctc gaacccattc accttcggtt cggggaccaa gctcgagatc    780

aacagggcgg ccgccaccac gacgccagcg ccgcgaccac caacaccggc gcccaccatc    840

gcgtcgcagc ccctgtccct gcgcccagag gcgtgccggc cagcggcggg gggcgcagtg    900

cacacgaggg ggctggactt cgcctgtgat atctacatct gggcgccctt ggccgggact    960

tgtggggtcc ttctcctgtc actggttatc accctttact gcaaacgggg cagaaagtaa   1020

taa                                                                 1023


<210> SEQ ID NO 27
<211> LENGTH: 5
<212> TYPE: PRT
<213> ORGANISM: Artificial Sequence
<220> FEATURE:
<223> OTHER INFORMATION: GS Linker
<220> FEATURE:
<221> NAME/KEY: REPEAT
<222> LOCATION: (1)..(5)
<223> OTHER INFORMATION: Repeat N times, where N = an integer of at
      least 1.

<400> SEQUENCE: 27

Gly Ser Gly Gly Ser
1               5


<210> SEQ ID NO 28
<211> LENGTH: 4
<212> TYPE: PRT
<213> ORGANISM: Artificial Sequence
<220> FEATURE:
<223> OTHER INFORMATION: GS Linker
<220> FEATURE:
<221> NAME/KEY: REPEAT
<222> LOCATION: (1)..(4)
<223> OTHER INFORMATION: Repeat N times, where N = an integer of at
      least 1.

<400> SEQUENCE: 28

Gly Gly Gly Ser
1


<210> SEQ ID NO 29
<211> LENGTH: 5
<212> TYPE: PRT
<213> ORGANISM: Artificial Sequence
<220> FEATURE:
<223> OTHER INFORMATION: GS Linker
<220> FEATURE:
<221> NAME/KEY: REPEAT
<222> LOCATION: (1)..(5)
<223> OTHER INFORMATION: Repeat N times, where N = an integer of at
      least 1.

<400> SEQUENCE: 29

Gly Gly Gly Gly Ser
```

```
1               5


<210> SEQ ID NO 30
<211> LENGTH: 4
<212> TYPE: PRT
<213> ORGANISM: Artificial Sequence
<220> FEATURE:
<223> OTHER INFORMATION: GS Linker

<400> SEQUENCE: 30

Gly Gly Ser Gly
1


<210> SEQ ID NO 31
<211> LENGTH: 5
<212> TYPE: PRT
<213> ORGANISM: Artificial Sequence
<220> FEATURE:
<223> OTHER INFORMATION: GS Linker

<400> SEQUENCE: 31

Gly Gly Ser Gly Gly
1               5


<210> SEQ ID NO 32
<211> LENGTH: 5
<212> TYPE: PRT
<213> ORGANISM: Artificial Sequence
<220> FEATURE:
<223> OTHER INFORMATION: GS Linker

<400> SEQUENCE: 32

Gly Ser Gly Ser Gly
1               5


<210> SEQ ID NO 33
<211> LENGTH: 5
<212> TYPE: PRT
<213> ORGANISM: Artificial Sequence
<220> FEATURE:
<223> OTHER INFORMATION: GS Linker

<400> SEQUENCE: 33

Gly Ser Gly Gly Gly
1               5


<210> SEQ ID NO 34
<211> LENGTH: 5
<212> TYPE: PRT
<213> ORGANISM: Artificial Sequence
<220> FEATURE:
<223> OTHER INFORMATION: GS Linker

<400> SEQUENCE: 34

Gly Gly Gly Ser Gly
1               5


<210> SEQ ID NO 35
<211> LENGTH: 5
<212> TYPE: PRT
<213> ORGANISM: Artificial Sequence
<220> FEATURE:
<223> OTHER INFORMATION: GS Linker

<400> SEQUENCE: 35

Gly Ser Ser Ser Gly
1               5
```

<210> SEQ ID NO 36
<211> LENGTH: 5
<212> TYPE: PRT
<213> ORGANISM: Artificial Sequence
<220> FEATURE:
<223> OTHER INFORMATION: GS Linker

<400> SEQUENCE: 36

Gly Gly Gly Gly Ser
1 5

<210> SEQ ID NO 37
<211> LENGTH: 15
<212> TYPE: PRT
<213> ORGANISM: Artificial Sequence
<220> FEATURE:
<223> OTHER INFORMATION: GS Linker

<400> SEQUENCE: 37

Gly Gly Gly Gly Ser Gly Gly Gly Gly Ser Gly Gly Gly Gly Ser
1 5 10 15

<210> SEQ ID NO 38
<211> LENGTH: 45
<212> TYPE: DNA
<213> ORGANISM: Artificial Sequence
<220> FEATURE:
<223> OTHER INFORMATION: GS Linker Nuceotide

<400> SEQUENCE: 38
ggtggcggtg gctcgggcgg tggtgggtcg ggtggcggcg gatct 45

<210> SEQ ID NO 39
<211> LENGTH: 5
<212> TYPE: PRT
<213> ORGANISM: Artificial Sequence
<220> FEATURE:
<223> OTHER INFORMATION: Hinge

<400> SEQUENCE: 39

Asp Lys Thr His Thr
1 5

<210> SEQ ID NO 40
<211> LENGTH: 4
<212> TYPE: PRT
<213> ORGANISM: Artificial Sequence
<220> FEATURE:
<223> OTHER INFORMATION: Hinge

<400> SEQUENCE: 40

Cys Pro Pro Cys
1

<210> SEQ ID NO 41
<211> LENGTH: 15
<212> TYPE: PRT
<213> ORGANISM: Artificial Sequence
<220> FEATURE:
<223> OTHER INFORMATION: Hinge

<400> SEQUENCE: 41

Cys Pro Glu Pro Lys Ser Cys Asp Thr Pro Pro Pro Cys Pro Arg
1 5 10 15

<210> SEQ ID NO 42
<211> LENGTH: 12
<212> TYPE: PRT
<213> ORGANISM: Artificial Sequence
<220> FEATURE:
<223> OTHER INFORMATION: Hinge

<400> SEQUENCE: 42

Glu Leu Lys Thr Pro Leu Gly Asp Thr Thr His Thr
1 5 10

<210> SEQ ID NO 43
<211> LENGTH: 10
<212> TYPE: PRT
<213> ORGANISM: Artificial Sequence
<220> FEATURE:
<223> OTHER INFORMATION: Hinge

<400> SEQUENCE: 43

Lys Ser Cys Asp Lys Thr His Thr Cys Pro
1 5 10

<210> SEQ ID NO 44
<211> LENGTH: 7
<212> TYPE: PRT
<213> ORGANISM: Artificial Sequence
<220> FEATURE:
<223> OTHER INFORMATION: Hinge

<400> SEQUENCE: 44

Lys Cys Cys Val Asp Cys Pro
1 5

<210> SEQ ID NO 45
<211> LENGTH: 7
<212> TYPE: PRT
<213> ORGANISM: Artificial Sequence
<220> FEATURE:
<223> OTHER INFORMATION: Hinge

<400> SEQUENCE: 45

Lys Tyr Gly Pro Pro Cys Pro
1 5

<210> SEQ ID NO 46
<211> LENGTH: 15
<212> TYPE: PRT
<213> ORGANISM: Artificial Sequence
<220> FEATURE:
<223> OTHER INFORMATION: Hinge

<400> SEQUENCE: 46

Glu Pro Lys Ser Cys Asp Lys Thr His Thr Cys Pro Pro Cys Pro
1 5 10 15

<210> SEQ ID NO 47
<211> LENGTH: 12
<212> TYPE: PRT
<213> ORGANISM: Artificial Sequence
<220> FEATURE:
<223> OTHER INFORMATION: Hinge

<400> SEQUENCE: 47

Glu Arg Lys Cys Cys Val Glu Cys Pro Pro Cys Pro
1 5 10

<210> SEQ ID NO 48

-continued

```
<211> LENGTH: 17
<212> TYPE: PRT
<213> ORGANISM: Artificial Sequence
<220> FEATURE:
<223> OTHER INFORMATION: Hinge

<400> SEQUENCE: 48

Glu Leu Lys Thr Pro Leu Gly Asp Thr Thr His Thr Cys Pro Arg Cys
1               5                   10                  15

Pro


<210> SEQ ID NO 49
<211> LENGTH: 12
<212> TYPE: PRT
<213> ORGANISM: Artificial Sequence
<220> FEATURE:
<223> OTHER INFORMATION: Hinge

<400> SEQUENCE: 49

Ser Pro Asn Met Val Pro His Ala His His Ala Gln
1               5                   10


<210> SEQ ID NO 50
<211> LENGTH: 15
<212> TYPE: PRT
<213> ORGANISM: Artificial Sequence
<220> FEATURE:
<223> OTHER INFORMATION: Hinge

<400> SEQUENCE: 50

Glu Pro Lys Ser Cys Asp Lys Thr Tyr Thr Cys Pro Pro Cys Pro
1               5                   10                  15
```